(12) United States Patent
Anandan et al.

(10) Patent No.: US 7,345,043 B2
(45) Date of Patent: *Mar. 18, 2008

(54) INHIBITORS OF HISTONE DEACETYLASE

(75) Inventors: Sampath K. Anandan, Fremont, CA (US); Xiao-Yi Xiao, San Diego, CA (US); Dinesh V. Patel, Fremont, CA (US); John Ward, Redwood City, CA (US)

(73) Assignee: Miikana Therapeutics, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/096,550

(22) Filed: Apr. 1, 2005

(65) Prior Publication Data

US 2005/0234033 A1 Oct. 20, 2005

Related U.S. Application Data

(60) Provisional application No. 60/559,692, filed on Apr. 1, 2004.

(51) Int. Cl.
*A61K 31/497* (2006.01)
*A61K 31/427* (2006.01)
*A61K 31/4535* (2006.01)
*A61K 31/454* (2006.01)
*C07D 417/04* (2006.01)
*C07D 277/28* (2006.01)

(52) U.S. Cl. .............. 514/254.02; 514/326; 514/371; 544/367; 546/209; 548/190; 548/200

(58) Field of Classification Search ............ 514/254.02, 514/326, 371; 544/367; 546/209; 548/190, 548/200
See application file for complete search history.

(56) References Cited

U.S. PATENT DOCUMENTS 5,925,672 A * 7/1999 Piomelli et al. ............ 514/460

FOREIGN PATENT DOCUMENTS

EP 0827742 3/1998

OTHER PUBLICATIONS

Marks et al. "Histone Deacetylases and Cancer: Causes and Therapies" *Nature Reviews: Cancer* 1:194-202 (2001).
Finnin et al. "Structures of a histone deacetylase homologue bound to the TSA and SAHA Inhibitors" *Nature* 401:188-193 (1999).
Hamada et al. "An Improved Synthesis of Arylsulfonyl Chlorides from Aryl Halides" *Synthesis-Communication* 852-854 (1986).
Huang et al. "Design, Synthesis and Structure-Activity Relationships of Benzoxazinone-Based Factor Xa Inhibitors" *Biorg. Med. Chem. Lett.* 13:561-566 (2003).
Morimoto et al. "Potent and Selective ET-A Antagonists. 2. Disclvery and Evaluation of Potent and Water Soluble N-(6-(2-(Aryloxy)ethoxy)-4-pyrimidinyl)sulfonamide Derivatives" *J. Med. Chem.* 44:3369-3377.

* cited by examiner

*Primary Examiner*—Joseph K. McKane
*Assistant Examiner*—Yong Chu
(74) *Attorney, Agent, or Firm*—King & Spalding

(57) ABSTRACT

Disclosed are compounds which inhibit histone deacetylase (HDAC) enzymatic activity. Also disclosed are pharmaceutical compositions comprising such compounds as well as methods to treat conditions, particularly proliferative conditions, mediated at least in part by HDAC.

19 Claims, No Drawings

INHIBITORS OF HISTONE DEACETYLASE

CROSS-REFERENCE TO RELATED CASES

This application claims the benefit under 35 U.S.C. §119 (e) of U.S. Provisional Application Ser. No. 60/559,692 filed Apr. 1, 2004, which is incorporated herein by reference in its entirety.

BACKGROUND OF THE INVENTION

1. Field of the Invention

This invention relates to compounds which inhibit histone deacetylase (HDAC) enzymatic activity. This invention is also directed to pharmaceutical compositions comprising such compounds as well as to treat conditions, particularly proliferative conditions, mediated at least in part by HDAC.

REFERENCES

The following publications, patents and patent applications are cited in this application as superscript numbers:

1. Marks, et al., Nature Reviews: Cancer 1: 194-202 (2001)
2. Finnin, et al., Nature, 401:188-193 (1999)
3. Geerts, et al., European Patent Application Publication No. 0 827 742, published Mar. 11, 1998

All of the above publications, patents and patent applications are herein incorporated by reference in their entirety to the same extent as if each individual publication, patent or patent application was specifically and individually indicated to be incorporated by reference in its entirety.

2. State of the Art

In all eukaryotic cells, genomic DNA in chromatine associates with histones to form nucleosomes. Each nucleosome consists of a protein octamer made up of two copies of each histone: H2A, H$_2$B, H3 and H4. DNA winds around this protein core, with the basic amino acids of the histones interacting with the negatively charged phosphate groups of the DNA. The most common posttranslational modification of these core histones is the reversible acetylation of the ε-amino groups of conserved highly basic N-terminal lysine residues. The steady state of histone acetylation is established by the dynamic equilibrium between competing histone acetyltransferase(s) and histone deacetylase(s) herein referred to as HDAC. Histone acetylation and deacetylation has long been linked to transcriptional control. The recent cloning of the genes encoding different histone acetyltransferases and histone deacetylases provide a possible explanation for the relationship between histone acetylation and transcriptional control. The reversible acetylation of histones can result in chromatin remodeling and as such act as a control mechanism for gene transcription. In general, hyperacetylation of histones facilitates gene expression, whereas histone deacetylation is correlated with transcriptional repression. Histone acetyltransferases were shown to act as transcriptional coactivators, whereas deacetylases were found to belong to transcriptional repression pathways.

The dynamic equilibrium between histone acetylation and deacetylation is essential for normal cell growth. Inhibition of histone deacetylation results in cell cycle arrest, cellular differentiation, apoptosis and reversal of the transformed phenotype. Therefore, HDAC inhibitors can have great therapeutic potential in the treatment of cell proliferative diseases or conditions.[1]

The study of inhibitors of histone deacetylases (HDAC) indicates that indeed these enzymes play an important role in cell proliferation and differentiation. The inhibitor Trichostatin A (TSA) causes cell cycle arrest at both the G1 and G2 phases, reverts the transformed phenotype of different cell lines, and induces differentiation of Friend leukemia cells and others. TSA (and suberoylanilide hydroxamic acid SAHA) have been reported to inhibit cell growth, induce terminal differentiation, and prevent formation of tumors in mice.[2]

Trichostatin A has also been reported to be useful in the treatment of fibrosis, e.g., liver fibrosis and liver chirrhosis.[3]

In view of the above, there is an ongoing need for inhibitors/antagonists of HDAC.

SUMMARY OF THE INVENTION

This invention provides compounds which inhibit HDAC activity and, accordingly, are useful as anti-proliferative agents in the treatment of proliferative diseases.

Accordingly, in one of its composition aspects, this invention is directed to a compound of Formula I:

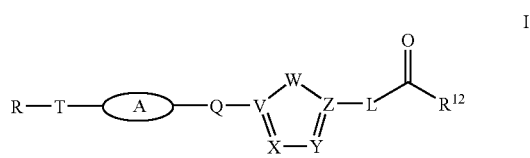

wherein:
R is selected from the group consisting of hydrogen, aryl, substituted aryl, heteroaryl, substituted heteroaryl, alkyl and substituted alkyl;

$R^{12}$ is selected from the group consisting of —NR$^{14}$OH, —OH, —NR$^{14}$R$^{15}$, —OR$^{14}$, —(C$_{1-C6}$)alkylene-SR$^{14}$, —(C$_1$-C$_6$)alkylene-OR$^{14}$, —(C$_1$-C$_6$)alkylene-NR$^{14}$R$^{15}$, —CF$_3$;

where R$^{14}$ and R$^{15}$ are independently selected from the group consisting of hydrogen, (C$_1$-C$_6$)alkyl, (C$_1$-C$_6$) substituted alkyl, aryl, substituted aryl and where R$^{14}$ and R$^{15}$ together with the nitrogen atom bound thereto form a heterocyclic or substituted heterocyclic ring;

V, W, X, Y, and Z form a 5-membered heteroaryl where W, X, and Y are independently selected from =C(R$^{11}$)—, —N=, —N(R$^{14}$)—, —O—, —S—, —S(O)—, and/or —S(O)$_2$—, and V and Z independently form =C(R$^{14}$)— and/or >N— where R$^{14}$ is as defined above and provided that at least one of V, W, X, Y and Z is =C(R$^{14}$)—, and further provided that the ring formed by V, W, X, Y, and Z is not a thiophene;

the ring defined by A above is selected from the group consisting of cycloakylene, substituted cycloalkylene, heterocyclene, substituted heterocyclene, arylene, heteroarylene, -het-(L$^2$)$_b$-het-, -het-(L$^2$)$_b$-cyclo-, -cyclo-(L$^2$)$_b$-het-, and -cyclo-(L$^2$)$_b$-cyclo-;

where each b is independently 0 or 1;

L$^2$ is selected from the group consisting of a covalent bond, (C$_1$-C$_4$)alkylene, substituted (C$_1$-C$_4$)alkylene, —NH(C$_1$-C$_4$)alkylene, (C$_1$-C$_4$)alkyleneNH—, provided that the nitrogen atom of the —NH(C$_1$-C$_4$) alkylene and (C$_1$-C$_4$)alkyleneNH— group are not attached to a nitrogen atom in the het or in cyclo groups;

T is selected from the group consisting of a bond, —SO$_2$—[(C$_1$-C$_3$)alkylene]$_p$—, —[(C$_1$-C$_3$)alkylene]$_p$—SO$_2$—, —NR$^{16}$SO$_2$—[(C$_1$-C$_3$)alkylene]$_p$—, —SO$_2$NR$^{16}$—[(C$_1$-C$_3$)alkylene]$_p$—, —C(O)—[(C$_1$-

C$_3$)alkylene]$_p$—, —[(C$_1$-C$_3$)alkylene]$_p$—C(O)—, —NR$^{16}$C(O)—[(C$_1$-C$_3$)alkylene]$_p$—, —C(O)NR$^{16}$—[(C$_1$-C$_3$)alkylene]$_p$—, —N(R$^{16}$)—[(C$_1$-C$_3$)alkylene]$_p$ and (C$_1$-C$_3$)alkylene where p is zero or one and R$^{16}$ is hydrogen, alkyl, aryl, or heteroaryl, provided that when T is connected to A at a nitrogen atom and T is —SO$_2$NR$^{16}$—[(C$_1$-C$_3$)alkylene]$_p$—, —C(O)NR$^{16}$—[(C$_1$-C$_3$)alkylene]$_p$—, or —N(R$^{16}$)[(C$_1$-C$_3$)alkylene]$_p$ then p is not zero;

Q is selected from the group consisting of a covalent bond, —O—, (C$_1$-C$_3$)alkylene, —C(O)—, —SO$_2$—, —NR$^1$C(O)NR$^1$—, —NR$^1$C(O)—, —C(O)NR$^1$—, —(C$_1$-C$_3$-alkylene)$_p$NR$^1$— and —NR$^1$—(C$_1$-C$_3$-alkylene)$_p$ where R$^1$ is hydrogen or alkyl and p is zero or one, provided that when Q is one of —NR$^1$C(O)NR$^1$—, —NR$^1$C(O)—, —C(O)NR$^1$—, —(C$_1$-C$_3$-alkylene)$_p$NR$^1$—, or —NR$^1$—(C$_1$-C$_3$-alkylene)$_p$ and p is not zero Q is not attached to a nitrogen atom;

L is selected from the group consisting of a covalent bond, (C$_1$-C$_4$)alkylene, substituted (C$_1$-C$_4$)alkylene, (C$_2$-C$_4$) alkenylene, and substituted (C$_2$-C$_4$)alkenylene, (C$_3$-C$_8$) cycloalkylene, and substituted (C$_3$-C$_8$)cycloalkylene;

and tautomers, isomers, prodrugs and pharmaceutically acceptable salts thereof.

Preferred heteroaryl groups defined by V, W, X, Y and Z include furan, imidazole, pyrrazole, isoxazole, isothiazole, oxadiazole, thiazole, tetrazole, triazole, oxazole, pyrrole, thiadiazole, and the like, excluding thiophene.

In another of its composition aspects, this invention is directed to a compound of Formula Ia:

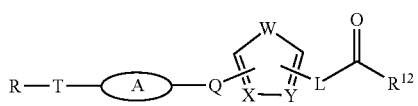

Ia wherein:
R is selected from the group consisting of alkyl, substituted alkyl, aryl, substituted aryl, heteroaryl and substituted heteroaryl;

R$^{12}$ is selected from the group consisting of —NR$^{14}$OH, —OH, —NR$^{14}$R$^{15}$, —OR$^{14}$, —(C$_1$-C$_6$)alkylene-SR$^4$, —(C$_1$-C$_6$)alkylene-OR$^{14}$, —(C$_1$-C$_6$)alkylene-NR$^{14}$R$^{15}$, —CF$_3$;

where R$^{14}$, R$^{15}$ are independently selected from the group consisting of hydrogen, (C$_1$-C$_6$)alkyl, (C$_1$-C$_6$)substituted alkyl, aryl, substituted aryl and where R$^{14}$ and R$^{15}$ together with the nitrogen atom bound thereto form a heterocyclic or substituted heterocyclic ring;

the ring defined by A above is selected from the group consisting of cycloakylene, substituted cycloalkylene, hetrocyclene, substituted heterocyclene, arylene, heteroarylene, -het-(L$^2$)$_b$-het-, -het-(L$^2$)$_b$-cyclo-, -cyclo-(L$^2$)$_b$-het-, and -cyclo-(L$^2$)$_b$-cyclo-;

where each b is independently 0 or 1;

L$^2$ is selected from the group consisting of a covalent bond, (C$_1$-C$_4$)alkylene, substituted (C$_1$-C$_4$)alkylene, —NH(C$_1$-C$_4$)alkylene, (C$_1$-C$_4$)alkyleneNH—, provided that the nitrogen atom of the —NH(C$_1$-C$_4$) alkylene and (C$_1$-C$_4$)alkyleneNH— group are not attached to a nitrogen atom in the het or in cyclo groups;

T is selected from the group consisting of —SO$_2$—[(C$_1$-C$_3$)alkylene]$_p$—, —[(C$_1$-C$_3$)alkylene]$_p$—SO$_2$—, —NR$^{16}$SO$_2$—[(C$_1$-C$_3$)alkylene]$_p$—, —SO$_2$NR$^{16}$—[(C$_1$-C$_3$)alkylene]$_p$—, —C(O)—[(C$_1$-C$_3$)alkylene]$_p$—, —[(C$_1$-C$_3$)alkylene]$_p$—C(O)—, —NR$^{16}$C(O)—[(C$_1$-C$_3$)alkylene]$_p$—, —C(O)NR$^{16}$—[(C$_1$-C$_3$)alkylene]$_p$—, —N(R$^{16}$)—[(C$_1$-C$_3$)alkylene]$_p$ and (C$_1$-C$_3$)alkylene where p is zero or one and R$^{16}$ is hydrogen, alkyl, aryl, or heteroaryl, provided that when T is connected to A at a nitrogen atom and T is —SO$_2$NR$^{16}$—[(C$_1$-C$_3$)alkylene]$_p$—, —C(O)NR$^{16}$—[(C$_1$-C$_3$)alkylene]$_p$—, or —N(R$^{16}$)—[(C$_1$-C$_3$)alkylene]$_p$ then p is not zero;

W is selected from the group consisting of —O—, —S—, —S(O)—, —S(O)$_2$— and —NR$^1$— where R$^1$ is as defined below;

X and Y is selected from the group consisting of >CH and >N such that the 5 membered ring defined by W, X, Y and the two >CH groups is a heteroaryl ring, with the proviso that the ring is not thiophene;

Q is selected from the group consisting of a covalent bond, —O—, (C$_1$-C$_3$)alkylene, —C(O)—, —SO$_2$—, —NR$^1$C(O)NR$^1$—, —NR$^1$C(O)—, —C(O)NR$^1$—, —(C$_1$-C$_3$-alkylene)$_p$NR$^1$— and —NR$^1$—(C$_1$-C$_3$-alkylene)$_p$ where R$^1$ is hydrogen or alkyl and p is zero or one; provided that Q is not attached to X, Y or W when W is —O—, —S—, —S(O)—, —S(O)$_2$— and further provided that when Q is —NR$^1$— then Q is attached to a carbon atom of the ring defined by A above;

L is selected from the group consisting of a covalent bond, (C$_1$-C$_4$)alkylene, substituted (C$_1$-C$_4$)alkylene, (C$_2$-C$_4$) alkenylene, and substituted (C$_2$-C$_4$)alkenylene, (C$_3$-C$_8$) cycloalkylene, and substituted (C$_3$-C$_8$)cycloalkylene;

and tautomers, isomers, prodrugs and pharmaceutically acceptable salts thereof.

Preferred A rings in Formulae I and Ia include by are not limited to optionally substituted piperidine, piperazine, morpholine, piperazinone, piperazindione, azetidine, hydantoin, oxazolidine, octahydro-pyrrolo[3,4-c]pyrrole, tetrahydropyridine, hexene, pyrrolidine, and the like.

More preferably, when A is a heterocyclic group, the R-T-A-Q fragment of Formulae I and Ia above is selected from the following structures, wherein b is 0 or 1, each R, R$^1$ and R$^{16}$ are as defined herein above, and further wherein each depicted A ring is optionally substituted with from 1 to 3 substituents selected from hydrogen, (C$_1$-C$_6$)alkyl, (C$_1$-C$_6$)substituted alkyl, aryl, and substituted aryl.

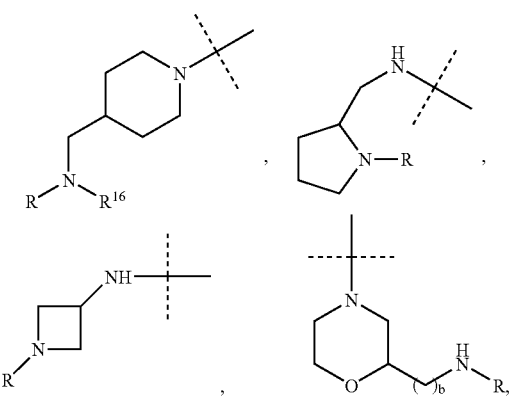

-continued

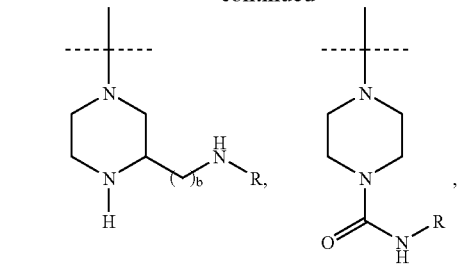

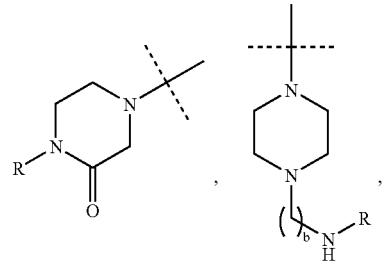

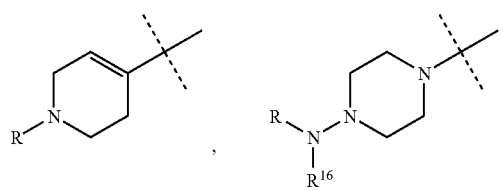

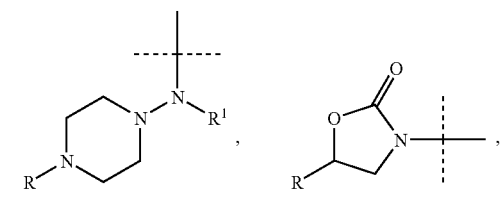

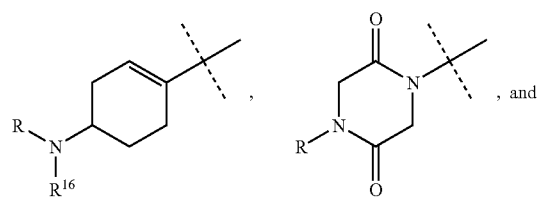

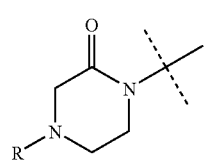

Additional preferred A rings include by are not limited to optionally substituted bicyclic or spirocyclic groups.

More preferably, when the A moiety is a bicyclic or spirocyclic group, the R-T-A-Q fragment of Formulae I and Ia above is selected from the following structures, wherein b is 0 or 1, each R and $R^{16}$ are as defined herein above, and further wherein each depicted A ring is optionally substituted with from 1 to 3 substituents selected from hydrogen, $(C_1-C_6)$alkyl, $(C_1-C_6)$substituted alkyl, aryl, and substituted aryl.

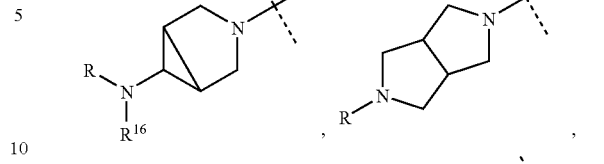

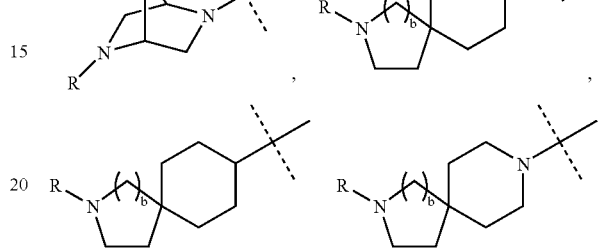

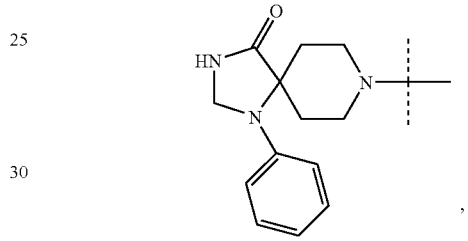

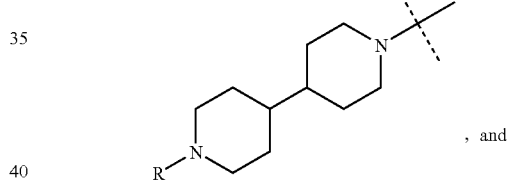

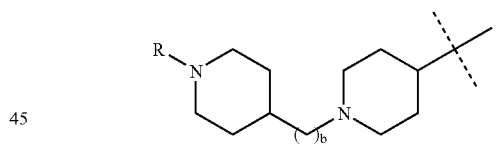

Preferred A rings also include aromatic rings, including, but not limited to, optionally substituted phenyl, pyridine, pyridazine, pyrimidine, triazine, and the like. More preferably, when A is an aromatic ring, the R-T-A-Q fragment of Formulae I and Ia above is selected from the following structures, wherein R and T are as defined hereinabove, and further wherein each depicted A ring is optionally substituted with from 1 to 3 substituents selected from hydrogen, $(C_1-C_6)$alkyl, $(C_1-C_6)$substituted alkyl, aryl, and substituted aryl.

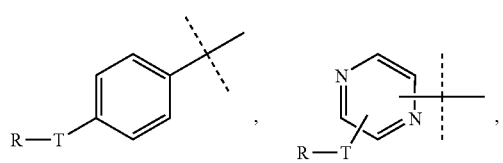

-continued

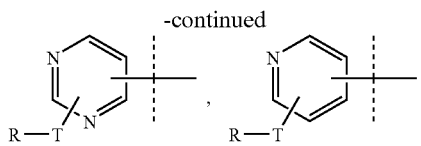

In one preferred embodiment, the compounds of this invention are represented by formula II:

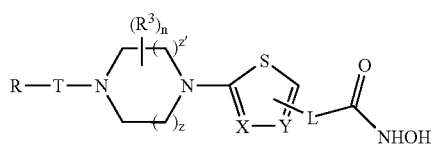

where L, R, T, X and Y are as defined above; each $R^3$ is independently selected from the group consisting of alkyl, substituted alkyl, aryl, substituted aryl, heteroaryl and substituted heteroaryl; n, z, and z' are independently integers equal to zero, one or two, with the proviso that both z and z' are not zero;

as well as tautomers, isomers, prodrugs, and pharmaceutically acceptable salts thereof.

In another preferred embodiment, the compounds of this invention are represented by formula III:

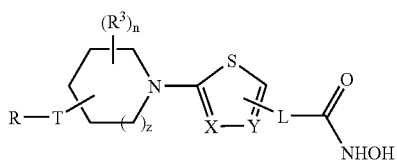

where n, z, L, R, $R^3$, T, X and Y are as defined above; as well as tautomers, isomers, prodrugs and pharmaceutically acceptable salts thereof.

In still another preferred embodiment, the compounds of this invention are represented by formula IV:

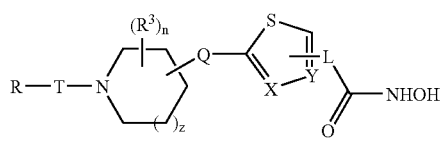

where n, z, L, Q, R, $R^3$, T, X and Y are as defined above, z is zero or one, as well as tautomers, isomers, prodrugs, and pharmaceutically acceptable salts thereof.

In still another preferred embodiment, the compounds of this invention are represented by formula V:

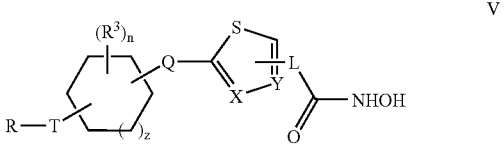

where n, z, L, Q, R, $R^3$, T, X and Y are as defined above as well as tautomers, isomers, prodrugs, and pharmaceutically acceptable salts thereof.

In one embodiment, R is preferably aryl and more preferably is phenyl or naphthyl (e.g., 2-napthyl).

In another embodiment, R is preferably substituted aryl and more preferably, 3,4-dimethoxyphenyl, 4-trifluoromethoxyphenyl, 4-methylphenyl. 4-trifluromethylphenyl, 4-nitrophenyl, 4-acetylphenyl, thiophen-2-yl, biphenyl, 5-(N,N-dimethylamino)-naphthalenyl, and 4-fluorophenyl.

In yet another embodiment, R is preferably alkyl or substituted alkyl, more preferably methyl, benzyl, 2-hydroxyethyl, 2-aminoethyl, and 2-phenylethyl.

In one embodiment, $R^3$ is alkyl and n is one. In another embodiment, n is zero.

Q is preferably a covalent bond, $-NR^1-$, $-(CH_2)NR^1-$, $-SO_2-$, $-C(O)-$, or $-O-$.

In one embodiment, Q is a covalent bond and the ring defined by A above is piperidinyl. In still another embodiment, Q is a covalent bond and the ring defined by A above is piperazinyl.

X is preferably nitrogen and Y is preferably CH.

T is preferably selected from the group consisting of a bond, $-SO_2-$, $-SO_2NH-$, $-CH_2NR^{16}-$.

In one embodiment, L is a covalent bond. In another embodiment, L is an alkenylene group which is preferably ethenylene and more preferably trans (or Z) ethenylene. In still another embodiment, L is a cycloalkylene group, and more preferably cyclopropylene including cis-cyclopropylene and trans-cyclopropylene. In this application, cis-cyclopropylene (as well as cis-cycloalkylene) refers to the groups:

whereas trans-cyclopropylene (as well as trans-cycloalkylene) refers to the groups:

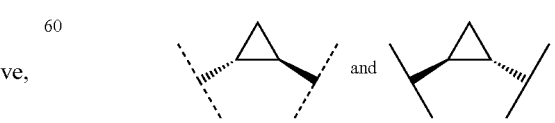

Still another class of compounds of this invention includes compounds of formula VI:

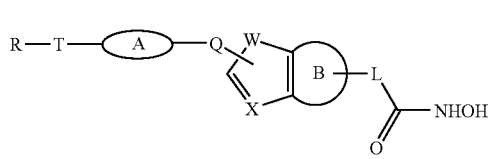

VI

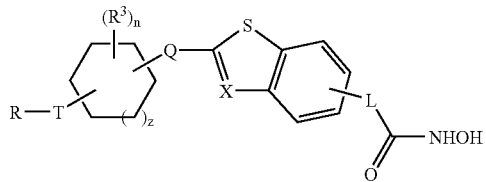

VII where:

R is selected from the group consisting of alkyl, substituted alkyl, aryl, substituted aryl, heteroaryl and substituted heteroaryl;

the ring defined by A above is selected from the group consisting of cycloalkylene, substituted cycloalkylene, heterocyclene and substituted heterocyclene;

T is selected from the group consisting of —SO$_2$—[(C$_1$-C$_3$)alkylene]$_p$—, —[(C$_1$-C$_3$)alkylene]$_p$—SO$_2$—, —NR$^{16}$SO$_2$—[(C$_1$-C$_3$)alkylene]$_p$—, —SO$_2$NR$^{16}$—[(C$_1$-C$_3$)alkylene]$_p$—, —C(O)—[(C$_1$-C$_3$)alkylene]$_p$—, —[(C$_1$-C$_3$)alkylene]$_p$—C(O)—, —NR$^{16}$C(O)—[(C$_1$-C$_3$)alkylene]$_p$—, —C(O)NR$^{16}$—[(C$_1$-C$_3$)alkylene]$_p$—, —N(R$^{16}$)—[(C$_1$-C$_3$)alkylene]$_p$ and (C$_1$-C$_3$)alkylene where p is zero or one and R$^{16}$ is hydrogen, alkyl, aryl, or heteroaryl, provided that when T is connected to A at a nitrogen atom and T is —SO$_2$NR$^{16}$—[(C$_1$-C$_3$)alkylene]$_p$—, —C(O)NR$^{16}$—[(C$_1$-C$_3$)alkylene]$_p$—, or —N(R$^{16}$)—[(C$_1$-C$_3$)alkylene]$_p$ then p is not zero;

W is selected from the group consisting of —O—, —S—, —S(O)—, —S(O)$_2$— and —NR$^1$— where R$^1$ is as defined above;

X is selected from the group consisting of >CH and >N such that the 5 membered ring defined by W, X and the pendant >CH groups is a heteroaryl ring;

Q is selected from the group consisting of a covalent bond, —O—, (C$_1$-C$_3$)alkylene, —C(O)—, —SO$_2$—, —NR$^1$C(O)NR$^1$—, —NR$^1$C(O)—, —C(O)NR$^1$—, —(C$_1$-C$_3$-alkylene)$_p$NR$^1$— and —NR$^1$—(C$_1$-C$_3$-alkylene)$_p$ where R$^1$ is hydrogen or alkyl and p is zero or one, provided that Q is not attached to X or W when W is —O—, —S—, —S(O)—, —S(O)$_2$— and further provided that when Q is —NR$^1$— then Q is attached to a carbon atom of the ring defined by A above;

L is selected from the group consisting of a covalent bond, alkylene, substituted alkylene, alkenylene, substituted alkenylene, cycloalkylene, and substituted cycloalkylene provided that L is attached to a carbon atom of the 5 membered heteroaryl group;

the cyclic structure defined by B, together with the unsaturation in the heteroaryl ring, is selected from the group consisting of cycloalkenyl, substituted cycloalkenyl, aryl, substituted aryl, heteroaryl, substituted heteroaryl, unsaturated heterocyclic and substituted unsaturated heterocyclic; and and tautomers, isomers, prodrugs, and pharmaceutically acceptable salts thereof.

Particularly preferred compounds of formula VI include those of formula VII:

where n, z, R, R$^3$, L, Q, T, and X are as defined above as well as tautomers, isomers, prodrugs, and pharmaceutically acceptable salts thereof.

In one of its pharmaceutical composition aspect, this invention is directed to a pharmaceutical composition comprising an effective amount of a compound according to any of formulas I-VII and a pharmaceutically inert carrier.

In another of its pharmaceutical aspects, this invention is directed to pharmaceutical compositions comprising an effective amount of a compound according to any of formulas I-VII, an effective amount of at least one anti-cancer agent, and a pharmaceutically inert carrier.

In one of its method aspects, this invention is directed to a method for inhibiting a proliferative disorder in a mammalian patient which method comprises administering to said patient a pharmaceutical composition comprising a pharmaceutically acceptable carrier and a therapeutically effective amount of a compound of formula I-VII or a mixture thereof.

In another of its method aspects, this invention is directed to a method for inhibiting a proliferative disorder in a mammalian patient which method comprises administering to said patient a pharmaceutical composition comprising a pharmaceutically acceptable carrier, an effective amount of at least one anti-cancer agent, and a therapeutically effective amount of a compound of formula I-VII or a mixture thereof.

In yet another of its method aspects, this invention is directed to a method for inhibiting a proliferative disorder in a mammalian patient which method comprises administering to said patient a pharmaceutical composition comprising a pharmaceutically acceptable carrier and a therapeutically effective amount of a compound of formula I-VII or a mixture thereof in combination with at least one anti-cancer agent.

For the treatment of the above conditions, the compounds of the invention may be advantageously employed in combination with one or more other medicinal agents, more particularly, with other anti-cancer agents. Examples of anti-cancer agents are: platinum coordination compounds for example cisplatin, carboplatin or oxalyplatin; taxane compounds for example paclitaxel or docetaxel; topoisomerase I inhibitors such as camptothecin compounds for example irinotecan or topotecan; topoisomerase II inhibitors such as anti-tumour podophyllotoxin derivatives for example etoposide or teniposide; anti-tumour vinca alkaloids for example vinblastine, vincristine or vinorelbine; anti-tumor nucleoside derivatives for example 5-fluorouracil, gemcitabine or capecitabine; alkylating agents such as nitrogen mustard or nitrosourea for example cyclophosphamide, chlorambucil, carmustine or lomustine; anti-tumour anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; or other HDAC inhibitors.

Preferred compounds of this invention include those found in the Tables below:

TABLE I

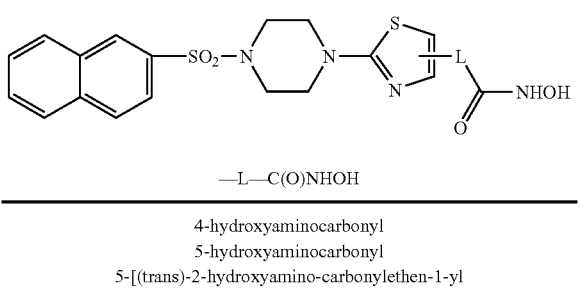

| —L—C(O)NHOH |
|---|
| 4-hydroxyaminocarbonyl |
| 5-hydroxyaminocarbonyl |
| 5-[(trans)-2-hydroxyamino-carbonylethen-1-yl] |

TABLE II

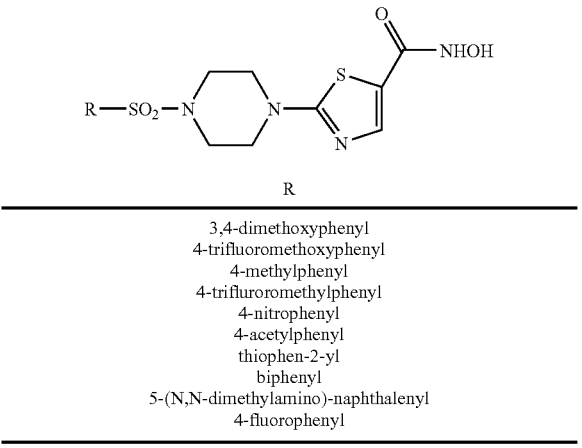

| R |
|---|
| 3,4-dimethoxyphenyl |
| 4-trifluoromethoxyphenyl |
| 4-methylphenyl |
| 4-trifluroromethylphenyl |
| 4-nitrophenyl |
| 4-acetylphenyl |
| thiophen-2-yl |
| biphenyl |
| 5-(N,N-dimethylamino)-naphthalenyl |
| 4-fluorophenyl |

TABLE III

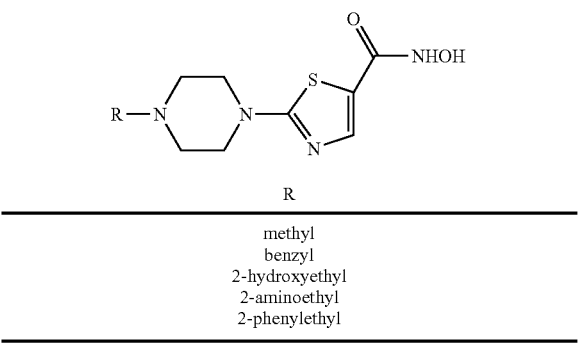

| R |
|---|
| methyl |
| benzyl |
| 2-hydroxyethyl |
| 2-aminoethyl |
| 2-phenylethyl |

TABLE IV

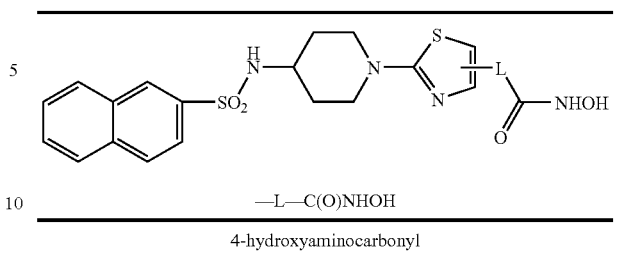

| —L—C(O)NHOH |
|---|
| 4-hydroxyaminocarbonyl |

TABLE V

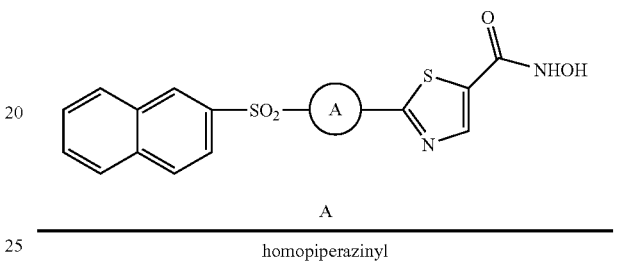

| A |
|---|
| homopiperazinyl |

TABLE VI

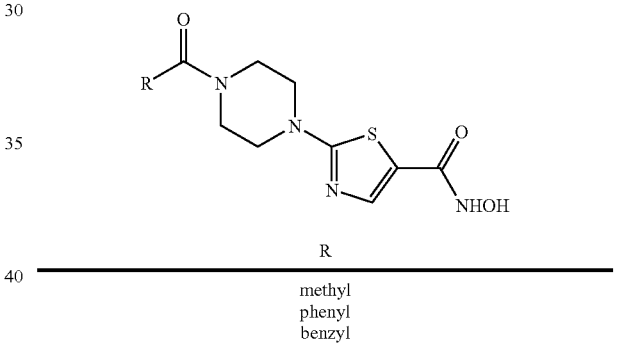

| R |
|---|
| methyl |
| phenyl |
| benzyl |

TABLE VII

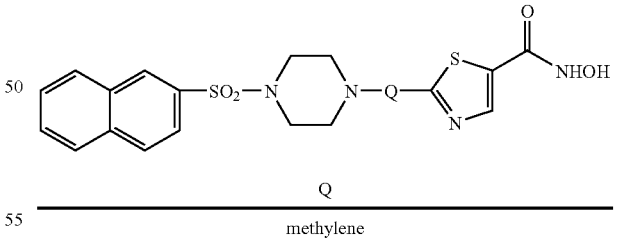

| Q |
|---|
| methylene |

Particularly preferred compounds include the following compounds and pharmaceutically acceptable salts thereof:

1-(2-naphthylsulfonyl)-4-(5-hydroxyaminocarbonylthiazol-2-yl)piperazine;

1-(2-naphthylsulfonyl)-4-(5-hydroxyaminocarbonylthiazol-2-yl)-1,4-diazepane;

1-(2-naphthylsulfonyl)-4-(4-hydroxyaminocarbonylthiazol-2-yl)piperazine;

1-(2-naphthylsulfonyl)-4-[5-(2-hydroxyaminocarbonylethen-1(E)-yl-thiazol-2-yl)piperazine;

1-(phenylsulfonyl)-4-[(5-(2-hydroxyaminocarbonylethen-1(E)-yl-thiazol-2-yl)piperazine;
1-(3,4-dimethoxyphenylsulfonyl)-4-[(5-(2-hydroxyaminocarbonylethen-1(E)-yl-thiazol-2-yl)piperazine;
1-(4-methoxyphenylsulfonyl)-4-[(5-(2-hydroxyaminocarbonylethen-1(E)-yl-thiazol-2-yl)piperazine;
1-(4-trifluoromethoxyphenylsulfonyl)-4-[(5-(2-hydroxyaminocarbonylethen-1(E)-yl-thiazol-2-yl)piperazine;
1-(4-methylphenylsulfonyl)-4-[(5-(2-hydroxyaminocarbonylethen-1(E)-yl-thiazol-2-yl)piperazine;
1-(4-trifluoromethylphenylsulfonyl)-4-[(5-(2-hydroxyaminocarbonylethen-1(E)-yl-thiazol-2-yl)piperazine;
1-(4-nitrophenylsulfonyl)-4-[(5-(2-hydroxyaminocarbonylethen-1(E)-yl-thiazol-2-yl)piperazine;
1-(thien-2-ylsulfonyl)-4-[(5-(2-hydroxyaminocarbonylethen-1(E)-yl-thiazol-2-yl)piperazine;
1-(1,1'biphenylsulfonyl)-4-[(5-(2-hydroxyaminocarbonylethen-1(E)-yl-thiazol-2-yl)piperazine;
1-(5-dimethylamino-naphthalene-1-sulfonyl)-4-[(5-(2-hydroxyaminocarbonylethen-1(E)-yl-thiazol-2-yl)piperazine;
1-(4-fluorophenylsulfonyl)-4-[(5-(2-hydroxyaminocarbonylethen-1(E)-yl-thiazol-2-yl)piperazine;
4-(2-naphthylsulfonylamino)-1-[(5-(2-hydroxyaminocarbonyl-thiazol-2-yl)-piperadine;
4-(1,1'-biphenylsulfonylamino)-1-[(5-(2-hydroxyaminocarbonyl-thiazol-2-yl)-piperadine;
4-(3,4-dimethoxyphenylsulfonylamino)-1-[(5-(2-hydroxyaminocarbonyl-thiazol-2-yl)-piperadine;
4-(4-methylphenylsulfonylamino)-1-[(5-(2-hydroxyaminocarbonyl-thiazol-2-yl)-piperadine;
2-(4-{[(1,1'-biphenylsulfonyl)amino]methyl}piperidin-1-yl)-1,3-thiazole-5-carboxylic acid hydroxyamide;
2-{[1-(2-naphthylsulfonyl)piperidin-4-yl]amino}-1,3-thiazole-5-carboxylic acid hydroxyamide;
2-(6-{[(4-methylphenyl)sulfonyl]amino}-3-azabicyclo[3.1.0]hex-3-yl)-1,3-thiazole-5-carboxylic acid hydroxyamide;
2-[3-[(4-methylphenyl)sulfonyl]tetrahydropyrimidin-1(2H)-yl]-1,3-thiazole-5-carboxylic acid hydroxylamide;
2-[4-(3,4-dimethoxy-benzene sulfonyl)-piperazin-1-yl]-thiazole-5-carboxylic acid hydroxyamide;
2-[4-(4-trifluoromethoxy-benzene sulfonyl)-piperazin-1-yl]-thiazole-5-carboxylic acid hydroxyamide;
2-[4-(4 toluene-4-sulfonyl)-piperazin-1-yl]-thiazole-5-carboxylic acid hydroxyamide;
2-[4-(4-trifluoromethyl-benzenesulfonyl)-piperazin-1-yl]-thiazole-5-carboxylic acid hydroxyamide;
2-[4-(4-nitro-benzenesulfonyl)-piperazin-1-yl]-thiazole-5-carboxylic acid hydroxyamide;
2-[4-(4-acetyl-benzenesulfonyl)-piperazin-1-yl]-thiazole-5-carboxylic acid hydroxyamide;
2-[4-(thiophene-2-benzenesulfonyl)-piperazin-1-yl]-thiazole-5-carboxylic acid hydroxyamide;
2-[4-(biphenyl-4-sulfonyl)-piperazin-1-yl]-thiazole-5-carboxylic acid hydroxyamide;
2-[4-(5-dimethylamino-naphthalene-1-sulfonyl)-piperazin-1-yl]-thiazole-5-carboxylic acid hydroxyamide;
2-[4-(4-fluoro-benzenesulfonyl)-piperazin-1-yl]-thiazole-5-carboxylic acid hydroxyamide;
2-(4-methyl-piperazin-1-yl)-thiazole-5-carboxylic acid hydroxyamide;
2-(4-Benzyl-piperazin-1-yl)-thiazole-5-carboxylic acid hydroxyamide (16b-hydroxamate);
2-(4-(2-hydroxyethyl)-piperazin-1-yl)-thiazole-5-carboxylic acid hydroxyamide;
2-(4-(2-aminoethyl)-piperazin-1-yl)-thiazole-5-carboxylic acid hydroxyamide;
2-(4-phenylethyl-piperazin-1-yl)-thiazole-5-carboxylic acid hydroxyamide;
2-(4-(2-oxo-2-phenylethyl)-piperazin-1-yl)-1,3-thiazole-5-carboxylic acid hydroxyamide;
2-(4-acetyl-piperazin-1-yl)-thiazole-5-carboxylic acid hydroxamide;
2-(4-benzoyl-piperazin-1-yl)-thiazole-5-carboxylic acid hydroxamide;
2-(4-phenylacetyl-piperazin-1-yl)-thiazole-5-carboxylic acid hydroxamide;
2-[4-(3-{1H-indol-3-yl}propanoyl)-piperazin-1-yl]-1,3-thiazole-5-carboxylic acid hydroxyamide;
N-(2-naphthylsulfonyl)-N'-{2-[5-(N-hydroxycarboxamido)]thiazolyl}-piperazine;
2-[1-(1,1'-biphenyl-4-ylsulfonyl)piperidin-4-yl]-1,3-thiazole-5-carboxylic acid hydroxyamide;
and pharmaceutically acceptable salts, isomers, tautomers, and prodrugs thereof.

DETAILED DESCRIPTION OF THE INVENTION

As noted above, this invention is directed to compounds, pharmaceutical compositions and methods for inhibiting histone deacetylase (HDAC) enzymatic activity. However, prior to describing this invention in more detail, the following terms will first be defined.

Definitions

Unless otherwise limited by a specific recitation herein, the following terms have the following meanings;

"Alkyl" refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to a monovalent alkyl group having from 1 to 3, and preferably 1 to 2, substituents selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkylene" refers to divalent alkylene groups having from 1 to 10 carbon atoms, preferably from 1 to 5 carbon atoms and more preferably 1 to 3 carbon atoms. This term is exemplified by groups such as methylene, ethylene, n-propylene (1,3-propylene), iso-propylene (1,2-propylene), n-butylene (1,4-butylene), n-pentylene (1,5-pentylene), and the like.

"Substituted alkylene" refers to a divalent alkylene group having from 1 to 3, and preferably 1 to 2, substituents selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkoxy" refers to the group "alkyl-O-" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O-".

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Acylamino" refers to the group —C(O)NR$^{10}$R$^{10}$ where each R$^{10}$ is independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where each R$^{10}$ is joined to form together with the nitrogen atom a heterocyclic or substituted heterocyclic ring.

"Alkenyl" refers to a monovalent alkenyl group having from 2 to 6 carbon atoms and more preferably 2 to 4 carbon atoms and having at least 1 and preferably from 1-2 sites of alkenyl unsaturation. The term "alkenyl" encompasses any and all combinations of cis and trans isomers arising from the presence of unsaturation.

"Substituted alkenyl" refers to alkenyl groups having from 1 to 3 substituents, and preferably 1 to 2 substituents, selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl substituted cycloalkyl, heteroaryl, substituted heteroaryl, heterocyclic, and substituted heterocyclic provided that any hydroxyl substitution is not on a vinyl carbon atom.

"Alkenylene" refers to a divalent alkenyl group having from 2 to 6 carbon atoms and more preferably 2 to 4 carbon atoms and having at least 1 and preferably from 1-2 sites of alkenyl unsaturation. The term "alkenylene" encompasses any and all combinations of cis and trans isomers arising from the presence of unsaturation.

"Substituted alkenylene" refers to alkenylene groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not on a vinyl carbon atom.

"Amino" refers to the group —NH$_2$.

"Substituted amino" refers to the group-NR'R" where R' and R" are independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heticylic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino.

"Aminoacyl" refers to the groups —NR$^{11}$C(O)alkyl, —NR$^{11}$C(O)substituted alkyl, —NR$^{11}$C(O)cycloalkyl, —NR$^{11}$C(O)substituted cycloalkyl, —NR$^{11}$C(O)alkenyl, —NR$^{11}$C(O)substituted alkenyl, —NR$^{11}$C(O)aryl, —NR$^{11}$C(O)substituted aryl, —NR$^{11}$C(O)heteroaryl, —NR$^{11}$C(O)substituted heteroaryl, —NR$^{11}$C(O)heterocyclic, and —NR$^{11}$C(O)substituted heterocyclic where R$^{11}$ is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is to an aromatic ring atom. Preferred aryls include phenyl and naphthyl, e.g, 2-naphthyl.

"Substituted aryl" refers to aryl groups which are substituted with from 1 to 3 substituents, and preferably 1 to 2 substituents, selected from the group consisting of hydroxy, acyl, acylamino, alkyl, substituted alkyl, alkoxy, substituted alkoxy, alkenyl, substituted alkenyl, amino, substituted amino, aminoacyl, aryl, substituted aryl, aryloxy, substituted aryloxy, cycloalkoxy, substituted cycloalkoxy, carboxyl, carboxyl esters, cyano, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or pharmaceutically acceptable salts thereof.

"Carboxyl esters" refers to the groups —C(O)O-alkyl, —C(O)O-substituted alkyl, —C(O)Oaryl, and —C(O)O-substituted aryl wherein alkyl, substituted alkyl, aryl and substituted aryl are as defined herein.

"Cycloalkyl" refers to monovalent cyclic alkyl groups of from 3 to 10 carbon atoms having single or multiple condensed rings which condensed rings may or may not be cycloalkyl provided that the point of attachment is to a cycloalkyl ring atom. Examples of cycloalkyl groups include, by way of example, adamantyl, cyclopropyl, cyclobutyl, cyclopentyl, cyclooctyl and the like.

"Substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkenyl" refers to monovalent cyclic alkenyl groups of from 4 to 10 carbon atoms, preferably 5 to 8 carbon atoms, having single or multiple condensed rings which condensed rings may or may not be cycloalkenyl provided that the point of attachment is to a cycloalkenyl ring atom. Examples of cycloalkenyl groups include, by way of example, cyclopenten-4-yl, cycloocten-5-yl and the like.

"Substituted cycloalkenyl" refers to a cycloalkenyl group, having from 1 to 5 substituents selected from the group consisting of oxo (=O), thioxo (=S), alkyl, substituted alkyl, alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not on an ethylenic carbon atom.

"Cycloalkylene" refers to divalent cyclic alkyl groups of from 3 to 10 carbon atoms having single or multiple condensed rings which condensed rings may or may not be cycloalkyl provided that the points of attachment are to cycloalkyl ring atoms. Cycloalkylene rings include, by way of example, cyclopropylene, 1,2-cyclobutylene, 1,3-cyclopentylene, 1,4-cyclooctylene, and the like. Cycloalkylene includes all cis and trans isomers encompassed by the particular cycloalkylene group.

"Substituted cycloalkylene" refers to a cycloalkylene group, having from 1 to 5 substituents selected from the group consisting of oxo (=O), thioxo (=S), alkyl, substituted alkyl, alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to a monovalent aromatic group of from 1 to 15 carbon atoms, preferably from 1 to 10 carbon atoms, and 1 to 4 heteroatoms selected from the group consisting of oxygen, nitrogen, —S—, —SO—, and —SO$_2$— within the ring. Such heteroaryl groups can have a single ring (e.g., pyridyl or furyl) or multiple condensed rings (e.g., indolizinyl or benzothienyl) provided that the point of attachment is through a heteroaryl ring atom. Preferred heteroaryls include pyridyl, pyrrolyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" refers to a monovalent saturated or unsaturated group having a single ring or multiple rings, including fused rings, spiro rings, bicyclic rings, and rings connected by an "exo single bond," from 1 to 10 carbon atoms and from 1 to 4 hetero atoms selected from the group consisting of nitrogen, sulfur, —S(O)—, —S(O)$_2$—, or oxygen within the ring wherein, in fused ring systems, one or more the rings can be aryl or heteroaryl provided that the point of attachment is to a heterocyclic (non-aromatic) ring atom. In addition one or more carbon atoms within the ring may contain an oxo (=O) or a thioxo (=S) group.

"Exo-single bond" refers to a bond between two heterocycle or heterocyclic rings, as exemplified as follows, wherein the bond between A and B is an exo-single bond:

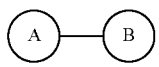

"Heterocyclene" refers to a divalent saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclene" refers to heterocyclene groups that are substituted with from 1 to 3 of the same substituents as defined for substituted cycloalkylene.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydro-benzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

The term "cyclo" refers to an cycloalkyl ring of from 3 to 7 carbon atoms. The "cyclo" ring may optionally contain 1 or 2 points of unsaturation within the ring and the ring is optionally substituted with from about 1 to about 3 substituents selected from the group consisting of alkyl, substituted alkyl, cycloalkyl, substituted cycloalkyl, heterocyclic, substituted heterocyclic, aryl, substituted aryl, heteroaryl, substituted heteroaryl, and the like. The cycloalkyl ring may also have one or two of the carbon atoms in the ring replaced by a >C=O or by >C=S moiety.

The term "het" refers to a heterocyclic ring of from 3 to 7 carbon atoms and from 1 to 4 hetero atoms selected from N, O and S. The heterocyclic ring may optionally contain 1 or 2 points of unsaturation within the ring and the ring is optionally substituted with from about 1 to about 3 substituents selected from the group consisting of alkyl, substituted alkyl, cycloalkyl, substituted cycloalkyl, heterocyclic, substituted heterocyclic, aryl, substituted aryl, heteroaryl, substituted heteroaryl, and the like. The heterocyclic ring may also have one or two of the carbon atoms in the ring replaced by a >C=O or by >C=S moiety.

The terms "-het-(L$^2$)$_b$-het-", "-het-(L$^2$)$_b$-cyclo-", "-cyclo-(L$^2$)$_b$-het-" and "-cyclo-(L$^2$)$_b$-cyclo-" refer to any combinations of "het" and "cyclo" groups linked together by a linker (when b is 1) selected from the group consisting of a bond, alkylene, substituted alkylene, alkenylene, and substituted alkenylene, cycloalkylene, and substituted cycloalkylene. When b is 0, the combinations of het and cyclo include multicyclic groups (of from 1 to 3 rings) wherein the rings may be fused multicyclic rings, or spirocyclic rings.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Tautomers" refers to structures which are art recognized to be in equilibrium with the depicted structure. For example, 1,2,4-imidazole has the following tautomeric structures:

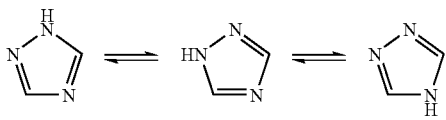

all of which are art recognized.

The term "platinum coordination compound" is used herein to denote any tumor cell growth inhibiting platinum coordination compound which provides platinum in the form of an ion.

The term "taxane compounds" indicates a class of compounds having the taxane ring system and related to or derived form extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has similar mechanism of action which involves the introduction of DNA strand breaks of the formation of free radicals.

The term "camptothecin compounds" is used to indicate compounds that are related to or derived from the parent camptothecin compound which is water-insoluble alkaloid derived from the Chinese tree Camptothecin acuminate and the Indian tree Nothapodytes foetida.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (Vinca rosea).

The term "alkylating agents" encompass a divers group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus Strep. peuticus var. caesius and their derivatives, characterized by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is highly purified recombinant DNA-derived humanized monoclonal IgG1 kappa antibody that binds with high affinity and specificity to the extracellular domain of the HER2 receptor.

Many breast cancers have estrogen receptors and growth of these tumors can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, inhibiting its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promoters of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Still further, some of the compounds defined herein include vinyl groups which can exist in cis, trans or a mixture of cis and trans forms. All combinations being within the scope of this invention.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4$^{th}$ Edition), and Larock's Comprehensive Organic Transformations (VCH Publishers Inc., 1989).

As to the synthesis of compounds of this invention, Scheme 1 below illustrates a general method for synthesis wherein L is a covalent bond, X is N and Y is CH, and the ring defined by A contains two ring amino groups.

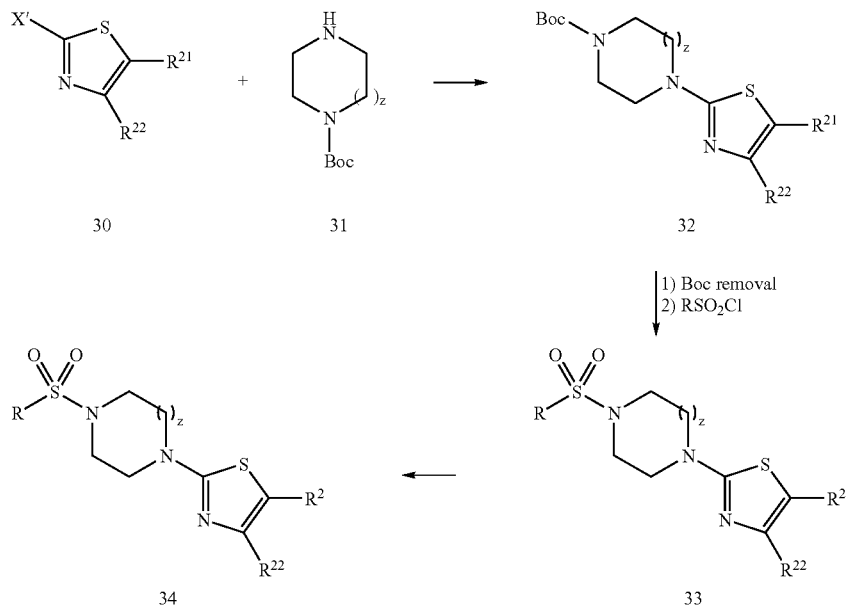

Scheme 1 where X' is a halogen such as bromo or chloro, one of $R^{21}$ and $R^{22}$ is —C(O)OPg where Pg is a carboxyl protecting group such as an alkyl group, e.g., methyl and the other is hydrogen, and R, $R^2$ and z are as defined above. For illustrative purposes in the discussion below, z will be assigned the value 1, $R^{21}$ will be carboxy methyl ester (—COOCH$_3$), and $R^{22}$ will be hydrogen. It is understood, of course, that other diaminoheterocycles such as where z is zero or one and other thiazole compounds can similarly be employed.

Specifically, commercially available methyl 2-halo-5-carboxylthiazole, compound 30, is condensed with at least an equivalent and preferably and excess of mono-protected 1-t-butoxycarbonyl (Boc) piperazine, compound 31, under conventional conditions to provide for methyl 2-[(1-t-butoxycarbonyl)piperazin-4-yl]-5-carboxylthiazole, compound 32. The reaction is typically conducted in an inert solvent such as acetonitrile, chloroform, and the like in the presence of a suitable base such as potassium carbonate which scavenges the acid generated during the reaction. The reaction is typically conducted at an elevated temperature of from about 40° to 100° C. for a period of time sufficient for substantial completion of the reaction which typically occurs within about 2 to 48 hours. The resulting product, compound 32, can be recovered by conventional methods, such as chromatography, filtration, crystallization, evaporation and the like or, alternatively, used in the next step without purification and/or isolation.

Conventional deprotection of the Boc-protected amino group (e.g., TFA) of methyl 2-[(1-t-butoxycarbonyl)piperazin-4-yl]-5-carboxylthiazole, compound 32, provides for the corresponding methyl 2-(piperazin-4-yl)-5-carboxylthiazole, not shown, which is then reacted with a suitable sulfonyl chloride (RSO$_2$Cl) to provide for the corresponding sulfonyl amide, compound 33. This latter reaction is typically conducted by combining preferably from about 1.5 to about 2.5 equivalents, of the sulfonyl chloride in an inert diluent such as dichloromethane and the like. Generally, the reaction is conducted at a temperature ranging from about 0° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like, as the base. Upon completion of the reaction, the resulting N-sulfonyl amino acid, compound 33 is recovered by conventional methods including neutralization, extraction, precipitation, chromatography, filtration, evaporation and the like.

The sulfonyl chlorides employed in the above reaction are either known compounds or compounds that can be prepared from known compounds by conventional synthetic procedures. Such compounds are typically prepared from the corresponding sulfonic acid, i.e., from compounds of the formula RSO$_3$H where R is as defined above, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0 to about 80° C. for about 1 to about 48 hours to afford the sulfonyl chloride. Alternatively, the sulfonyl chlorides can be prepared from the corresponding thiol compound, i.e., from compounds of the formula R-SH where R is as defined herein, by treating the thiol with chlorine (Cl$_2$) and water under conventional reaction conditions.

Examples of sulfonyl chlorides suitable for use in this invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, 2-methylphenylsulfonyl chloride, 4-acetamidobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethyl-benzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl amino acids.

The R$^{21}$ methyl carboxyl group of compound 33 can then be converted to a variety of amides including hydroxyamides by reaction with a 2-20 fold excess of a suitable amine such as hydroxylamine. The reaction is typically conducted in a suitable diluent such as a 5:2 mixture of methanol to water under basic conditions, e.g, the addition of sodium hydroxide. The reaction is typically conducted at a temperature of from about −20° to 20° C. for a period of time sufficient for substantial completion of the reaction which typically occurs within about 0.5 to 10 hours. The resulting amide, compound 34, can be recovered by conventional methods, such as chromatography, filtration, crystallization, evaporation and the like.

Alternatively, ester 33 is converted to the hydroxamic acid 34 as shown in Scheme 1B.

Scheme 1B

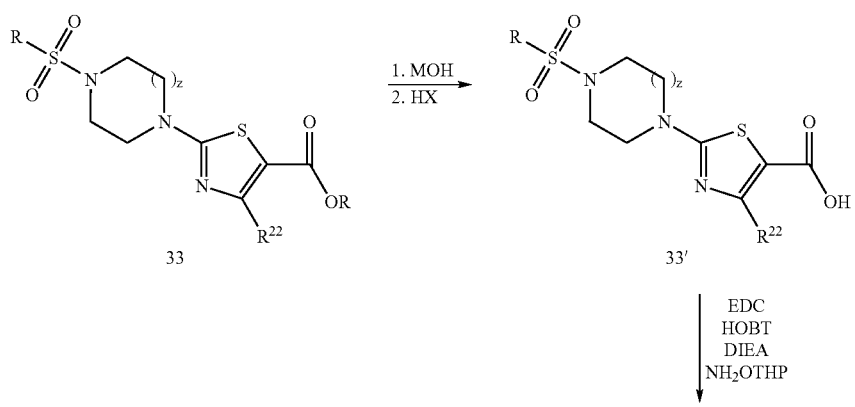

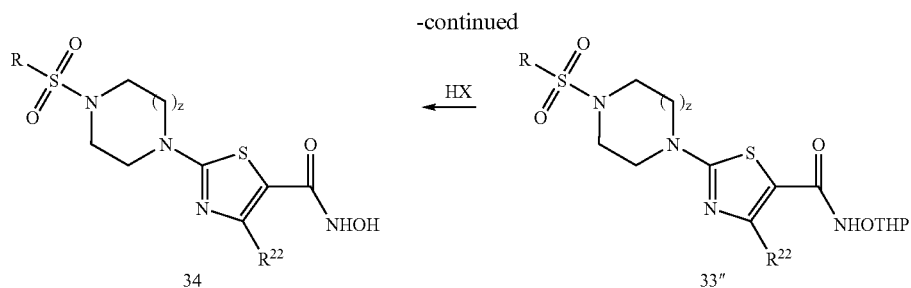

where HX is a strong acid and MOH is an alkali metal hydroxide.

The ester prepared by the methods of Scheme 1 is hydrolyzed to a carboxylic acid 33' with about 1-20 equivalents of an alkali metal hydroxide such as, but not limited to, sodium hydroxide or potassium hydroxide in a mixture of water and a suitable organic solvent in about one to 48 hours at about 20 to 100° C. Suitable organic solvents include, but are not limited to, tetrahydrofuran, ethanol, methanol, or dioxane. The reaction mixture is neutralized with an inorganic acid such as hydrochloric, hydrobromic, or sulfuric acid and the solvents are evaporated. The residue is suspended in a suitable solvent and treated with about one to five equivalents of a tertiary amine such as, but not limited to, triethylamine or diisopropylethylamine (DIEA), about one to five equivalents of N-hydroxybenzotriazole (HOBT), and about one to five equivalents of a carbodiimide coupling reagent such as, but not limited to, dicyclohexylcarbodiimide or 1-[3-(dimethylamino)propyl]-1-ethylcarbodiimide (EDC) and about one to five equivalents of O-(tetrahydro-2H-pyran-2-yl)hydroxylamine ($NH_2OTHP$) for about one to 48 hours at about 20 to 100° C. to produce a protected hydroxamic acid 33" A solution of about 1 to 50% strong acid such as, but not limited to, hydrochloric acid or trifluoroacetic acid in an organic solvent such as, but not limited to, dichloromethane, dichloroethane, methanol, ethanol, or dioxane at about 0° to 80° C. in about one minute to 24 hours converts 33" to the hydroxamic acid 34 that is recovered by the means previously described.

Scheme 1C shows the synthesis of compounds of formula I where T is a bond and where R, $R^2$, $R^{21}$, $R^{22}$, Boc, X' and z are as defined above.

Scheme 1C

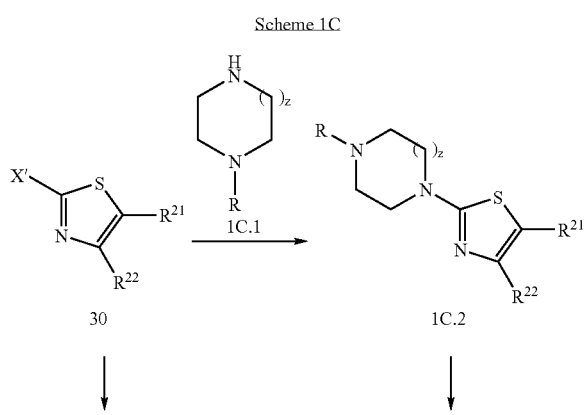

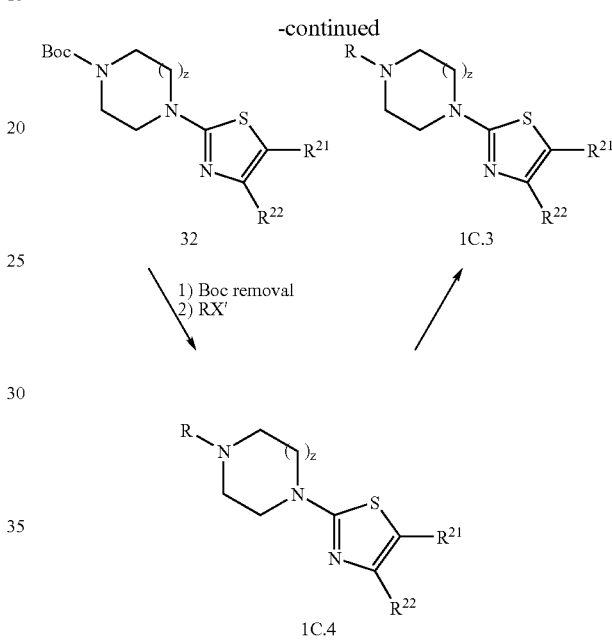

Specifically, commercially available methyl 2-halo-5-carboxylthiazole, compound 30, is condensed with at least an equivalent and preferably an excess of a mono-N-substituted piperazine 1C.1 under conventional conditions to provide for a methyl 2-[(1-substituted)piperazin-4-yl]-5-carboxylthiazole, 1C.2. The reaction is typically conducted in an inert solvent such as acetonitrile, chloroform, and the like in the presence of a suitable base such as potassium carbonate that scavenges the acid generated during the reaction. The reaction is typically conducted at an elevated temperature of from about 40° to 100° C. for a period of time sufficient for substantial completion of the reaction that typically occurs within about 2 to 48 hours. The resulting product, compound 1C.2, can be recovered by conventional methods, such as chromatography, filtration, crystallization, evaporation and the like or, alternatively, used in the next step without purification and/or isolation. The $R^{21}$ methyl carboxylate group of IC.2 is then converted to a variety of amides including hydroxyamides 1C.3 by any of the methods described for Scheme 1.

Alternatively, compound 32 in Scheme 1 is deprotected as described above and the secondary nitrogen of the piperazine ring of the resulting product is alkylated with about one to five equivalents of an alkyl or substituted alkyl halide in a suitable solvent at about 0 to 100° C. in the presence of about one to five equivalents of an alkali metal carbonate in about one to 72 hours. Suitable alkyl and substituted alkyl halides include chlorides, bromides, and iodides. Suitable solvents are, but are not limited to, methylene chloride, tetrahydrofuran, dioxane, and dimethylformamide. Preferred alkali metal carbonates are potassium and cesium carbonate. The resulting ester 1C.4 is converted to the desired amides such as 1C.3 by any of the methods described above.

Scheme 2 illustrates the synthesis of compounds of formula I where T is a carbonyl group.

as, but not limited to, EDCI or dicyclohexylcarbodiimide in the presence of about one to five equivalents of HOBT or HOAT and about one to five equivalents of a tertiary amine base such as, but not limited to, diisopropylethylamine or triethylamine in a suitable solvent such as tetrahydrofuran or methylene chloride at about 0 to 60° C. for about one to 72 hours. The resulting amide, compound 35, can be recovered by conventional methods, such as chromatography, filtration, crystallization, evaporation and the like. Conversion of the amide 35 to compound 36 proceeds in the manner described above.

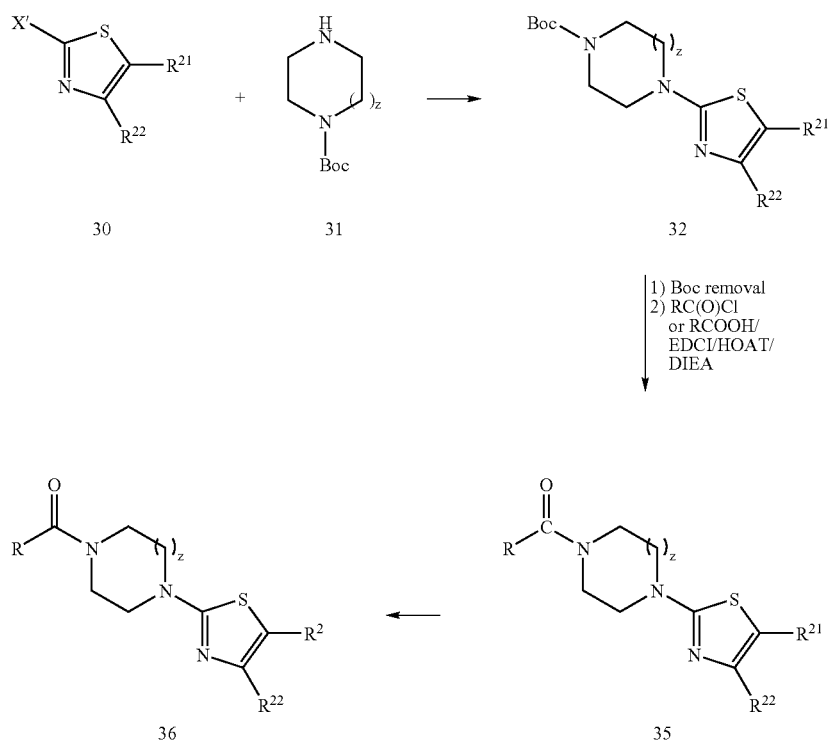

where R, $R^2$, $R^{21}$, $R^{22}$, Boc, X' and z are as defined above.

Specifically, in Scheme 2, compound 32 is prepared as per Scheme 1 above. Conventional removal of the Boc group provides for the free amino group on the piperazine ring (not shown). The amino group is then acylated by conventional means such as reaction with an excess of the acid chloride, RC(O)Cl, in a suitable inert diluent such as dichloromethane and preferably in the presence of an tertiary amine to scavenge the acid generated during the reaction. Alternatively, the free amine group of the piperazine is treated with about one to five equivalents of a carboxylic acid in the presence of a suitable carbodiimide coupling reagent such In Schemes 1 and 2, replacement of 4-Boc-piperazine with mono-amino protected diamino compounds provides for compounds of formula I such as those where Q is amino, T is a sulfonylamide, etc. Examples of commercially available diamino compounds include 1,4-diaminocyclohexane, 1,2-diaminocyclohexane, 4-aminopiperidine, 3-aminopiperidine, 3-aminopyrrolidine, 4-(aminomethyl)piperidine, 2-(aminomethyl)pyrrolidine, and the like. These compounds can be conventionally mono-amino protected to provide for suitable reagents for use in this invention.

Scheme 3 illustrates the synthesis of compounds of formula I where L is an alkenylene group.

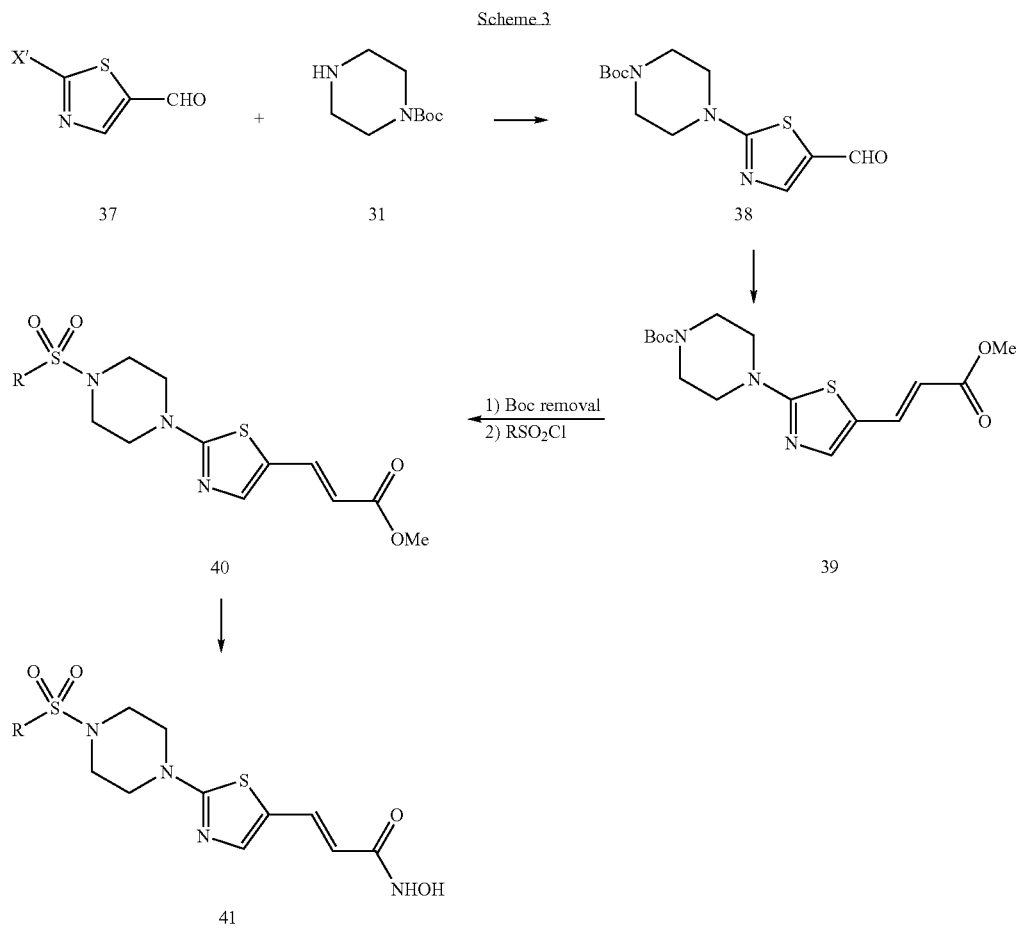

where X', R and Boc are as defined above.

Specifically, commercially available 2-bromo-5-formylthiazole, compound 37, is condensed with at least an equivalent and preferably and excess of mono-protected 1-t-butoxycarbonyl (Boc) piperazine, compound 31, as described above to provide for methyl 2-[(1-t-butoxycarbonyl)piperazin-4-yl]-5-formylthiazole, compound 38. Alternatively, 2-bromo-5-formylthiazole can be prepared from the 5-carboxyl precursor, compound 30 where $R^{21}$ is carboxyl or a carboxyl ester, by conventional reduction procedures.

Conversion of compound 38 to compound 39 proceeds via a conventional Wittig Horner reaction.

Removal of the Boc protecting group proceeds via conventional conditions to provide for the free amine, not shown, which is then contacted with an excess of sulfonyl chloride in the manner described above to provide for compound 40. Conversion of the methyl ester of compound 40 to the corresponding amide, e.g., hydroxylamide, proceeds via contacting the ester with an excess of amine in the manner described above thereby providing for compound 41.

In one alternative embodiment, commercially available 2-bromo-4-formylthiophene or 2-bromo-5-formylthiophene can be employed in the reactions recited above to provide for thiophene compounds the corresponding to thiazole compound 41.

In another alternative embodiment, the sulfonyl chloride, $RSO_2Cl$, can be replaced with an acid chloride, RC(O)Cl, to provide for compounds where T is carbonyl.

Still further, conventional oxidation of the sulfur in the thiophene or the thiazolyl to the corresponding sulfoxide or sulfone proceeds, for example, by contact with m-chloroperbenzoic acid.

In yet another embodiment, the vinylene group of compound 40 can be converted to a cyclopropylene moiety by conventional reaction with at least an equivalent and preferably an excess of diazomethane ($CH_2N_2$) in the presence of a palladium diacetate as shown in Scheme 3A below:

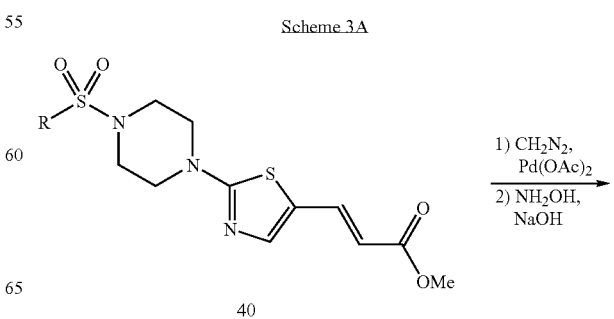

-continued

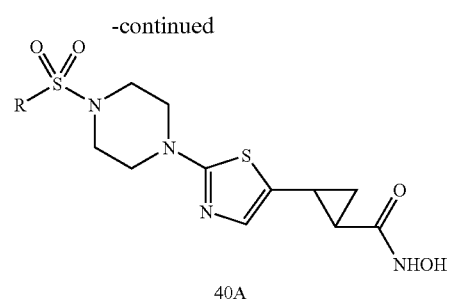

40A

Subsequent conversion of the carboxyl ester to the hydroxylamide proceeds as discussed above.

Scheme 4 illustrates the synthesis of compounds of formula I where Q is an alkylene group. For illustrative purposes, T is a sulfonyl group, the ring defined by A is a piperazine ring, and W is S, X is N and Y is CH.

precipitation, chromatography, filtration, evaporation and the like or, alternatively, is used in the next step without isolation and/or purification.

The amide of compound 43 is converted to the corresponding thioamide by conventional methods including reaction with $P_2S_5$ to provide for compound 44 which can be recovered by conventional methods including neutralization, extraction, precipitation, chromatography, filtration, evaporation and the like or, alternatively, is used in the next step without isolation and/or purification.

Compound 44 is converted to the corresponding thiazole derivative by reaction with methyl 2-chloro-2-formyl acetate, compound 45. In turn, this compound is prepared by reaction of methyl 2-chloroacetate and methyl formate in the presence of a suitable base. Cyclization provides for the 5-carboxylate (methyl ester) of the thiazole.

In scheme 4, the 5-carboxylate is converted to the corresponding hydroxylamide in the manner described above. It is understood, of course, that this carboxylate can be reduced

SCHEME 4

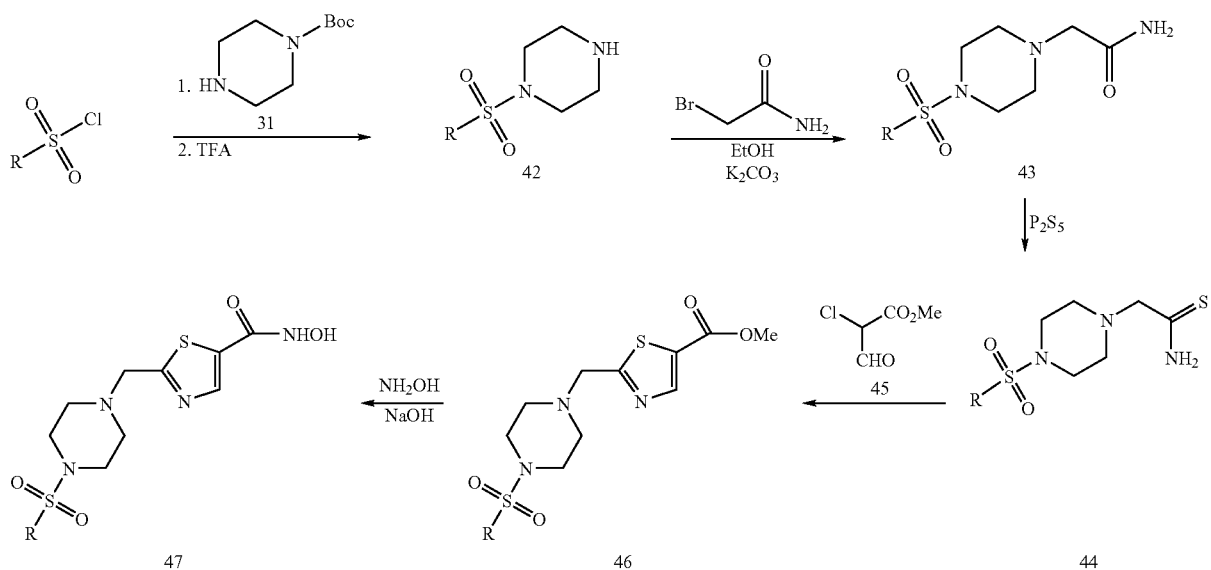

where R and Boc are as defined above.

Specifically, an excess of sulfonyl chloride, $RSO_2Cl$, is combined in the manner described above with 1-t-butoxycarbonylpiperazine, compound 31, to provide 4-($RSO_2$—)-1-t-butoxycarbonylpiperazine (not shown). Conventional removal of the Boc protecting group provides for 4-($RSO_2$—)-piperazine, compound 42.

Coupling of compound 42 with an ω-halocarboxylamide, illustrated by 2-bromoacetamide, provides for compound 43. This conventional coupling reaction is preferably conducted in an inert solvent such as methanol, ethanol, and the like preferably in the presence of a suitable base such as potassium carbonate to scavenge the acid generated during reaction. The reaction is preferably conducted at an elevated temperature of from about 50 to about 100° C. The reaction is continued until substantial completion which typically occurs within a period of from about 2 to 48 hours. Upon completion of the reaction, compound 34 is recovered by conventional methods including neutralization, extraction, to the corresponding formyl group via conventional reduction conditions well known in the art and then used in the manner of Scheme 3 to provide for the alkenylene linking group.

Compounds in Scheme 4 can be used to prepare similar compounds of formula I where T is a carbonyl group. For example, retention of the Boc protecting group throughout this reaction scheme allows for the synthesis of a Boc protected equivalent to compound 46. Removal of the Boc group followed by reaction with an acid chloride, RC(O)Cl, provides for a carbonyl equivalent of compound 46 which can then be converted to the corresponding N-hydroxylamide.

Scheme 4' shows the synthesis of compounds of formula I where Q is a carbon-carbon bond between the ring defined by A and V. For illustrative purposes, T is a sulfonyl group, the ring defined by A is a piperidine ring, and W is S, X is N and Y is CH.

Scheme 4'

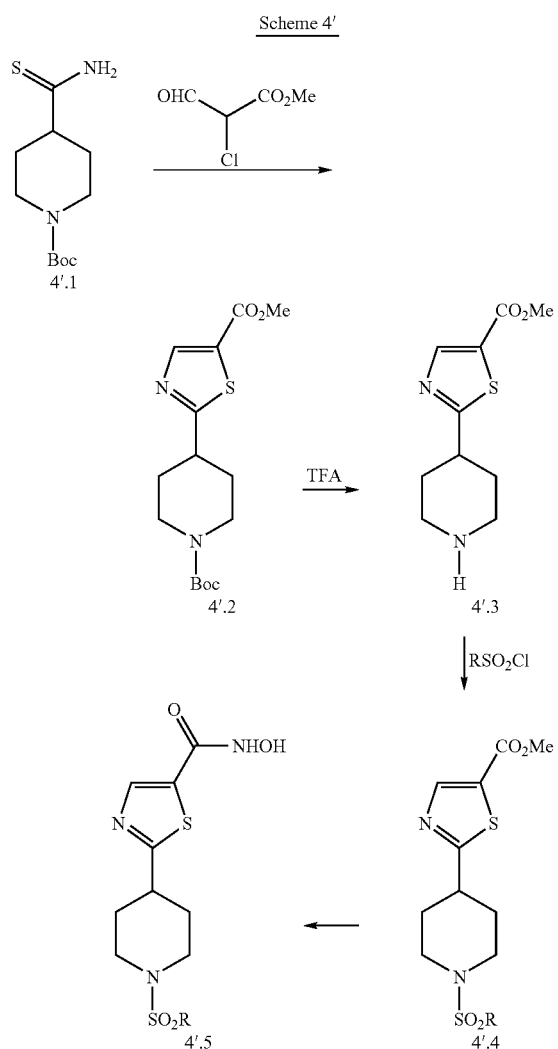

A Boc protected 4-(aminocarbothioyl)tetrahydropyridne-1(2H)carboxylate 4'.1 is treated with about one to 20 equivalents of methyl chloro(formyl)acetate in a suitable solvent at about 0 to 140° C. for about 30 minutes to 72 hours to give thiazole ester 4'.2. Suitable solvents include, but are not limited to, methylene chloride, toluene, dioxane, tetrahydrofuran, and dimethylformamide. The Boc group of 4'.2 is cleaved by any of the methods described above to give piperidine 4'.3. Piperidine 4'.3 is sulfonylated by any of the methods described above to give sulfonylated piperidine 4'.4. Sulfonylated piperidine 4'.4 is converted to hydroxamate 4'.5 by any of the methods described above.

Still further, other 5 membered heteroaryl ring systems for use in this invention can be readily prepared by conventional means as shown in Schemes 4A and 4B below:

Scheme 4A

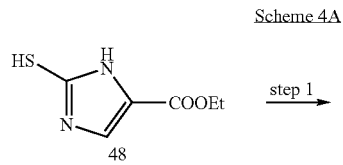

Specifically, in Scheme 4A, ethyl 2-thiol-5-carboxylimidazole compound 48, is converted to the corresponding methyl sulfone, compound 49, prepared by methylation using methyl iodide, followed by oxidation using metachloroperbenzoic acid. Subsequent re-esterification and reaction with piperazine provides for compound 50 which can be used in the procedures set forth above to provide for compounds of this invention. For example, conversion of the ethyl carboxylate to the formyl functionality proceeds via well documented reduction procedures. The formyl functionality can then be employed in a Wittig Horner reaction to provide for the vinylene carboxylate derivative in the manner described in Scheme 3 above.

Still further, Scheme 4B illustrates how commercially available 2-amino-5-carboxyl-1,3,4-triazole can be converted into intermediates which can be used in the above schemes for the synthesis of compounds of this invention.

SCHEME 4B

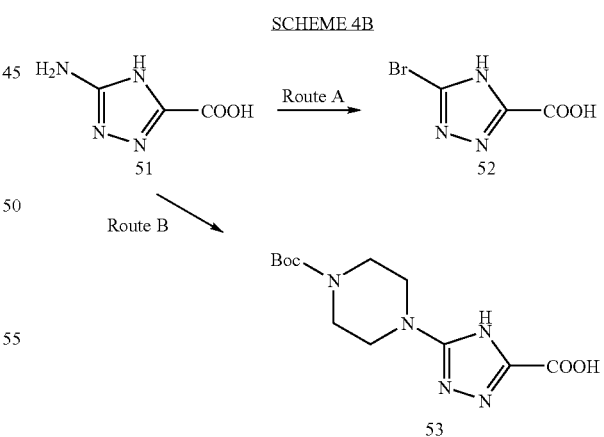

Compound 51 can be converted via conventional methods to the corresponding 2-bromo-5-carboxyl-1,3,4-triazole or the 2-(4-Boc-piperazin-1-yl)-5-carboxyl-1,3,4-triazole.

Still other heteroaryls useful in the synthetic schemes recited herein include the following commercially available compounds:

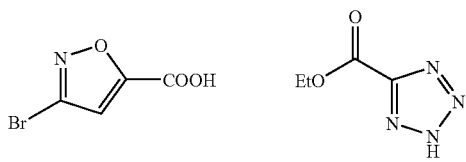

Compounds where Q is —SO$_2$—, V, Y and Z are carbon, X is S, W is O, and ring A is piperidine are prepared using methods described in T. Hamada et al. Synthesis, 1986, 852 and shown in Scheme 5 below. This preparation is also useful for any A ring containing a nitrogen atom that may be bound to the sulfonyl group.

Compound 63, is an intermediate that, after deprotection, can be converted to various analogs as exemplified herein.

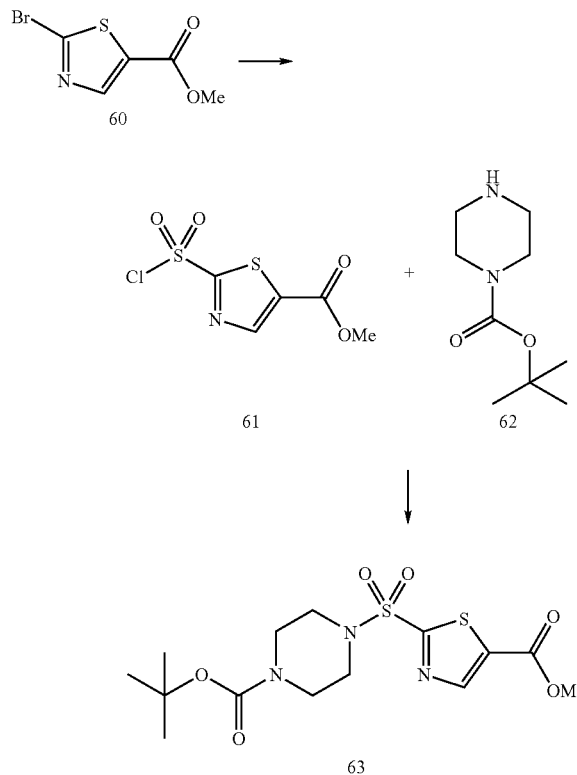

For example, compound 60 in Scheme 5 above can be converted to compound 61 by using the methods described in T. Hamada et al. Synthesis, 1986, 852. Coupling of the sulfonyl chloride, compound 61, with compound 62 is accomplished as discussed herein above (see for example Scheme 4).

In Scheme 6 below, compounds where Q is —O—, V, Y and Z are carbon, X is S, W is O, and ring A is piperidine are prepared using methods described herein and methods described in W. Huang et al. Biorg. Med. Chem. Lett. 2003, 13 (3) 561. This preparation is also useful for any A ring containing at least one carbon atom that may be bound to the oxygen linking the A ring to the 5-membered heteroaryl ring.

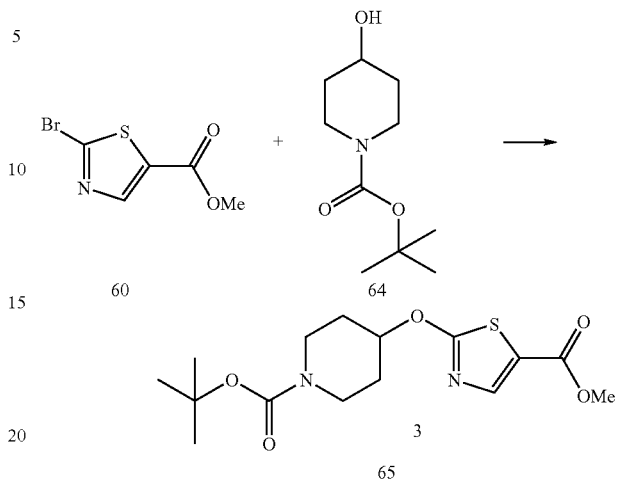

For example, compound 60 is reacted with compound 64 by reaction with triphenylphospine and DEAD in an inert solvent such as THF. Again, intermediate 65, after deprotection, can be converted to various analogs as exemplified herein.

Compounds where Q is —O—, V, Y and Z are carbon, X is S, W is C(O), and ring A is piperidine are prepared as discussed in Morimoto et al. J. med. Chem. 2001, 44 (21) 3369. This preparation is also useful for any A ring containing at least one carbon atom that may be bound to the carbonyl linking the A ring to the 5-membered heteroaryl ring.

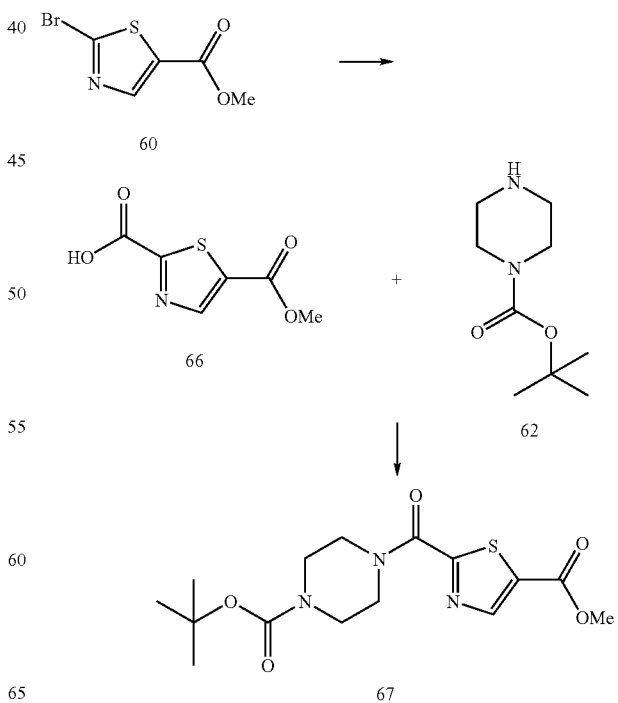

For Example, compound 60 is carboxylated with butyl lithium and carbon dioxide to form compound 66. Reaction of compound 66 with mono-protected piperazine in the presence of a coupling agent, such as DCC, affords compound 67, which after deprotection, can be converted to various analogs as exemplified herein.

PHARMACEUTICAL FORMULATIONS

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I-VII above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The compounds of the present invention may be administered to patients either alone or in combination with other known anti-tumor agents. When administered alone about 0.005 to about 100 mg/kg, more preferably about 0.005 to about 10 mg/kg, are administered to the patient Higher and lower dosages may be used. Administration may occur once a day, or several times in a day. In addition the treatment may be repeated every 7, 14, 21 or 28 days.

When administered in combination with other anti-cancer agents, the compounds of the present invention may be prepared in a formulation that includes both the compounds of Formula I-VII and one or more other anti-cancer agents. Alternatively the other anti-cancer agents may be administered in a separate formulation which may be administered before, after or simultaneously with the compounds of this invention. When administered in combination with at least one other anti-cancer agent, about 5 to about 100 mg/kg, more preferably about 0.005 to about 10 mg/kg, of the present HDAC inhibitors are administered to the patient. Higher and lower dosages may be used. The dosages of the other anti-cancer agents are known in the art. Administration may occur once a day, or several times in a day. In addition the treatment may be repeated every 7, 14, 21 or 28 days.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Lactose | 5 |
| Active Ingredient | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
| --- | --- |
| Active Ingredient | 250.0 mg |
| Isotonic saline | 1000 mL |

Formulation Example 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intraarterial infusion of hypertonic solutions which can transiently open the blood-brain barrier.

Utility

Deacetylases are found in transcriptional repression pathways. In addition, histone deacetylases (HDAC) play an important role in cell proliferation and differentiation. Inhibition of histone deacetylation results in cell cycle arrest, cellular differentiation, apoptosis and reversal of the transformed phenotype. Therefore, HDAC inhibitors are useful in the treatment and/or amelioration of cell proliferative diseases or conditions, such as cancers.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
| --- | --- |
| Boc | N-tert-butoxycarbonyl |
| d = | doublet |
| dd = | doublet of doublets |
| DCM = | dichloromethane |
| DMEM = | Delbaco's minimum eagle's medium |
| DMSO = | dimethylsulfoxide |
| DEAD = | Diethyl azodicarboxylate |
| DIEA = | diisopropylethylamine |
| EtOAc = | ethyl acetate |
| g = | grams |
| h = | hour |
| HOAT = | 1-hydroxy-7-azabenzotriazole |

| | |
|---|---|
| HOBT = | 1-hydroxybenzotriazole |
| HPLC = | high performance liquid chromatography |
| hr or h = | hour |
| L = | liter |
| m = | multiplet |
| M = | molar |
| Me = | methyl |
| min = | minutes |
| mg = | milligram |
| mL = | milliliter |
| mm = | millimeter |
| mM = | millimolar |
| mmol = | millimol |
| MHz = | megahertz |
| m/e or m/z = | mass to charge ratio from mass spectrum |
| N = | normal |
| nm = | nanometers |
| NMR = | nuclear magnetic resonance |
| PDA = | |
| q.s. = | means adding a quantity sufficient to achieve a certain state |
| RPHPLC | reverse phase high performance liquid chromatography |
| rt = | room temperature |
| Rt = | Retention time |
| s = | singlet |
| sec = | seconds |
| t = | triplet |
| TCA = | trichloroacetic acid |
| TFA = | trifluoroacetic acid |
| THF = | tetrahydrofuran |
| TLC or tlc = | thin layer chromatography |
| w/v = | weight to volume |
| v/v = | volume to volume |
| µL = | microliter |
| µM = | micromolar |

All the chemicals starting materials were obtained from commercial suppliers and used without further purification.

Flash column chromatography was performed with silica (60-120 mesh). Analytical RPHPLC was done using Shimadzu HPLC equipped with a PDA detector using the following columns and systems: a Thermo Hypersil BDS, 4.6×150 mm, 5 µM particle size, C-18 column, isocratic using acetonitrile:0.1% TFA in water (60:40), flow rate=0.5 mL/min (System-1); Thermo Hypersil BDS, 4.6×250 mm, 5 µM particle size, C-18 column, linear gradient A-acetonitrile: B-0.1% TFA in water; 0.01 min A(10%):B(90%); 5.00 min A(10%):B(90%); 15.00 min A(90%):B(10%); 20.00 min A(90%):B(10%); 25.00 min A(10%):B(90%); 30.00 min A(10%):B(90%); 30.00 min Stop; flow rate=1.5 mL/min (System-2).

1H NMR spectra were recorded at 200 or 300 MHz and the proton chemical shifts are expressed in ppm relative to internal tetramethylsilane and coupling constants (J) are expressed in hertz. Mass spectra were carried out using a Micromass model.

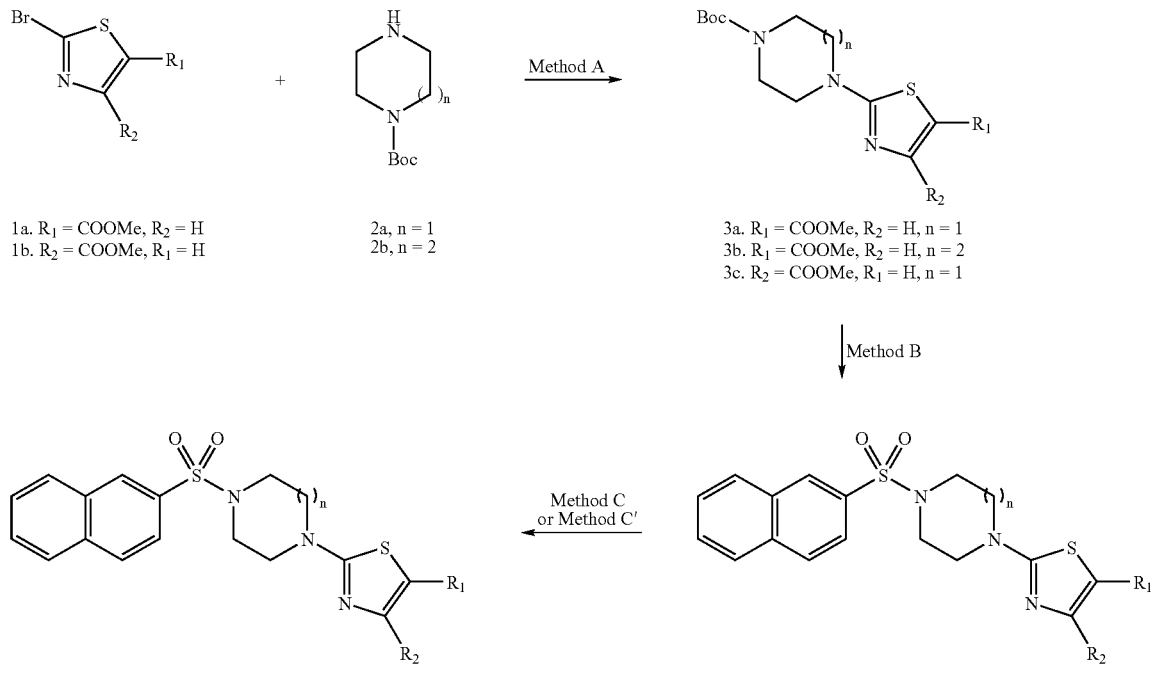

Scheme 5

1a. $R_1$ = COOMe, $R_2$ = H
1b. $R_2$ = COOMe, $R_1$ = H 2a, n = 1
2b, n = 2

3a. $R_1$ = COOMe, $R_2$ = H, n = 1
3b. $R_1$ = COOMe, $R_2$ = H, n = 2
3c. $R_2$ = COOMe, $R_1$ = H, n = 1

5a. $R_1$ = CONHOH, $R_2$ = H, n = 1
5b. $R_1$ = CONHOH, $R_2$ = H, n = 2
5c. $R_2$ = CONHOH, $R_1$ = H, n = 1
5d $R_1$ = CH=CHCO$_2$H, $R_2$ = H, n = 1
5e $R_1$ = CH=CHCONHOTHP, $R_2$ = H, n = 1
5f $R_1$ = CH=CHCONHOH, $R_2$ = H, n = 1

Method A

To bromothiazole 1 (1 g, 4.18 mmol) in acetonitrile (40 mL) was added potassium carbonate (1.32 g, 10 mmol) followed by N-Boc piperizine 2a (0.935 g, 5 mmol). The reaction mixture was held at 80° C. for 16 h. At the end of the reaction time, acetonitrile was removed on roto-evaporation and the residue was taken in ethyl acetate (50 mL) and washed with brine (30 mL). The crude product 3 obtained (1.4 g, 99%) on removal of solvent was taken as such for the next reaction.

Method B

To the crude product 3 obtained from general method A (1.4 g, 4.15 mmol) TFA (20%) in dichloromethane was added and stirred at room temperature for an h. After removing the solvent, the residue was kept under high vacuum for 1 h. The residue was then redissolved in DCM (20 mL) to which triethylamine (6.0 mL, 41.5 mmol) and 2-naphthalene sulfonyl chloride (1.85 g, 8.2 mmol) was added and stirred at room temperature over night. Subsequently more DCM (50 mL) was added and washed with 1N hydrochloric acid (20 mL). The crude product obtained on removal of solvent was purified on a column chromatography using ethyl acetate in hexanes (1:1) to obtain product 4 (1.15 g, %) as white crystalline solid.

Method C

To the product 4 (200 mg, 0.46 mmol) in methanol (5 mL), aqueous hydroxyl amine (30 μL, 4.60 mmol, 50% solution) and sodium hydroxide (118 mg, 3.22 mmol, 2 mL) in water (2 mL) was added and the reaction mixture was held at 0° C. for 4 hours. After acidification with 1N HCl, the solvent was removed and the residue was taken up in ethyl acetate and washed with brine. The product 5 obtained (100 mg) on removal of solvent was purified on a RPHPLC.

Method C'

To the product 4 (200 mg, 0.46 mmol) in methanol (5 mL) and dioxane (5 mL) was added potassium hydroxide (285 mg) and the mixture ws stirred at reflux temperature for 3 hours. The solvent was evaporated, the residue mixed with water, and the mixture acidified with 2N hydrochloric acid. The mixtue was extracted with ethyl acetate, the extracts were dried, and the solvent evaporated to give the carboxylic acid 5d (173 mg). To a solution of 5d (100 mg, 0.264 mmol) in dichloromethane (10 mL) were added EDCI.HCl (101.13 mg, 0.52 mmol), HOBT (35.64 mg, 0.26 mmol), DIPEA (68.18 mg, 0.527 mmol) and $NH_2OTHP$ (29.81 mg, 0.264 mmol) under $N_2$ atmosphere. The reaction mixture was stirred at room temperature for 12 h (progress of the reaction was monitored by TLC analysis). Water (10 mL) followed by dichloromethane (10 ml) were added to the reaction mixture and the organic layer was separated, dried over anhydrous sodium sulfate, filtered and concentrated under reduced pressure. The residue was purified by column chromatography using silica gel to obtain THP hydroxamate 5e (81 mg). To a solution of 5e (60 mg) in methanol (1 mL) was added 23% v/v HCl in ether (4 mL) at 0° C. The reaction mixture was stirred at 0° C. temperature for 15 min (progress of the reaction was monitored by TLC analysis). Solvent was completely removed and to the crude residue was added diethyl ether and filtered to give 5f as a solid (42 mg).

Example 1

Synthesis of 1-(2-naphthylsulfonyl)-4-(5-hydroxyaminocarbonylthiazol-2-yl)piperazine

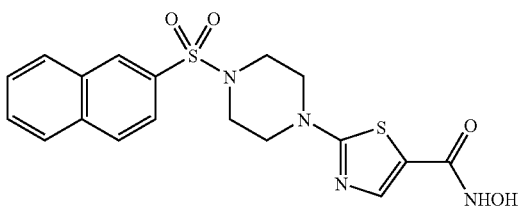

Intermediate 3a was obtained by the general Method A using methyl 2-bromothiazole-5-caboxylate 1a and N-Boc piperazine 2a. TLC (Rt): 0.41 (30% EtOAc in hexanes).

$^1$H NMR (300 MHz, $CDCl_3$) δ 7.76 (s, 1), 3.78 (s, 3), 3.66-3.69 (m, 4), 3.19-3.22 (m, 4), 1.49 (s, 9). MS (ES+): 328 (M+1).

Intermediate 4a was obtained by employing the general Method B using the intermediate 3a. TLC (Rt): 0.41 (30% EtOAc in hexanes).

$^1$H NMR (300 MHz, $CDCl_3$): δ 8.32 (d, J=1.5 Hz, 1H), 7.89-7.98 (m, 4H), 7.76 (s, 1H), 7.70-7.73 (dd, J=1.8, 8.4 Hz, 1H), 7.61-7.66 (m, 2H), 3.78 (s, 3H), 3.66-3.69 (m, 4H), 3.19-3.22 (m, 4H). MS (ES+): 418 (M+1).

The title compound was obtained by employing the general Method C using the intermediate 4a. TLC (Rt): 0.41 (30% EtOAc in hexanes).

$^1$H NMR (300 MHz, $CD_3OD$) δ: 8.41 (m, 1H), 7.97-8.10 (m, 3H), 7.76-7.80 (dd, J=1.8, 8.4 Hz, 1H), 7.76 (s, 1H), 7.64-7.69 (m, 2H), 3.66-3.69 (m, 4H), 3.23-3.20 (m, 4H). MS (ES+): 419 (M+1).

Example 2

Synthesis of 1-(2-naphthylsulfonyl)-4-(5-hydroxyaminocarbonylthiazol-2-yl)-1,4-diazepane

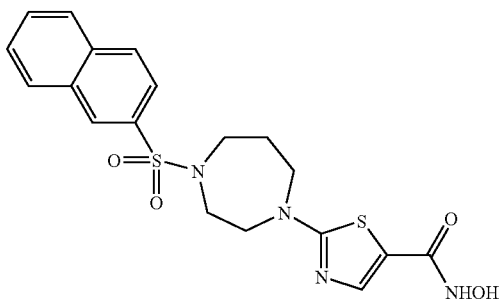

Intermediate 3b was obtained by the general Method A using methyl 2-bromothiazole-5-caboxylate 1a and N-Boc homopiperazine 2b. Yield (1.56 g, 99%). TLC (Rt): 0.33 (25% EtOAc in hexanes).

$^1$H NMR (300 MHz, $CDCl_3$) δ: 7.70 (s, 1), 3.82-3.85 (m, 2H) 3.78 (s, 3H), 3.68-3.72 (m, 2H), 3.52-3.56 (m, 2H), 3.33-3.37 (m, 2H), 2.09-2.13 (s, 2H) 1.49 (s, 9H). MS (ES+): 342 (M+1).

Intermediate 4b was obtained by employing the general Method B using the intermediate 3b. Yield: 50%. TLC (Rt): 0.33 (50% EtOAc in hexanes).

¹H NMR (300 MHz, CDCl$_3$) δ: 8.32 (m, 1H), 7.84-7.96 (m, 3H), 7.70 (s, 1H), 7.67-7.71 (m, 1H), 7.58-7.62 (m, 2H), 3.82-3.85 (m, 2H) 3.78 (s, 3H), 3.68 -3.72 (m, 2H), 3.52-3.56 (m, 2H), 3.33-3.37 (m, 2H), 2.09-2.13 (s, 2H). MS (ES+): 432 (M+1).

The title compound was obtained by employing the general Method C using the intermediate 4b. TLC (Rt): 0.41 (30% EtOAc in hexanes).

¹H NMR (300 MHz, CD$_3$OD) δ: 8.35 (m, 1H), 7.90-8.00 (m, 3H), 7.72-7.59 (dd, J=1.8, 8.4 Hz, 1H), 7.60-7.64 (m, 2H), 7.52 (s, 1H), 3.74-3.76 (m, 2H), 3.66-3.69 (m, 4H), 3.50-3.52 (m, 2H), 1.95-2.00(m, 2H); MS (ES+): 433 (M+1).

Example 3

Synthesis of 1-(2-naphthylsulfonyl)-4-(4-hydroxyaminocarbonylthiazol-2-yl)piperazine

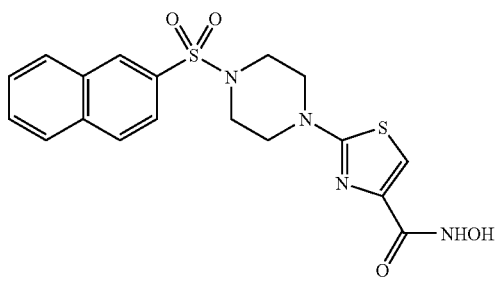

Intermediate 3c was obtained by the general Method A using methyl 2-bromothiazole-4-caboxylate 1a and N-Boc piperazine 2a. Yield (1.4 g, 99%). TLC (Rt): 0.37 (20% EtOAc in hexanes).

¹H NMR (300 MHz, CDCl$_3$) δ: 7.40 (s, 1H), 4.31 (q, J=6.9, 13.8 Hz, 2H), 3.62-3.66 (m, 4H), 3.19-3.22 (m, 4H), 1.57 (s, 9H), 1.30 (t, J=7.2 Hz, 3H). MS (ES+): 342 (M+1).

Intermediate 4a was obtained by employing the general Method B using the intermediate 3a. TLC (Rt): 0.41 (30% EtOAc in hexanes).

¹H NMR (300 MHz, CDCl$_3$) δ: 8.32 (d, J=1.5 Hz, 1H), 7.89-7.98 (m, 3H), 7.70-7.74 (dd, J=1.8, 8.4 Hz, 1H), 7.61-7.66 (m, 2H), 7.40 (s, 1H), 4.31 (q, J=6.9, 13.8 Hz, 2H), 3.62-3.66 (m, 4H), 3.19-3.22 (m, 4H), 1.57 (s, 9H), 1.30 (t, J=7.2 Hz, 3H). MS (ES+): 432 (M+1).

The title compound was obtained by employing the general Method C using the intermediate 4c.

¹H NMR (300 MHz, CD$_3$OD) δ: 8.41 (m, 1H), 7.97-8.10 (m, 3H), 7.56-7.79 (dd, J=1.8, 8.4 Hz, 1H), 7.64-7.69 (m, 2H), 7.37 (s, 1H), 3.61-3.58 (m, 4H), 3.17-3.21 (m, 4H); MS (ES+): 419 (M+1).

Example 4

Synthesis of 1-(2-naphthylsulfonyl)-4-[(5-(2-hydroxyaminocarbonylethen-1(E)-yl-thiazol-2-yl)piperazine

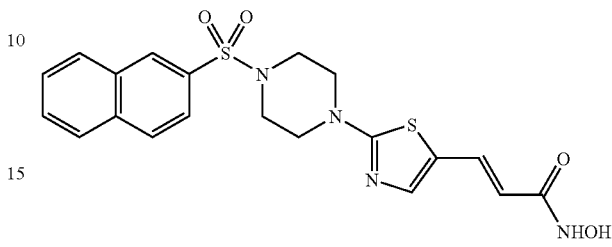

Intermediate 7 was obtained by the general Method A using 2-bromo-5-formylthiazole 6 and N-Boc piperazine 2a. Yield: 99%. TLC (Rt): 0.31 (50% EtOAc in hexanes).

¹H NMR (300 MHz, CDCl$_3$) δ: 9.69 (s, 1H), 7.85 (s, 1H), 3.57-3.64 (m, 8H), 1.48 (s, 9H). MS (ES+): 298 (M+1).

Intermediate 8 was obtained by employing the Wittig Horner reaction. Accordingly, to trimethylphosphano acetate (0.23 mL, 1.60 mmol) in THF (10 mL) at −30° C., butyl lithium (0.64 μL, 2.5 M solution in THF) was added and stirred at −30° C. for an hour. Intermediate 7 (0.4 g, 1.35 mmol) in THF (5 mL) was then added and stirred for another 2 hours while the temperature was brought to 0° C. After quenching the reaction with saturated aqueous ammonium chloride solution (20 mL), the product was extracted with ethyl acetate. The residue obtained on removal of solvent was purified on silica gel column chromatography using 30% ethyl acetate in hexanes (0.4 g, 84%). TLC (Rt): 0.57 (33% EtOAc in hexanes).

¹H NMR (300 MHz, CDCl$_3$) δ: 7.68 (d, J=15.9 Hz, 1H), 7.34 (s, 1H), 5.80 (d, J=15.3 Hz, 1H), 3.75 (s, 3H), 3.55 (m, 8H), 1.48 (s, 9H). MS (ES+): 354 (M+1).

Intermediate 9 was obtained by employing the general Method B using the intermediate 8. Yield: 0.3 g, 40%). TLC (Rt): 0.52 (50% EtOAc in hexanes).

¹H NMR (300 MHz, CDCl$_3$) δ: 8.32 (d, J=1.5 Hz, 1H), 7.89-7.98 (m, 3H), 7.70-7.73 (dd, J=1.8, 8.4 Hz, 1H), 7.61-7.66 (m, 3H), 7.61 (s, 1H), 5.70 (d, J=15.3 Hz, 1H), 3.73 (s, 3H), 3.66-3.69 (m, 4H), 3.19-3.22 (m, 4H). MS (ES+): 444 (M+1).

The title compound was obtained by employing the general Method C using the intermediate 9.

¹H NMR (300 MHz, DMSO-d$_6$) δ: 10.51 (s, 1H), 8.92 (s, 1H), 8.44 (s, 1H), 8.05-8.21 (m, 3H), 7.67-7.76 (m, 3H), 7.39 (s, 1H), 5.70 (d, J=15.3 Hz, 1H), 3.59 (m, 4), 3.10 (m, 4H). MS (ES+): 445 (M+1).

Following the procedures set forth in Example 4 above, except that Method C' rather than Method C was used for the hydroxamic acid formation, the compounds of Examples 4b-4m were prepared using the appropriate starting materials and the ¹H NMR data, HPLC and/or mass spectral data are presented below.

Example 4b 1-(phenylsulfonyl)-4-[(5-(2-hydroxyaminocarbonylethen-1(E)-yl-thiazol-2-yl)piperazine

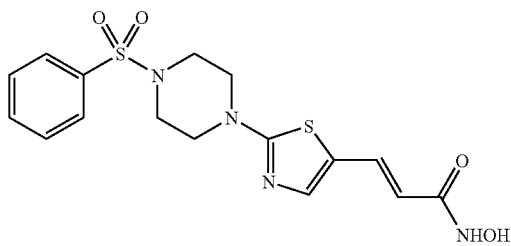

A solid (42 mg); HPLC (RT=13.09 min); $^1$H NMR (200 MHz, CD$_3$OD) δ: 3.26-3.34 (m, 4H), 3.78-3.83 (m, 4H), 6.03-6.1 (d, 1H, J=15.4 Hz), 7.54-7.92 (m, 7H).

Example 4c 1-(3,4-dimethoxyphenylsulfonyl)-4-[(5-(2-hydroxyaminocarbonylethen-1(E)-yl-thiazol-2-yl)piperazine

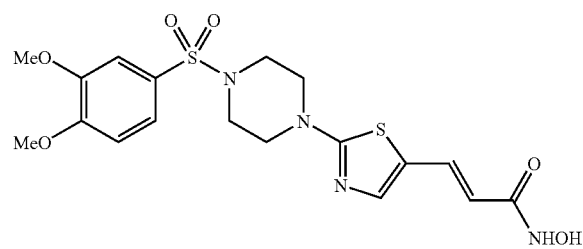

A solid (30 mg); HPLC (RT=12.88 min); $^1$H NMR (200 MHz, CD$_3$OD) δ: 3.23-3.31 (m, 4H), 3.79-3.81 (m, 4H), 3.925 (s, 6H), 5.99-6.07 (d, 1H, J=15.2 Hz), 7.15-7.62 (m, 5H).

Example 4d 1-(4-methoxyphenylsulfonyl)-4-[(5-(2-hydroxyaminocarbonylethen-1(E)-yl-thiazol-2-yl)piperazine

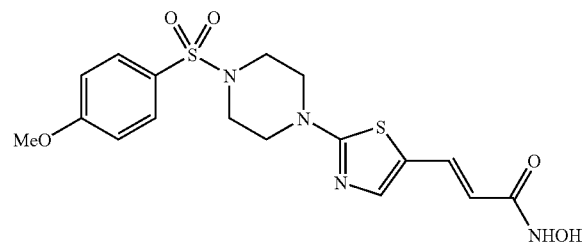

A solid (30 mg); HPLC (RT=13.26 min); $^1$H NMR (200 MHz, CD$_3$OD) δ: 3.25-3.31 (m, 4H), 3.8 (m, 4H), 3.9 (s, 3H), 6.03-6.1 (d, 1H, J=15.4 Hz), 7.13-7.18 (d, 2H, J=8.8 Hz), 7.62-7.65 (m, 1H), 7.76-7.8 (d, 2H, J=8.8 Hz), 7.92 (s, 1H).

Example 4e 1-(4-trifluoromethoxyphenylsulfonyl)-4-[(5-(2-hydroxyaminocarbonylethen-1(E)-yl-thiazol-2-yl)piperazine

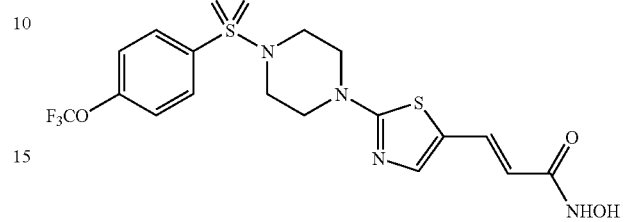

A solid (38 mg); HPLC (RT=14.61 min); $^1$H NMR (200 MHz, CD$_3$OD) δ: 3.31-3.34 (m, 4H), 3.8 (m, 4H), 5.99-6.07 (d, 1H, J=15.4 Hz), 7.55-7.62 (m, 3H), 7.92-7.99 (m, 3H).

Example 4f 1-(4-methylphenylsulfonyl)-4-[(5-(2-hydroxyaminocarbonylethen-1(E)-yl-thiazol-2-yl)piperazine

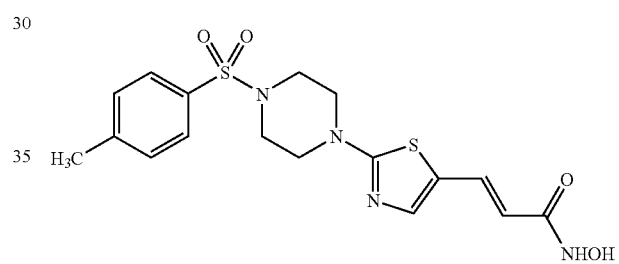

A solid (25 mg); HPLC (RT=13.6 min); $^1$H NMR (200 MHz, CD$_3$OD) δ: 2.46 (s, 3H), 3.24-3.31 (m, 4H), 3.78-3.8 (m, 4H), 6.03-6.11 (d, 1H, J=15.4 Hz), 7.45-7.74 (m, 6H).

Example 4g 1-(4-trifluoromethylphenylsulfonyl)-4-[(5-(2-hydroxyaminocarbonylethen-1(E)-yl-thiazol-2-yl)piperazine

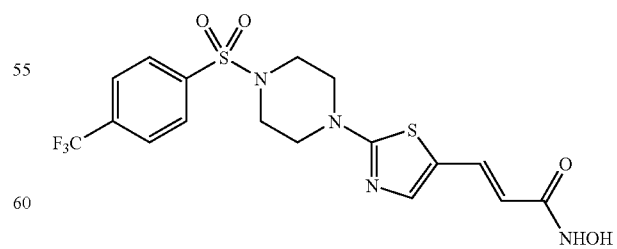

A solid (45 mg); HPLC (RT=14.49 min); $^1$H NMR (200 MHz, CD$_3$OD) δ: 3.31-3.36 (m, 4H), 3.83 (m, 4H), 6.04-6.12 (d, 1H, J=15.4 Hz), 7.13-7.18 (d, 2H, J=8.8 Hz), 7.54-7.66 (m, 2H), 7.96-8.08 (m, 4H).

Example 4h 1-(4-nitrophenylsulfonyl)-4-[(5-(2-hydroxyaminocarbonylethen-1(E)-yl-thiazol-2-yl)piperazine

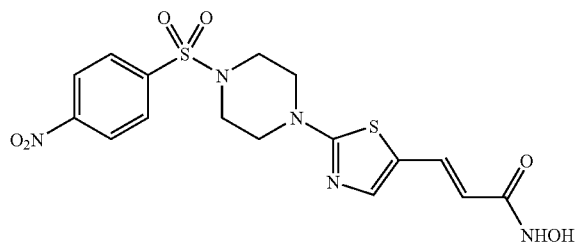

A solid (45 mg); HPLC (RT=13.47 min); ¹H NMR (200 MHz, CD$_3$OD) δ: 3.33 (m, 4H), 3.84 (m, 4H), 6.02-6.09 (d, 1H, J=15.4 Hz), 7.54-7.65 (m, 2H), 8.08-8.12 (d, 2H, J=8.8 Hz), 8.47-8.51 (d, 2H, J=8.8 Hz).

Example 4i 1-(thien-2-ylsulfonyl)-4-[(5-(2-hydroxyaminocarbonylethen-1(E)-yl-thiazol-2-yl)piperazine

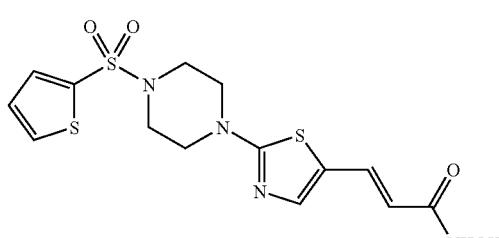

A solid (45 mg); HPLC (RT=12.99 min); ¹H NMR (200 MHz, CD$_3$OD) δ: 3.27-3.36 (m, 4H), 3.79-3.84 (m, 4H), 5.99-6.07 (d, 1H, J=15.8 Hz), 7.25-7.30 (m, 1H), 7.55-7.70 (m, 3H), 7.91-7.94 (d, 1H, J=6.2 Hz).

Example 4j 1-(1,1'biphenylsulfonyl)-4-[(5-(2-hydroxyaminocarbonylethen-1(E)-yl-thiazol-2-yl)piperazine

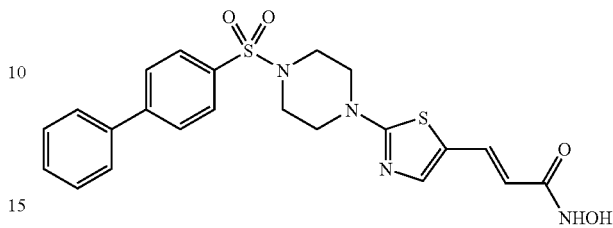

A solid (45 mg); HPLC (RT=14.91 min); ¹H NMR (200 MHz, CD$_3$OD) δ: 3.31-3.36 (m, 4H), 3.79-3.82 (m, 4H), 6.0-6.08 (d, 1H, J=15.4 Hz), 7.44-7.73 (m, 7H), 7.92 (m, 4H).

Example 4k 1-(5-dimethylamino-naphthalene-1-sulfonyl)-4-[(5-(2-hydroxyaminocarbonylethen-1(E)-yl-thiazol-2-yl)piperazine

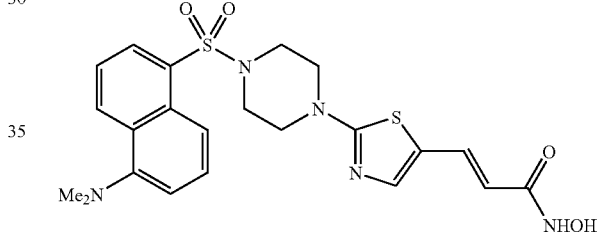

A solid (35 mg); HPLC (RT=13.41 min); ¹H NMR (200 MHz, CD$_3$OD) δ: 3.33 (m, 4H), 3.47 (s, 6H), 3.75 (m, 4H), 6.06 (d, 1H, J=15.4 Hz), 7.57 (m, 2H), 7.92-8.0 (m, 2H), 8.09-8.13 (d, 1H, J=7.6 Hz), 8.44-8.48 (d, 1H, J=7 Hz), 8.63-8.68 (d, 1H, J=8.4 Hz), 8.92-8.97 (d, 1H, J=8.8 Hz).

Example 4m 1-(4-fluorophenylsulfonyl)-4-[(5-(2-hydroxyaminocarbonylethen-1(E)-yl-thiazol-2-yl)piperazine

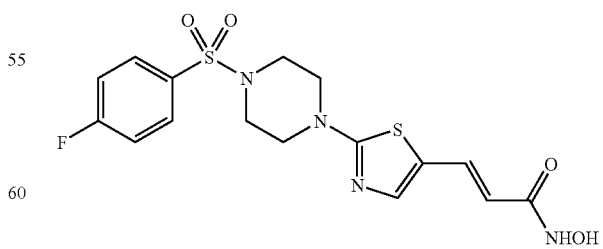

A solid (15 mg); HPLC (RT=13.30 min); ¹H NMR (200 MHz, CD$_3$OD) δ: 3.33 (m, 4H), 3.81 (m, 4H), 6.02-6.09 (d, 1H, J=15.4 Hz), 7.36-7.44 (m, 2H), 7.64 (m, 2H), 7.92 (m, 2H).

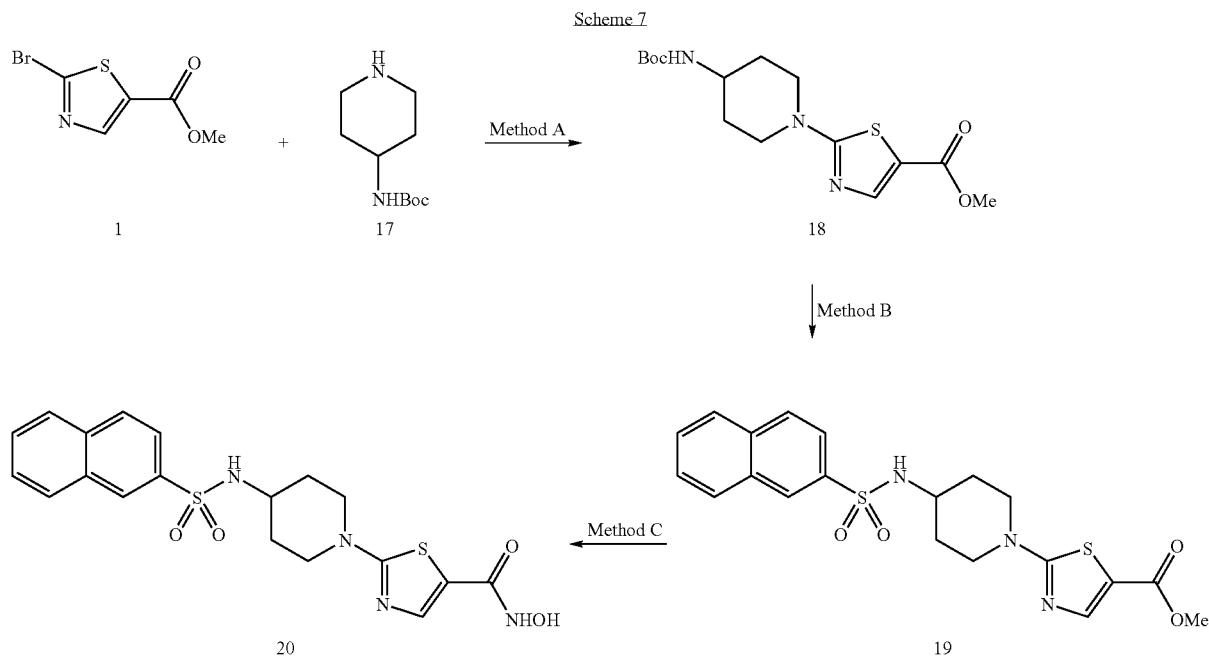

Example 5

Synthesis of 4-(2-naphthylsulfonylamino)-1-[(5-(2-hydroxyaminocarbonyl-thiazol-2-yl)piperadine (20)

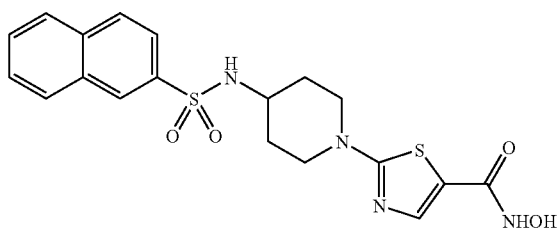

Intermediate 18 was obtained by the general Method A using methyl 2-bromothiazole-5-caboxylate 1 and 4-N-Boc-aminopiperidine 17. TLC (Rt): 0.28 (25% EtOAc in hexanes).

$^1$H NMR (300 MHz, CDCl$_3$) δ: 7.79 (s, 1H), 4.63 (d, J=7.8 Hz, 1H), 3.86-3.91 (m, 2H), 3.50 (m, 1H), 3.07-3.17 (m, 2H), 1.88-1.93 (m, 1H), 1.47-1.60 (m, 2H), 1.49 (s, 9H). MS (ES+): 342 (M+1).

Intermediate 19 was obtained by employing the general Method B using the intermediate 18. TLC (Rt): 0.41 (30% EtOAc in hexanes).

$^1$H NMR (300 MHz, CDCl$_3$) δ: 8.45 (d, J=1.5 Hz, 1H), 7.89-7.98 (m, 3H), 7.80-7.84 (dd, J=1.8, 8.4 Hz, 1H), 7.79 (s, 1H), 7.61-7.66 (m, 2H), 4.63 (d, J=7.8 Hz, 1H), 3.86-3.91 (m, 2H), 3.50 (m, 1H), 3.07-3.17 (m, 2H), 1.88-1.93 (m, 1H), 1.47-1.60 (m, 2H), 1.49 (s, 9H). MS (ES+): 432 (M+1).

The title compound 20 was obtained by employing the general Method C using the intermediate 19.

$^1$H NMR (300 MHz, CDCl$_3$) δ: 8.45 (d, J=1.5 Hz, 1H), 7.96-8.07 (m, 3H), 7.85-7.89 (dd, J=1.8, 8.4 Hz, 1H), 7.74 (s, 1H), 7.61-7.68 (m, 2H), 3.81-3.86 (m, 2H), 3.50 (m, 1H), 3.17-3.27 (m, 2H), 1.88-1.93 (m, 2H), 1.47-1.60 (m, 2H). MS (ES+): 433 (M+1).

Following the procedures set forth in Example 5 above, except that Method C' rather than Method C was used for the hydroxamic acid formation, the compounds of Examples 5b-5d were prepared using the appropriate starting materials and the $^1$H NMR data, HPLC and/or mass spectral data are presented below.

Example 5b 4-(1,1'-biphenylsulfonylamino)-1-[(5-(2-hydroxyaminocarbonyl-thiazol-2-yl)-piperadine

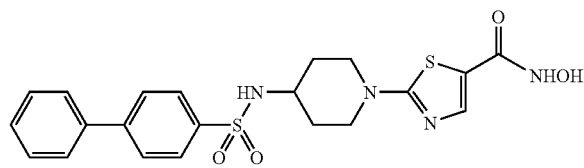

A white solid (50 mg); HPLC (RT 14.26 min); $^1$H NMR (CD$_3$OD, 200 MHz) δ: 7.91(4H,s), 7.74-7.44 (6H, m), 3.87-3.52 (3H,m), 2.76 (2H, m), 2.13 (2H, m), 1.78 (2H, m); MS (m/z) 455 (M+H$^+$).

Example 5c 4-(3,4-dimethoxyphenylsulfonylamino)-1-[(5-(2-hydroxyaminocarbonyl-thiazol-2-yl)-piperadine

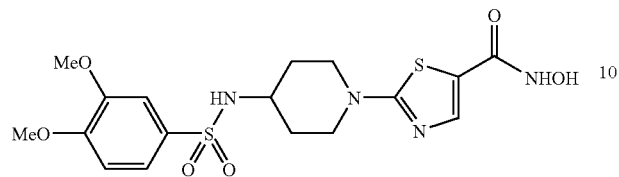

A white solid (49 mg); HPLC (RT 12.12 min); $^1$H NMR (CD$_3$OD, 200 MHz) δ: 7.45 (1H, dd, J=2.2, 8.4 Hz), 7.29 (1H, d, J=2.2 Hz), 7.12 (1H, d, J=8.4 Hz), 3.94 (3H, s), 3.87 (3H, s), 3.75-3.57 (3H,m), 2.70 (2H, m), 2.17 (2H, m), 1.75 (2H, m); MS (m/z) 442 (M+H$^+$).

Example 5d 4-(4-methylphenylsulfonylamino)-1-[(5-(2-hydroxyaminocarbonyl-thiazol-2-yl)-piperadine

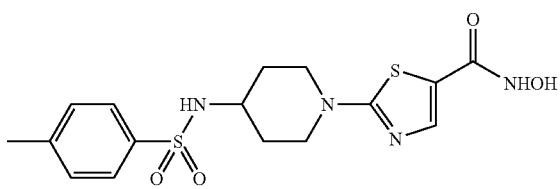

A white solid (50 mg); HPLC (RT 12.86 min); $^1$H NMR (CD$_3$OD, 200 MHz) δ: 7.77 (2H, d, J=8.4 Hz), 7.50 (2H, d, J=8.4 Hz), 3.80-3.48 (3H, m), 2.64 (2H, m), 2.52 (3H, s), 2.17 (2H, m), 1.75 (2H, m); MS (m/z) 396 (M+H$^+$).

Example 5e 2-(4-{[(1,1'-biphenylsulfonyl)amino]methyl}piperidin-1-yl)-1,3-thiazole-5-carboxylic acid hydroxyamide

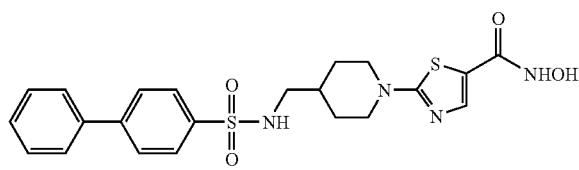

Intermediate 7B.2 was obtained by the general Method A using methyl 2-bromothiazole-5-carboxylate 1 and 4-aminomethylpiperidine 7B.1. $^1$HNMR 200 MHz (CDCl$_3$) δ: 1.25-1.4 (m, 4H), 1.53-1.59 (m, 1H), 1.84-1.89 (d, 2H, J=11.8 Hz), 2.65-2.65 (d, 2H, J=6.6 Hz), 3.02-3.16 (t, 3H), 3.82 (s, 3H), 4.06-4.13 (d, 2H, J=12.4 Hz), 7.86 (s, 1H).

Intermediate 7B.3 was obtained by employing the general Method B using the intermediate 7B.2. $^1$HNMR 200 MHz (CDCl$_3$) δ: 1.25-1.36 (m, 3H), 1.60 (m, 2H), 1.82-1.886 (m, 2H), 2.88-2.989 (m, 2H), 3.81 (s, 3H), 4.037-4.10 (m,2H), 4.67 (t, 1H), 7.26-7.94 (m, 10H).

The title compound 7B.4 (Example 5e) was obtained by employing the general Method C' using the intermediate 7B.3.

A white solid (75 mg); HPLC (RT=14.56 min); $^1$H NMR 200 MHz (CD$_3$OD) δ: 1.3-1.47 (m, 1H), 1.95-2.02 (m, 4H), 2.85-2.88 (d, 2H, J=6.4 Hz), 3.31-3.48 (m, 2H), 3.95-4.01 (d, 2H, J=12.8 Hz), 7.43-7.96 (m, 10H).

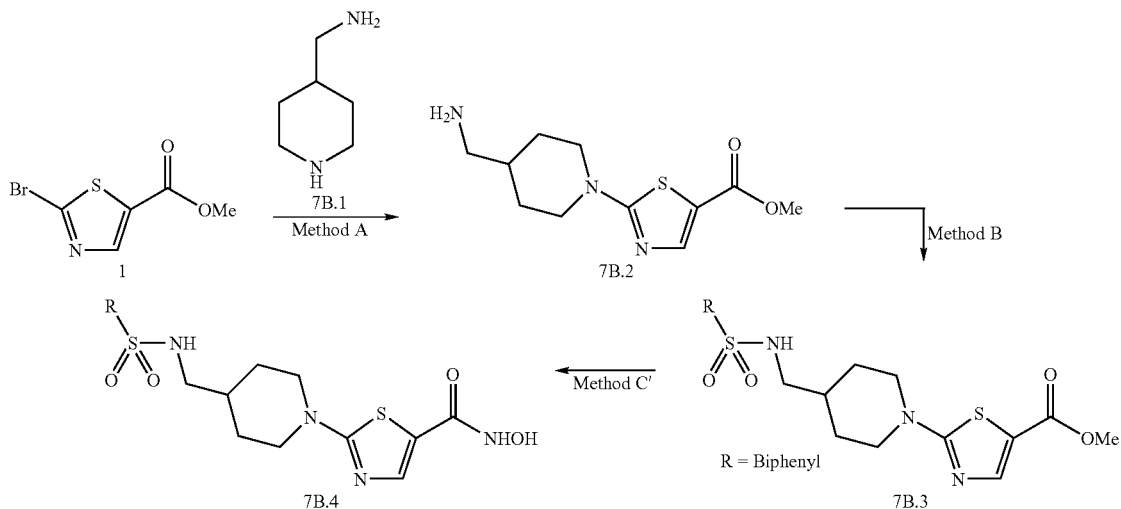

Scheme 7B

Scheme 7C

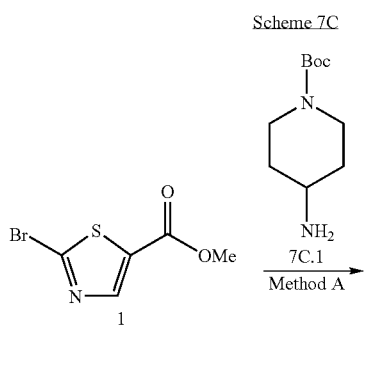

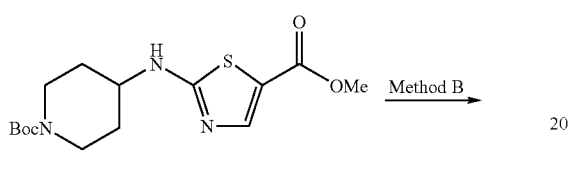

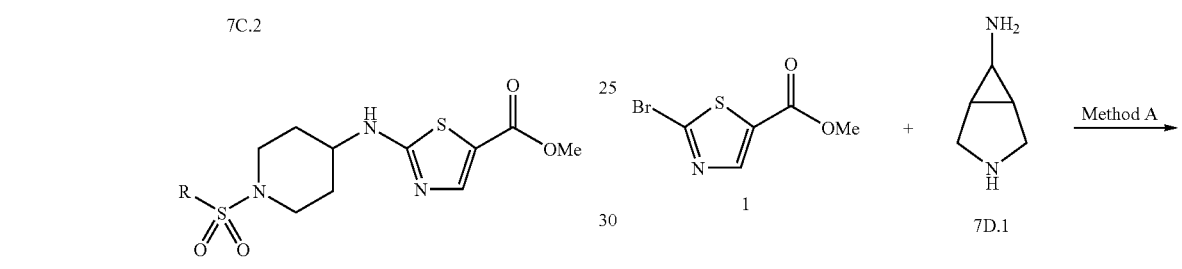

7C.4
R = 2-Napthyl

Example 5f

2-{[1-(2-naphthylsulfonyl)piperidin-4-yl]amino}-1,3-thiazole-5-carboxylic acid hydroxyamide

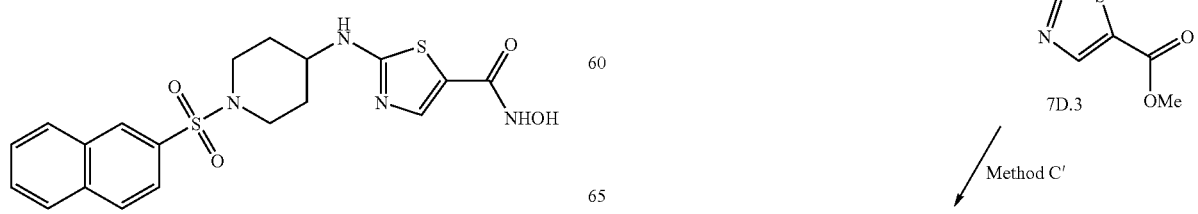

Intermediate 7C.2 was obtained by the general Method A using methyl 2-bromothiazole-5-carboxylate 1 and 1-N-Boc-4-aminopiperidine 7C.1. HPLC 90.47% (RT 6.66 min); $^1$H NMR 200 MHz (CDCl$_3$) δ: 7.81 (1H, s), 6.13 (1H, bs), 4.11 (2H, m), 3.83 (3H, s), 3.46 (1H, m), 2.93 (2H, m), 2.14 (2H, m), 1.47 (1H, m).

Intermediate 7C.3 was obtained by employing the general Method B using the intermediate 7C.2. A white solid (170 mg); HPLC (RT 10.88 min); $^1$H NMR (CDCl$_3$, 200 MHz) δ: 8.35 (1H, s), 8.02-7.93 (3H, m), 7.78-7.63 (4H, m), 5.62 (1H, d, J=7.2 Hz), 3.79 (3H, s), 3.76 (2H, m), 3.42 (1H, m), 2.62 (2H, m), 2.18 (2H, m), 1.63 (2H, m).

The title compound 7C.4 (Example 5f) was obtained by employing the general Method C' using the intermediate 7C.3. A white solid (40 mg); HPLC (RT 13.55 min); MS (m/z) 438 (M+H$^+$).

Scheme 7D

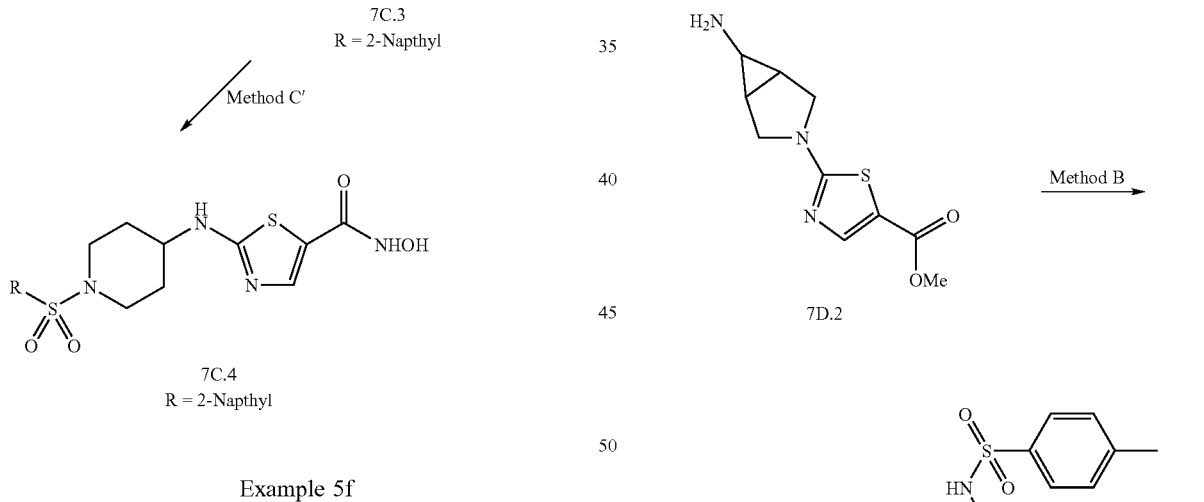

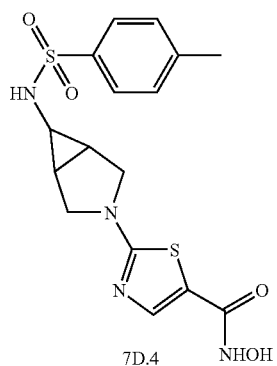

Example 5g 2-(6-{[(4-methylphenyl)sulfonyl]amino}-3-azabicyclo[3.1.0]hex-3-yl)-1,3-thiazole-5-carboxylic acid hydroxyamide

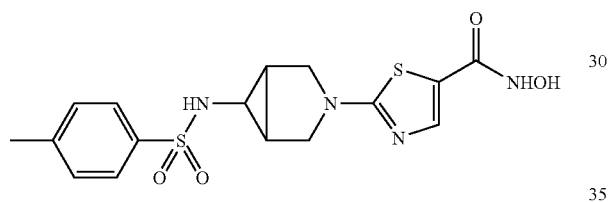

Intermediate 7D.2 was obtained by the general Method A using methyl 2-bromothiazole-5-carboxylate 1 and 3-azabicyclo[3.1.0]hexan-6-amine 7D.1. MS m/e: 240 (M+H⁺).

Intermediate 7D.3 was obtained by employing the general Method B using the intermediate 7D.2. ¹HNMR (200 MHz, CD₃OD) δ: 7.79 (s, 1H), 7.71 (d, 2H, J=8.0 Hz), 7.35 (d, 2H, J=8.0 Hz), 3.81 (s, 3H), 3.57 (m, 5H), 2.44 (s, 3H), 2.095 (m, 2H); MS m/e=394 (M+H⁺).

The title compound 7D.4 (Example 5g) was obtained by employing the general Method C' using the intermediate 7D.3. A white solid (44 mg); ¹H NMR (CD₃OD, 200 MHz) δ: 7.95 (s, 1H), 7.81 (d, 2H, J=8.2 Hz), 7.46 (d, 2H, J=8.2 Hz); 3.95-3.61 (m, 5H), 2.44 (s, 3H), 2.16 (m, 2H); MS m/e=395 (M+H⁺); HPLC (RT: 12.14 min).

Scheme 7E

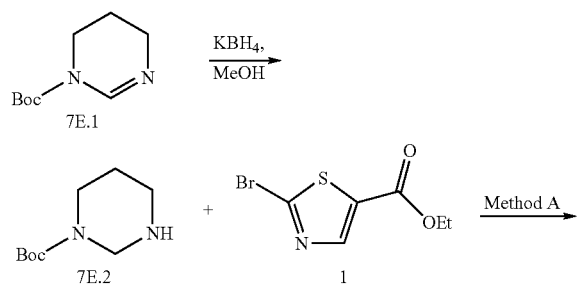

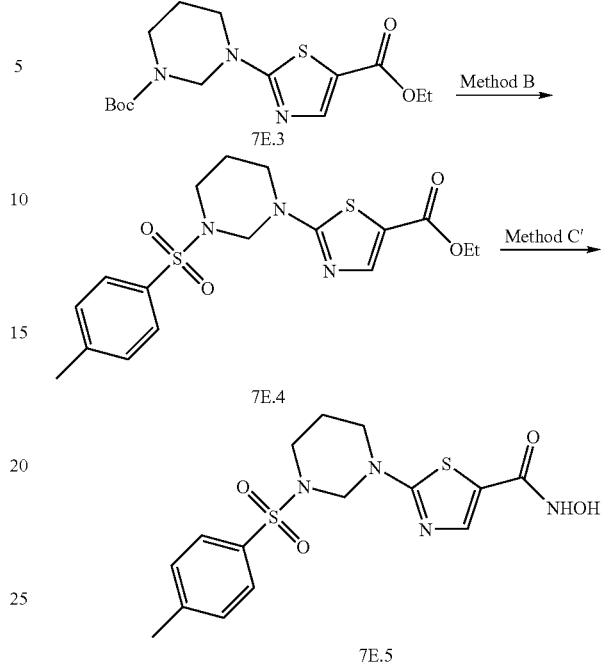

Example 5h

2-[3-[(4-methylphenyl)sulfonyl]tetrahydropyrimidin-[(2H)-yl]-1,3-thiazole-5-carboxylic acid hydroxylamide

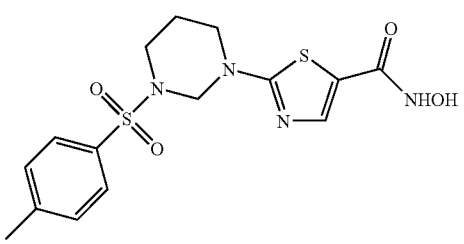

To a solution of tert-butyl 5,6-dihydropyrimidine-1(4H)-carboxylate 7E.1 (350 mg, 1.90 mmole) in methanol (10 mL) was added potassium borohydride (205 mg, 3.80 mmoles) at 0° C. The reaction mixture was stirred at room temperature for 2 hours. After completion of the reaction, ice (10 g) was added to the mixture and stirred for 10 min. Solvent was evaporated under reduced pressure and the compound was extracted twice with dichloromethane (50 ml). The organic layer was separated, dried over sodium sulfate, filtered and the solvent was removed under reduced pressure to give crude residue, which was purified by column chromatography using silica gel to provide compound 7E.2 (350 mg, 94%); ¹HNMR (CDCl₃) δ: 4.31 (s, 2H), 3.54 (t, 2H, J=5.4 Hz), 2.94 (t, 2H, J=5.4 Hz), 1.54 (m, 2H), 1.46 (s, 9H); MS m/e=186 (M+H⁺).

Intermediate 7E.3 was obtained by the general Method A using methyl 2-bromothiazole-5-carboxylate 1 and 7E.2. ¹HNMR (CDCl₃) δ: 7.83 (s, 1H), 5.05 (s, 2H), 4.27 (q, 2H, J=5.0, 7.2 Hz), 3.72 (t, 2H, J=5.4 Hz), 3.59 (t, 2H, J=5.4 Hz), 1.77 (m, 2H), 1.48 (s, 9H), 1.38 (t, 3H, J=7.2 Hz); MS m/e=342(M+H⁺).

Intermediate 7E.4 was obtained by employing the general Method B using the intermediate 7E.3. ¹H NMR (CDCl₃+ DMSO-D₆, 200 MHz) δ: 7.85 (s, 1H), 5.08(s, 2H), 4.31 (q, 2H, J=5.1, 7.2 Hz), 3.75 (t, 2H, J=5.2 Hz), 3.44 (t, 2H, J=5.2 Hz), 2.09 (m, 2H), 1.37 (t, 3H, J=7.2 Hz); MS m/e=242 (M+H⁺).

The title compound 7E.5 (Example 5h) was obtained by employing the general Method C' using the intermediate 7E.4. A solid (36 mg, 68% yield); ¹H NMR (CD₃OD, 200 MHz) δ: 7.91 (bs, 1H), 7.73 (d, 2H, J=8.6 Hz), 7.39 (d, 2H, J=8.6 Hz); 5.12 (s, 2H), 3.64-3.54 (m, 4H), 2.43 (s, 3H), 1.76 (m, 2H); MS m/e=383 (M+1); HPLC (RT: 12.89 min).

Example 6

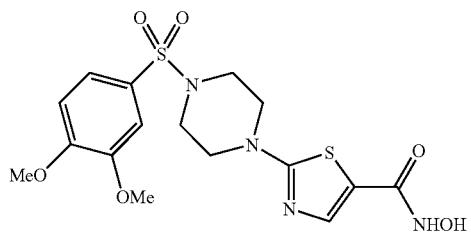

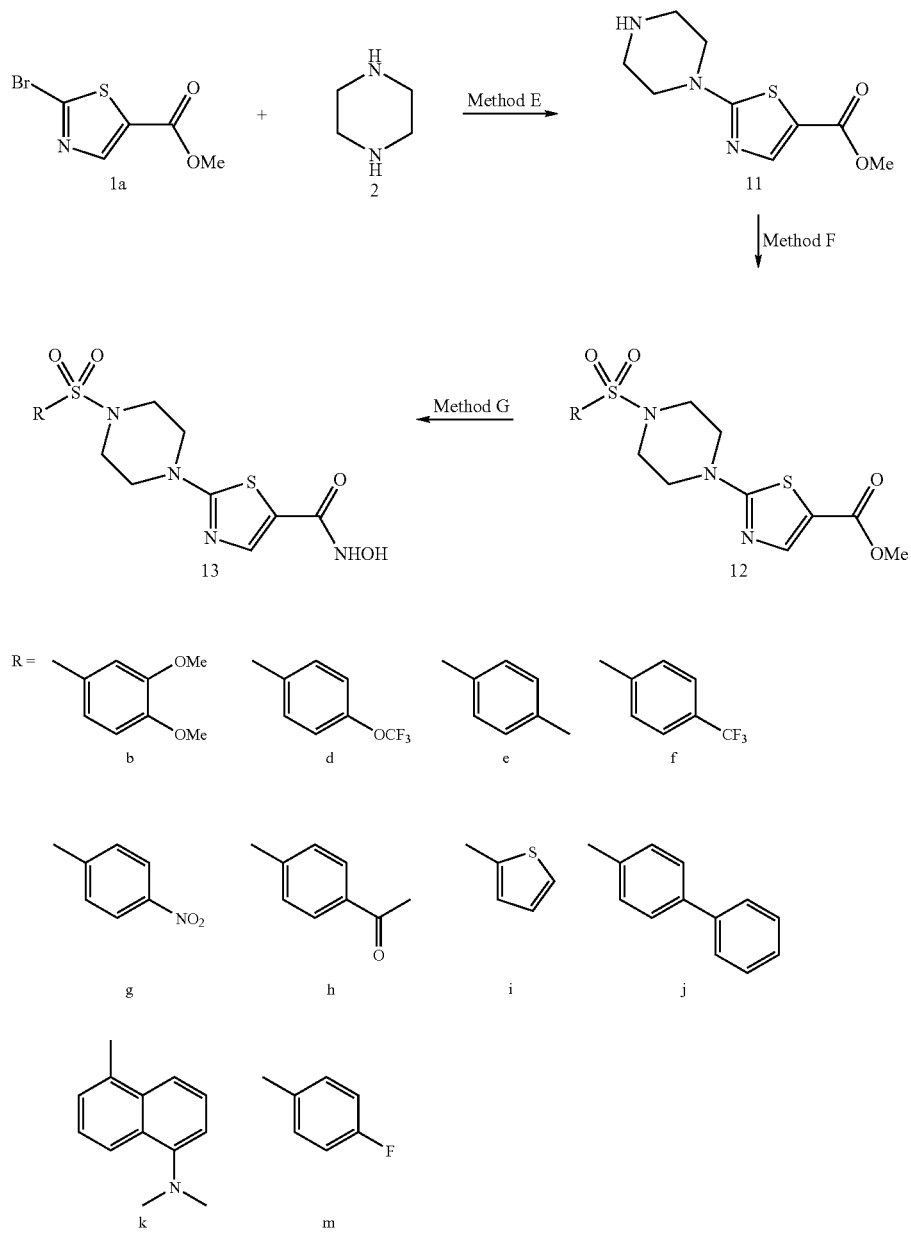

Preparation of 2-piperazin-1-yl-thiazole-5-carboxylic acid methyl ester (11)

To a solution of methyl 2-bromothiazole-5-carboxylate (1a) (5.00 g, 22.50 mmol) in acetonitrile (50 mL) were added piperazine 2 (2.32 g, 26.97 mmol) and potassium carbonate (6.22 g, 45.05 mmol) under a $N_2$ atmosphere. The reaction mixture was heated to reflux at 80° C. for 10 h. The reaction mixture was filtered through Celite and the filtrate was concentrated under reduced pressure. The residue was purified by column chromatography using silica gel to give the compound 11 as a solid (4.10 g, 79.8%). HPLC: 92% (Rt=3.883 min).

$^1$H NMR (CDCl$_3$, 200 MHz) δ: 7.88 (1H, s), 3.89 (3H, s), 3.55 (4H, t, J=6.0 Hz), 2.98 (4H, t, J=6.0 Hz). MS (m/z): 228 (M+1).

Preparation of 2-[4-(3,4-dimethoxy-benzene sulfonyl)-piperazin-1-yl]-thiazole-5-carboxylic acid methyl ester (12b)

To a solution of intermediate 11 (200 mg, 0.886 mmol) in dichloromethane (7.5 mL) were added 3,4-dimethoxybenzenesulfonyl chloride (320 mg, 1.320 mmol) and triethylamine (220 mg, 2.169 mmol) under a $N_2$ atmosphere. The reaction mixture was stirred at room temperature for 4 h. Water (10 mL) followed by dichloromethane (10 mL) were added to the reaction mixture and the organic layer was separated, dried on sodium sulfate, filtered and concentrated under reduced pressure. The residue was purified by column chromatography using silica gel to give the compound 12b as a solid (200 mg, 53.0%). HPLC: 99% (Rt 6.507 min).

$^1$H NMR (CDCl$_3$, 200 MHz) δ: 7.82 (1H, s), 7.38 (1H, dd, J=2.2, 8.6 Hz), 7.19 (1H, d, J=2.2 Hz), 6.96 (1H, d, J=8.6 Hz), 3.93 (6H, 2s), 3.83 (3H, s), 3.68 (4H, t, J=5.2 Hz), 3.14 (4H, t, J=5.2 Hz). MS (m/z): 427 (M+1).

Preparation of 2-[4-(3,4-dimethoxy-benzene sulfonyl)-piperazin-1-yl]-thiazole-5-carboxylic acid hydroxyamide (13b)

To a solution of compound (12b) (125 mg, 0.292 mmol) in 1,4-dioxane (2 mL) were added hydroxylamine hydrochloride (202 mg, 2.92 mmol) and a freshly prepared solution of sodium methoxide in methanol (100 mg, 4.35 mmol of sodium dissolved in 1 mL of methanol) under $N_2$ atmosphere. The reaction mixture was stirred at room temperature for 2 h. The reaction mixture was acidified to pH~6 with 1M HCl and the formed precipitates were filtered off. The filtrate was diluted with ethylacetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 13b as a solid. HPLC: 86.09% (Rt=12.51 min).

$^1$H NMR (CD$_3$OD, 200 MHz) δ: 8.14 (1H, s), 7.61-7.08 (3H, m), 3.83 (6H, s), 3.54 (4H, m), 3.03 (4H, m). MS (ES+): 429 (M+1).

Example 7

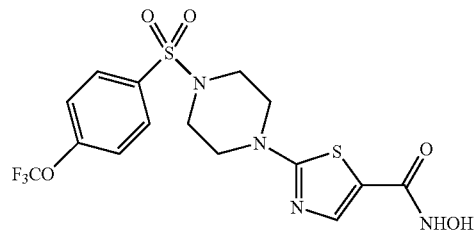

Preparation of 2-[4-(4-trifluoromethoxy-benzene sulfonyl)-piperazin-1-yl]-thiazole-5-carboxylic acid methyl ester (12d)

To a solution of compound 11 (200 mg, 0.886 mmol) in dichloromethane (7.5 mL) were added 4-trifluoromethoxy-benzenesulfonyl chloride (344 mg, 1.320 mmol) and triethylamine (220 mg, 2.169 mmol) under a $N_2$ atmosphere. The reaction mixture was stirred at room temperature for 4 h. Water (10 mL) followed by dichloromethane (10 mL) were added to the reaction mixture and the organic layer was separated, dried on sodium sulfate, filtered and concentrated under reduced pressure. The residue was purified by column chromatography using silica gel to give the compound 12d as a solid (313 mg, 78.8%). HPLC: 98% (Rt=12.22 min).

$^1$H NMR (CDCl$_3$, 200 MHz) δ: 7.82 (3H, m), 7.44 (2H, d, J=8.0 Hz), 3.84 (3H, s), 3.74 (4H, t, J=5.8 Hz), 3.20 (4H, t, J=5.8 Hz). MS (m/z): 451 (M+1).

Preparation of 2-[4-(4-trifluoromethoxy-benzene sulfonyl)-piperazin-1-yl]-thiazole-5-carboxylic acid hydroxyamide (13d)

To a solution of compound (12d) (125 mg, 0.276 mmol) in 1,4-dioxane (2 mL) were added hydroxylamine hydrochloride (191 mg, 2.76 mmol) and a freshly prepared solution of sodium methoxide in methanol (95 mg, 4.14 mmol of sodium dissolved in 1 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 13d as a solid. HPLC: =92% (Rt=14.16 min).

$^1$H NMR (CD$_3$OD, 200 MHz) δ: 8.00 (3H, m), 7.57 (2H, m), 3.64 (4H, m), 3.19 (4H, m); MS (m/z): 453 (M+1).

Example 8

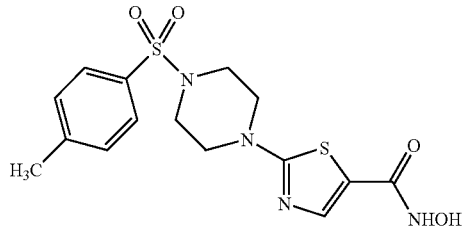

Preparation of 2-[4-(toluene-4-sulfonyl)-piperazin-1-yl]-thiazole-5-carboxylic acid methyl ester (12e)

To a solution of compound 11 (200 mg, 0.886 mmol) in dichloromethane (7.5 mL) were added 4-methyl benzenesulfonyl chloride (251 mg, 1.320 mmol) and triethylamine (220 mg, 2.169 mmol) under a $N_2$ atmosphere. The reaction mixture was stirred at room temperature for 4 h. Water (10 mL) followed by dichloromethane (10 mL) were added to the reaction mixture and the organic layer was separated, dried on sodium sulfate, filtered and concentrated under reduced pressure. The residue was purified by column chromatography using silica gel to give the compound 12e as a solid (275 mg, 82%). HPLC: 99.62% (Rt=9.22 min).

$^1$H NMR (CDCl$_3$, 200 MHz) δ: 7.82 (1H, s), 7.66 (2H, d, J=8.4 Hz), 7.35 (2H, d, J=8.4 Hz), 3.82 (3H, s), 3.68 (4H, t, J=5.6 Hz), 3.14 (4H, t, J=5.6 Hz), 2.44 (3H, s). MS (m/z): 382 (M+1).

Preparation of 2-[4-(4 toluene-4-sulfonyl)-piperazin-1-yl]-thiazole-5-carboxylic acid hydroxyamide (13e)

To a solution of compound 12e (125 mg, 0.327 mmol) in 1,4-dioxane (2 mL) were added hydroxylamine hydrochloride (227 mg, 3.27 mmol) and a freshly prepared solution of sodium methoxide in methanol (112 mg, 4.91 mmol of sodium dissolved in 1 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 13e as a solid. HPLC: 90% (Rt=13.23 min).

$^1$H NMR (CD$_3$OD, 200 MHz) δ: 7.79 (3H, m), 7.44 (2H, d, J=8.6 Hz), 3.65 (4H, t, J=5.4 Hz), 3.12 (4H, t, J=5.4 Hz), 2.46 (3H, s). MS (m/z): 382.6 (M+1).

Example 9

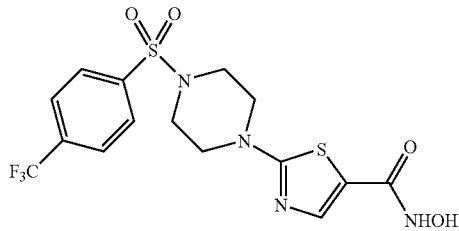

Preparation of 2-[4-(4-trifluoromethyl-benzenesulfonyl)-piperazin-1-yl]-thiazole-5-carboxylic acid methyl ester (12f)

To a solution of compound 11 (200 mg, 0.886 mmol) in dichloromethane (7.5 mL) were added 4-trifluoromethyl benzenesulfonyl chloride (322 mg, 1.320 mmol) and triethylamine (220 mg, 2.169 mmol) under a $N_2$ atmosphere. The reaction mixture was stirred at room temperature for 4 h. Water (10 mL) followed by dichloromethane (10 mL) were added to the reaction mixture and the organic layer was separated, dried on sodium sulfate, filtered and concentrated under reduced pressure. The residue was purified by column chromatography using silica gel to give the compound 12f as a solid (333 mg, 86.9%). HPLC: 99.42% (Rt=11.936 min).

$^1$H NMR (CDCl$_3$, 200 MHz) δ: 7.88-7.82 (5H, m), 3.81 (3H, s), 3.70 (4H, t, J=5.2 Hz), 3.19 (4H, t, J=5.2 Hz). MS (m/z): 435 (M+1), 245.

Preparation of 2-[4-(4-trifluoromethyl-benzenesulfonyl)-piperazin-1-yl]-thiazole-5-carboxylic acid hydroxyamide (13f)

To a solution of compound 12f (125 mg, 0.287 mmol) in 1,4-dioxane (2 mL) were added hydroxylamine hydrochloride (199 mg, 2.87 mmol) and a freshly prepared solution of sodium methoxide in methanol (99 mg, 4.30 mmol of sodium dissolved in 1 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 13f (20 mg, yield 16%). HPLC 85.42% (Rt=14.11 min).

$^1$H NMR (CD$_3$OD, 200 MHz): δ 8.03 (4H, m), 7.81 (1H, s), 3.75 (4H, m), 3.21 (4H, m). MS (m/z): 436 (M+1).

Example 10

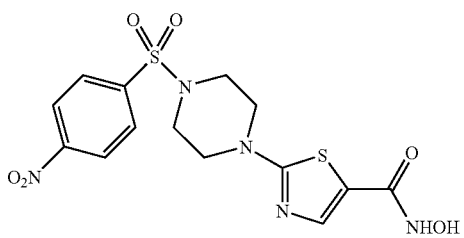

Preparation of 2-[4-(4-nitro-benzenesulfonyl)-piperazin-1-yl]-thiazole-5-carboxylic acid methyl ester (12g)

To a solution of compound 11 (200 mg, 0.886 mmol) in dichloromethane (7.5 mL) were added 4-nitro benzenesulfonyl chloride (292 mg, 1.320 mmol) and triethylamine (220 mg, 2.169 mmol) under a $N_2$ atmosphere. The reaction mixture was stirred at room temperature for 4 h. Water (10 mL) followed by dichloromethane (10 mL) were added to the reaction mixture and the organic layer was separated, dried on sodium sulfate, filtered and concentrated under reduced pressure. The residue was purified by column chromatography using silica gel to give the compound 12g as a solid (120 mg, 33.3%). HPLC: 97% (Rt=7.76 min).

$^1$H NMR (CDCl$_3$, DMSO-D$_6$, 200 MHz) δ: 8.50 (2H, d, J=8.0 Hz), 8.01 (2H, d, J=8.0 Hz), 7.84 (1H, s), 3.81 (3H, s), 3.71 (4H, t, J=5.6 Hz), 3.23 (4H, t, J=5.6 Hz).

Preparation of 2-[4-(4-nitro-benzenesulfonyl)-piperazin-1-yl]-thiazole-5-carboxylic acid hydroxyamide (13g)

To a solution of compound 12g (125 mg, 0.303 mmol) in 1,4-dioxane (2 mL) were added hydroxylamine hydrochloride (210 mg, 3.03 mmol) and a freshly prepared solution of sodium methoxide in methanol (104 mg, 4.50 mmol of sodium dissolved in 1 mL of methanol) under N$_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 13g

Example 11

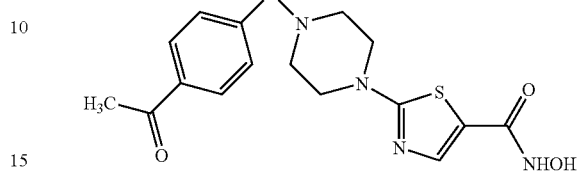

Preparation of 2-[4-(4-acetyl-benzenesulfonyl)-piperazin-1-yl]-thiazole-5-carboxylic acid methyl ester (12h)

To a solution of compound 11 (200 mg, 0.886 mmol) in dichloromethane (7.5 mL) were added 4-acetyl-benzenesulfonyl chloride (288 mg, 1.320 mmol) and triethylamine (220 mg, 2.169 mmol) under a $N_2$ atmosphere. The reaction mixture was stirred at room temperature for 4 h. Water (10 mL) followed by dichloromethane (10 mL) were added to the reaction mixture and the organic layer was separated, dried on sodium sulfate, filtered and concentrated under reduced pressure. The residue was purified by column chromatography using silica gel to give the compound 12h as a solid (346 mg, 96.2%). HPLC: 99.72% (Rt=6.56 min).

$^1$H NMR (CDCl$_3$, DMSO-D$_6$, 200 MHz) δ: 8.10 (2H, d, J=8.0 Hz), 7.89 (2H, d, J=8.0 Hz), 7.79 (1H, s), 3.80 (3H, s), 3.69 (4H, t, J=5.4 Hz), 3.18 (4H, t, J=5.4 Hz), 2.66 (3H, s). MS (m/z): 410 (M+1).

Preparation of 2-[4-(4-acetyl-benzenesulfonyl)-piperazin-1-yl]-thiazole-5-carboxylic acid hydroxyamide (13h)

To a solution of compound (12h) (125 mg, 0.305 mmol) in 1,4-dioxane (2 mL) were added hydroxylamine hydrochloride (211 mg, 3.05 mmol) and a freshly prepared solution of sodium methoxide in methanol (105 mg, 4.57 mmol of sodium dissolved in 1 mL of methanol) under a N$_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 13 h (15 mg, yield 12.0%). HPLC: 92.26% (Rt=12.51 min).

$^1$H NMR (CD$_3$OD, 200 MHz): δ 7.86-7.68 (5H, m), 3.64 (4H, m), 3.17 (4H, m), 2.26 (3H, s).

Example 12

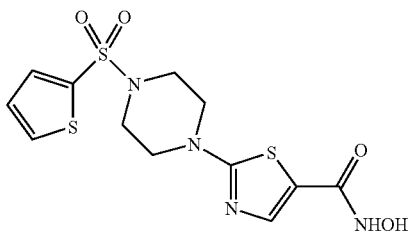

Preparation of 2-[4-(thiophene-2-sulfonyl)-piperazin-1-yl]-thiazole-5-carboxylic acid methyl ester (12i)

To a solution of compound 11 (200 mg, 0.886 mmol) in dichloromethane (7.5 mL) were added 2-thiophene sulfonyl chloride (241 mg, 1.320 mmol) and triethylamine (220 mg, 2.169 mmol) under a $N_2$ atmosphere. The reaction mixture was stirred at room temperature for 4 h. Water (10 mL) followed by dichloromethane (10 mL) were added to the reaction mixture and the organic layer was separated, dried on sodium sulphate, filtered and concentrated under reduced pressure. The residue was purified by column chromatography using silica gel to give the compound 12i as a solid (300 mg, 91.4%). HPLC: 99.74% (Rt=7.22 min).

$^1$H NMR (CDCl$_3$, 200 MHz) δ: 7.83 (1H, s), 7.67-7.55 (2H, m), 7.16 (1H, m), 3.82 (3H, s), 3.71 (4H, t, J=5.4 Hz), 3.20 (4H, t, J=5.4 Hz). MS (m/z): 373 (M+1).

Preparation of 2-[4-(thiophene-2-benzenesulfonyl)-piperazin-1-yl]-thiazole-5-carboxylic acid hydroxyamide (13i)

To a solution of compound 12i (125 mg, 0.334 mmol) in 1,4-dioxane (2 mL) were added hydroxylamine hydrochloride (232 mg, 3.34 mmol) and a freshly prepared solution of sodium methoxide in methanol (115 mg, 5.10 mmol of sodium dissolved in 1 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 13i (14 mg, yield 11.2%). HPLC: 58.9% (Rt=12.55 min).

$^1$H NMR (CD$_3$OD, 200 MHz) δ: 8.67 (1H, m), 7.85 (1H, m), 7.78 (1H, s), 7.59 (1H, m), 7.20 (1H, m), 3.67 (4H, m), 3.17 (4H, m).

Example 13

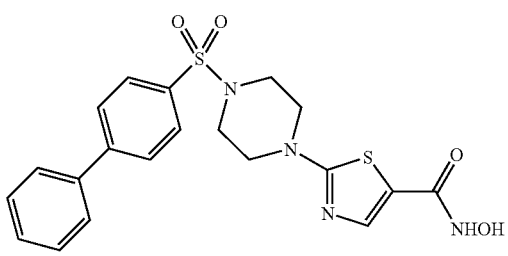

Preparation of 2-[4-(biphenyl-4-sulfonyl)-piperazin-1-yl-thiazole-5-carboxylic acid methyl ester (12j)

To a solution of compound 11 (200 mg, 0.886 mmol) in dichloromethane (7.5 mL) were added 4-biphenyl sulfonyl chloride (333 mg, 1.320 mmol) and triethylamine (220 mg, 2.169 mmol) under a $N_2$ atmosphere. The reaction mixture was stirred at room temperature for 4 h. Water (10 mL) followed by dichloromethane (10 mL) were added to the reaction mixture and the organic layer was separated, dried on sodium sulfate, filtered and concentrated under reduced pressure. The residue was purified by column chromatography using silica gel to give the compound 12j as a solid (200 mg, 51.2%). HPLC: 99.88% (Rt=15.46 min).

$^1$H NMR (CDCl$_3$, 200 MHz) δ: 7.89-7.76 (5H, m), 7.64-7.47 (5H, m), 3.82 (3H, s), 3.72 (4H, t, J=5.1 Hz), 3.22 (4H, t, J=5.1 Hz).

Preparation of 2-[4-(biphenyl-4-sulfonyl)-piperazin-1-yl]-thiazole-5-carboxylic acid hydroxyamide (13j)

To a solution of compound 12j (125 mg, 0.281 mmol) in 1,4-dioxane (2 mL) were added hydroxylamine hydrochloride (194 mg, 2.80 mmol) and a freshly prepared solution of sodium methoxide in methanol (96 mg, 4.20 mmol of sodium dissolved in 1 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 13j (9 mg, yield 7.2%). HPLC: 97.51% (Rt=14.61 min).

$^1$H NMR (CD$_3$OD, 200 MHz) δ: 7.91(1H, s), 7.76-7.41 (9H, m), 3.69 (4H, m), 3.21 (4H, m). MS (m/z): 445 (M+1).

Example 14

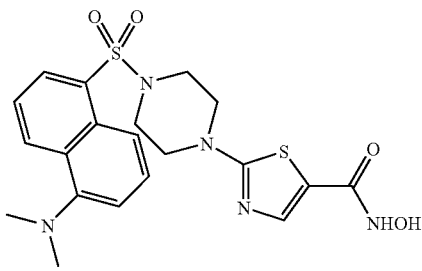

Preparation of 2-[4-(5-dimethylamino-naphthalene-1-sulfonyl)-piperazin-1-yl]-thiazole-5-carboxylic acid methyl ester (12k)

To a solution of compound 11 (200 mg, 0.886 mmol) in dichloromethane (7.5 mL) were added 5-dimethylamino-naphthalene-1-sulfonyl chloride (356 mg, 1.320 mmol) and triethylamine (220 mg, 2.169 mmol) under $N_2$ atmosphere. The reaction mixture was stirred at room temperature for 4 h. Water (10 mL) followed by dichloromethane (10 mL) were added to the reaction mixture and the organic layer was separated, dried on sodium sulphate, filtered and concentrated under reduced pressure. The residue was purified by column chromatography using silica gel to give the compound 12k as a solid (233 mg, 57.50%). HPLC: 99.04% (Rt=12.33 min).

$^1$H NMR (CDCl$_3$, 200 MHz) δ: 8.59 (1H, d, J=8.4 Hz), 8.37 (1H, d, J=8.4 Hz), 8.21 (1H, d, J=7.4 Hz), 7.80 (1H, s), 7.55 (2H, m), 7.19 (1H, d, J=7.4 Hz), 3.80 (3H, s), 3.62 (4H, t, J=5.6 Hz), 3.32 (4H, t, J=5.6 Hz), 2.88 (6H, s). MS (m/z): 460 (M+1).

Preparation of 2-[4-(5-dimethylamino-naphthalene-1-sulfonyl)-piperazin-1-yl]-thiazole-5-carboxylic acid hydroxyamide (13k)

To a solution of compound (12k) (125 mg, 0.270 mmol) in 1,4-dioxane (2 mL) were added hydroxylamine hydrochloride (187 mg, 2.70 mmol) and a freshly prepared solution of sodium methoxide in methanol (92 mg, 4.00 mmol of sodium dissolved in 1 mL of methanol) under a $N_2$ atmosphere. The reaction mixture was stirred at room temperature for 2 h (progress of the reaction was monitored by TLC analysis). The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 13k (10 mg, yield 8.0%). HPLC: 90.69% (Rt=12.77 min).

$^1$H NMR (CD$_3$OD, 200 MHz) δ: 8.12 (2H, m), 8.33 (1H, m), 7.86-7.59 (4H, m), 3.62 (4H, m), 3.36 (4H, m), 3.16 (6H, s).

Example 15

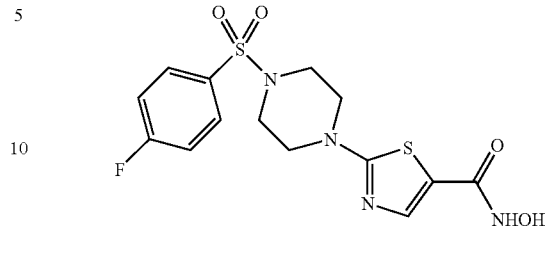

Preparation of 2-[4-(4-fluoro-benzene-sulfonyl)-piperazin-1-yl]-thiazole-5-carboxylic acid methyl ester (12m)

To a solution of compound 11 (200 mg, 0.886 mmol) in dichloromethane (7.5 mL) were added 4-fluorobenzenesulfonyl chloride (256 mg, 1.320 mmol) and triethylamine (220 mg, 2.169 mmol) under a $N_2$ atmosphere. The reaction mixture was stirred at room temperature for 4 h. Water (10 mL) followed by dichloromethane (10 mL) were added to the reaction mixture and the organic layer was separated, dried on sodium sulfate, filtered and concentrated under reduced pressure. The residue was purified by column chromatography using silica gel to give the compound 12m as a solid (300 mg, 88.4%). HPLC: 86.16% (Rt=7.72 min).

$^1$H NMR (CDCl$_3$, 200 MHz) δ: 7.82 (1H, s), 7.78-7.75 (2H, m), 7.23 (2H, d, J=8.8 Hz), 3.81 (3H, s), 3.69 (4H, t, J=4.8 Hz), 3.14 (4H, t, J=4.8 Hz). MS (m/z): 385(M+1), 101.

Preparation of 2-[4-(4-fluoro-benzenesulfonyl)-piperazin-1-yl]-thiazole-5-carboxylic acid hydroxyamide (13m)

To a solution of compound (12m) (125 mg, 0.320 mmol) in 1,4-dioxane (2 mL) were added hydroxylamine hydrochloride (225 mg, 3.20 mmol) and a freshly prepared solution of sodium methoxide in methanol (110 mg, 4.80 mmol of sodium dissolved in 1 mL of methanol) under a $N_2$ atmosphere. The reaction mixture was stirred at room temperature for 2 h (progress of the reaction was monitored by TLC analysis). The reaction mixture was acidified to pH~6 with 1M HCl and the formed precipitates were filtered off. The filtrate was diluted with ethylacetate (5 mL) and water (2 mL) and the organic layer was separated. The aqueous layer was washed with ethylacetate (5 mL) and the combined organic layers were dried on sodium sulphate, filtered and concentrated under reduced pressure. The residue was purified by preparative HPLC to give 13m. HPLC: (Rt=3.89 min).

Scheme 9

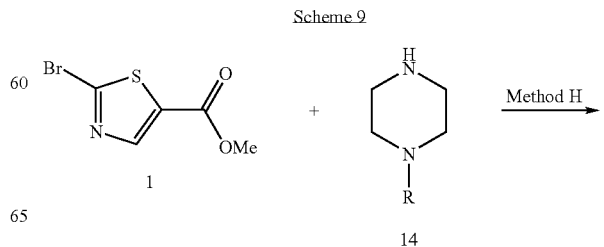

-continued

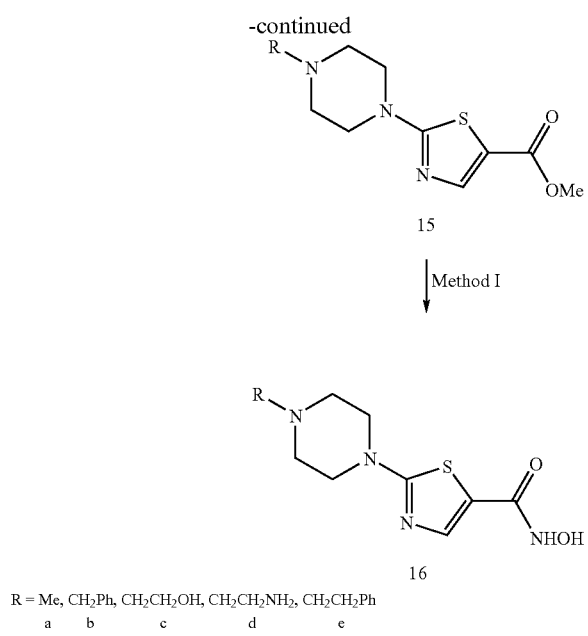

15

↓ Method I

16

R = Me, CH₂Ph, CH₂CH₂OH, CH₂CH₂NH₂, CH₂CH₂Ph
  a    b     c        d         e

Example 16

Preparation of 2-(4-methyl-piperazin-1-yl)-thiazole-5-carboxylic acid methyl ester (15a)

To a solution of methyl 2-bromothiazole-5-carboxylate 1 (222 mg, 1.00 mmol) in acetonitrile (20 mL) were added N-methyl piperazine 14a (120 mg, 1.20 mmol) and potassium carbonate (152 mg, 1.10 mmol) under a $N_2$ atmosphere. The reaction mixture was heated to reflux at 80° C. for 10 h. The reaction mixture was filtered through Celite and the filtrate was concentrated under reduced pressure. The residue was purified by column chromatography using silica gel to give the compound 16a (188 mg, 78.1%).

$^1$H NMR (CD₃OD, 200 MHz) δ: 7.93 (1H, s), 3.83 (3H, s), 3.67 (4H, m), 2.75 (4H, t, J=5.0 Hz), 2.49 (3H, s). MS (m/z): 242 (M+1).

Preparation of 2-(4-methyl-piperazin-1-yl)-thiazole-5-carboxylic acid hydroxyamide (16a)

To a solution of compound 15a (125 mg, 0.518 mmol) in 1,4-dioxane (2 mL) were added hydroxylamine hydrochloride (360 mg, 5.18 mmol) and a freshly prepared solution of sodium methoxide in methanol (178 mg, 7.72 mmol of sodium dissolved in 1.5 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 16a. HPLC: (Rt=10.74 min).

Example 17

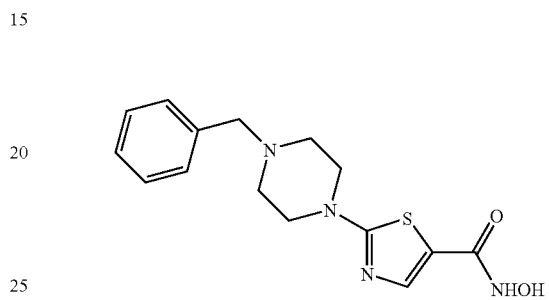

Preparation of 2-(4-Benzyl-piperazin-1-yl)-thiazole-5-carboxylic acid methyl ester (15b)

To a solution of methyl 2-bromothiazole-5-carboxylate 1 (222 mg, 1.00 mmol) in acetonitrile (20 mL) were added N-benzyl piperazine 14b (211 mg, 1.20 mmol) and potassium carbonate (152 mg, 1.10 mmol) under a $N_2$ atmosphere. The reaction mixture was heated to reflux at 80° C. for 10 h. The reaction mixture was filtered through Celite and the filtrate was concentrated under reduced pressure. The residue was purified by column chromatography using silica gel to give the compound 15b (229 mg, 72.7%).

$^1$H NMR (CD₃OD, 200 MHz) δ: 7.87 (1H, s), 7.40 (5H, m), 3.84 (3H, s), 3.61 (6H, m), 2.60 (4H, t, J=5.0 Hz). MS (m/z): 318 (M+1).

Preparation of 2-(4-Benzyl-piperazin-1-yl)-thiazole-5-carboxylic acid hydroxyamide (16b-hydroxamate)

To a solution of compound 15b (125 mg, 0.394 mmol) in 1,4-dioxane (2 mL) were added hydroxylamine hydrochloride (273 mg, 3.94 mmol) and a freshly prepared solution of sodium methoxide in methanol (136 mg, 5.911 mmol of sodium dissolved in 1.5 mL of methanol) under $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 16b.

HPLC: (Rt=4.45 min).

Example 18

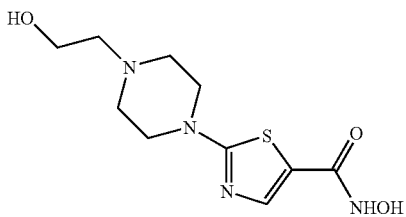

Preparation of 2-[4-(2-hydroxyethyl)-piperazin-1-yl]-thiazole-5-carboxylic acid methyl ester (15c)

To a solution of methyl 2-bromothiazole-5-carboxylate 1 (222 mg, 1.00 mmol) in acetonitrile (20 mL) were added N-(2-hydroxyethyl)piperazine 14c (156 mg, 1.20 mmol) and potassium carbonate (152 mg, 1.10 mmol) under a $N_2$ atmosphere. The reaction mixture was heated to reflux at 80° C. for 10 h. The reaction mixture was filtered through Celite and the filtrate was concentrated under reduced pressure. The residue was purified by column chromatography using silica gel to give the compound 15c (185 mg, 68.2%).

$^1$H NMR (CD$_3$OD, 200 MHz) δ: 7.81 (1H, s), 3.79 (3H, s), 3.70 (2H, t, J=5.4Hz), 3.63 (4H, t, J=5.6 Hz), 2.70 (6H, m). MS (m/z): 272 (M+1).

Preparation of 2-(4-(2-hydroxyethyl)-piperazin-1-yl)-thiazole-5-carboxylic acid hydroxyamide (16c)

To a solution of compound 15c (125 mg, 0.461 mmol) in 1,4-dioxane (2 mL) were added hydroxylamine hydrochloride (320 mg, 4.61 mmol) and a freshly prepared solution of sodium methoxide in methanol (159 mg, 6.91 mmol of sodium dissolved in 1.5 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 16c.

HPLC: (Rt=2.97 min).

Example 19

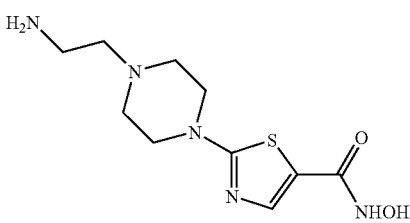

Preparation of 2-[4-(2-aminoethyl)-piperazin-1-yl]-thiazole-5-carboxylic acid methyl ester (15d)

To a solution of methyl 2-bromothiazole-5-carboxylate 1 (222 mg, 1.00 mmol) in acetonitrile (20 mL) were added N-(2-amino ethyl)piperazine 14d (155 mg, 1.20 mmol) and potassium carbonate (152 mg, 1.10 mmol) under a $N_2$ atmosphere. The reaction mixture was heated to reflux at 80° C. for 10 h. The reaction mixture was filtered through Celite and the filtrate was concentrated under reduced pressure. The residue was purified by column chromatography using silica gel to give the compound 15d (176 mg, 65.2%).

$^1$H NMR (CD$_3$OD, 200 MHz) δ: 7.82 (1H, s), 7.23 (5H, m), 3.81 (3H, s), 3.60 (4H, t, J=5.0 Hz), 2.90-2.63 (8H, m).

Preparation of 2-(4-(2-aminoethyl)-piperazin-1-yl)-thiazole-5-carboxylic acid hydroxyamide (16d)

To a solution of compound 15d (125 mg, 0.462 mmol) in 1,4-dioxane (2 mL) were added hydroxylamine hydrochloride (321 mg, 4.62 mmol) and a freshly prepared solution of sodium methoxide in methanol (159 mg, 6.91 mmol of sodium dissolved in 1.5 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethylacetate (5 mL) and water (2 mL) and the organic layer was separated. The aqueous layer was washed with ethylacetate (5 mL) and the combined organic layers were dried on sodium sulphate, filtered and concentrated under reduced pressure. The residue was purified by preparative HPLC to give 16d.

HPLC: (Rt=2.93 min).

Example 20

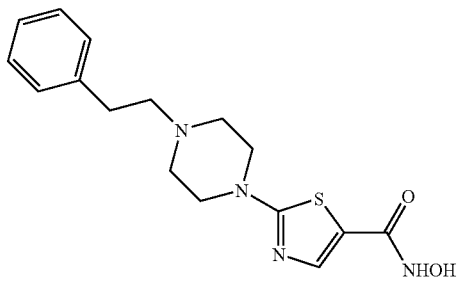

Preparation of 2-[4-phenylethyl-piperazin-1-yl]-thiazole-5-carboxylic acid methyl ester (15e)

To a solution of methyl 2-bromothiazole-5-carboxylate 1 (222 mg, 1.00 mmol) in acetonitrile (20 mL) were added N-phenyl ethyl piperazine 14e (228 mg, 1.20 mmol) and potassium carbonate (152 mg, 1.10 mmol) under a $N_2$ atmosphere. The reaction mixture was heated to reflux at 80° C. for 10 h. The reaction mixture was filtered through Celite and the filtrate was concentrated under reduced pressure. The residue was purified by column chromatography using silica gel to give the compound 15e (245 mg, 66.4%).

$^1$HNMR(CD$_3$OD, 200 MHz): δ 7.78 (1H, s), 3.81 (3H, s), 3.62 (4H, m), 2.77-2.31 (8H, m).

Preparation of 2-(4-phenylethyl-piperazin-1-yl)-thiazole-5-carboxylic acid hydroxyamide (16e)

To a solution of compound 15e (125 mg, 0.377 mmol) in 1,4-dioxane (2 mL) were added hydroxylamine hydrochloride (262 mg, 3.77 mmol) and a freshly prepared solution of sodium methoxide in methanol (130 mg, 5.655 mmol of sodium dissolved in 1.5 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 16e.

HPLC: (Rt=13.41 min).

Example 20B

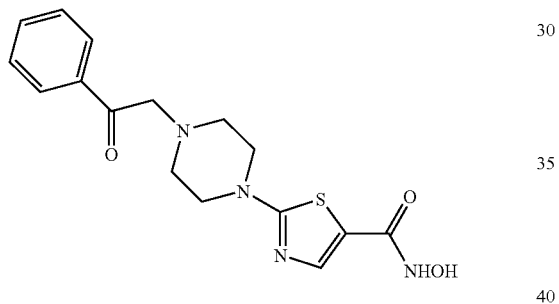

2-(4-(2-oxo-2-phenylethyl)-piperazin-1-yl)-1,3-thiazole-5-carboxylic acid hydroxyamide A mixture of intermediate ester 11 (Scheme 8) (115 mg, 0.504 mmol), α-bromoacetophenone (128 mg, 0.604 mmol), cesium carbonate (326 mg, 1.0 mmol) and DCM was stirred at room temperature for 12 hours. The reaction was poured into water and extracted with DCM (20 mL). The solvent was dried, the solvent evaporated, and the residue chromatographed using 50% ethyl acetate in hexanes to give the intermediate alkylated ester (120 mg, 67%); MS=360 (M+H$^+$).

The alkylated ester (100 mg, 0.278 mmol) in methanol (5 mL) at 0° C. was treated with 50% aqueous hydroxylamine (1 mL) and aqueous sodium hydroxide (80 mg in 0.5 mL of water) and stirred for 4 hours. The reaction was acidified with hydrochloric acid (6N) and the solvent was removed to obtain a solid that was purified by preparative HPLC to give Example 20B. $^1$H NMR (CDCl$_3$, 300 MHz) δ: 7.69 (d, J=8.1 Hz, 2H), 7.28 (d, J=8.1 Hz, 2H), 4.57 (s, 2H), 3.74 (m, 4H), 3.37 (m, 4H), 2.27 (s, 3H).

Scheme 10

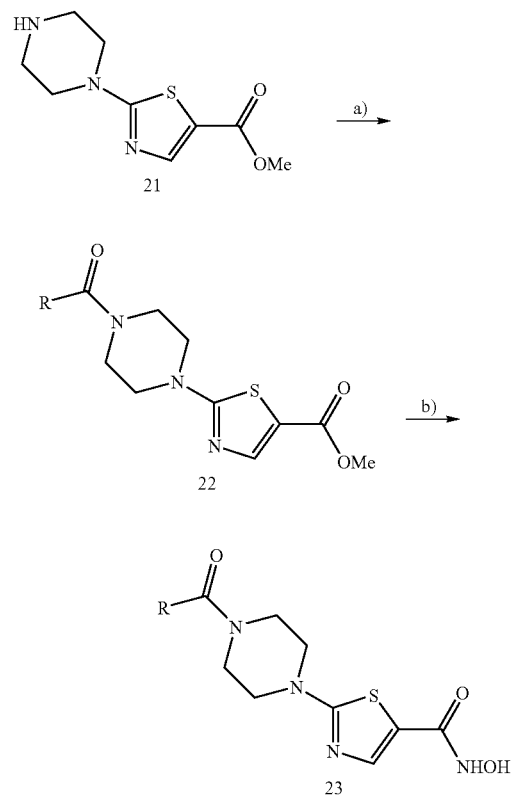

Example 21

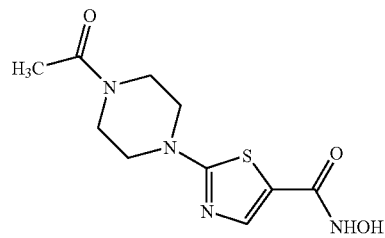

Preparation of 2-(4-acetyl-piperazin-1-yl)-thiazole-5-carboxylic acid methyl ester (22a)

$^1$H NMR (CDCl$_3$, 200 MHz) δ: 7.82 (1H, s), 3.84 (3H, s), 3.77 (4H, t, J=5.4 Hz), 3.54 (4H, t, J=5.4 Hz), 2.15 (3H, s).

Preparation of 2-(4-acetyl-piperazin-1-yl)-thiazole-5-carboxylic acid hydroxamide (23a)

To a solution of compound 22a (100 mg, 0.300 mmol) in 1,4-dioxane (2 mL) were added hydroxylamine hydrochloride (208 mg, 2.991 mmol) and a freshly prepared solution of sodium methoxide in methanol (103 mg, 4.511 mmol of sodium dissolved in 1.5 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 23a. HPLC: Rt=4.42 min.

Example 22

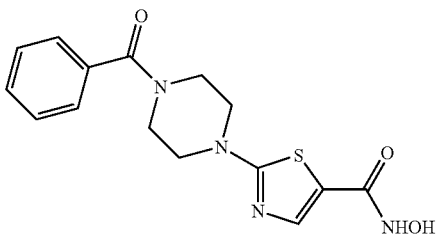

Preparation of 2-(4-benzoyl-piperazin-1-yl)-thiazole-5-carboxylic acid methyl ester (22b)

To a solution of compound 21 (200 mg, 0.886 mmol) in dichloromethane (7.5 mL) were added benzoyl chloride (148 mg, 1.056 mmol) and triethylamine (106 mg, 1.047 mmol) under a $N_2$ atmosphere. The reaction mixture was stirred at room temperature for 4 h (progress of the reaction was monitored by TLC analysis). Water (10 mL) followed by dichloromethane (10 mL) were added to the reaction mixture and the organic layer was separated, dried on sodium sulfate, filtered and concentrated under reduced pressure. The residue was purified by column chromatography using silica gel to give the compound 22b (180 mg, yield 61.8%).

Preparation of 2-(4-benzoyl-piperazin-1-yl)-thiazole-5-carboxylic acid hydroxamide (23b)

To a solution of compound 22b (100 mg, 0.321 mmol) in 1,4-dioxane (2 mL) were added hydroxylamine hydrochloride (222 mg, 3.191 mmol) and a freshly prepared solution of sodium methoxide in methanol (110 mg, 4.712 mmol of sodium dissolved in 1.5 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 23b. HPLC: Rt=3.69 min.

Example 23

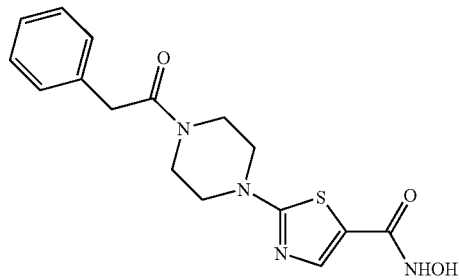

Preparation of 2-(4-phenylacetyl-piperazin-1-yl)-thiazole-5-carboxylic acid methyl ester (22c)

To a solution of compound 21 (200 mg, 0.886 mmol) in dichloromethane (7.5 mL) were added phenyl acetyl chloride (162 mg, 1.056 mmol) and triethylamine (106 mg, 1.047 mmol) under a $N_2$ atmosphere. The reaction mixture was stirred at room temperature for 4 h (progress of the reaction was monitored by TLC analysis). Water (10 mL) followed by dichloromethane (10 ml) were added to the reaction mixture and the organic layer was separated, dried on sodium sulfate, filtered and concentrated under reduced pressure. The residue was purified by column chromatography using silica gel to give the compound 22c (130 mg, yield 42.9%). HPLC: 99.40 0% (Rt=11.93 min).
$^1$H NMR (CDCl$_3$, 200 MHz) δ: 7.85 (1H, s), 7.27(5H, m), 3.82 (3H, s), 3.73 (4H, m), 3.51 (4H, m), 3.34 (2H, m).

Preparation of 2-(4-phenylacetyl-piperazin-1-yl)-thiazole-5-carboxylic acid hydroxamide (23c)

To a solution of compound 22c (100 mg, 0.377 mmol) in 1,4-dioxane (2 mL) were added hydroxylamine hydrochloride (208 mg, 3.771 mmol) and a freshly prepared solution of sodium methoxide in methanol (103 mg, 4.471 mmol of sodium dissolved in 1.5 mL of methanol) under a $N_2$ atmosphere. The reaction mixture was stirred at room temperature for 2 h. The reaction mixture was acidified to pH~6 with 1M HCl and the formed precipitates were filtered off. The filtrate was diluted with ethyl acetate (5 mL) and water (2 mL) and the organic layer was separated. The aqueous layer was washed with ethyl acetate (5 mL) and the combined organic layers were dried on sodium sulfate, filtered and concentrated under reduced pressure. The residue was purified by preparative HPLC to give 23c. HPLC: Rt=5.62 min.

Example 23b

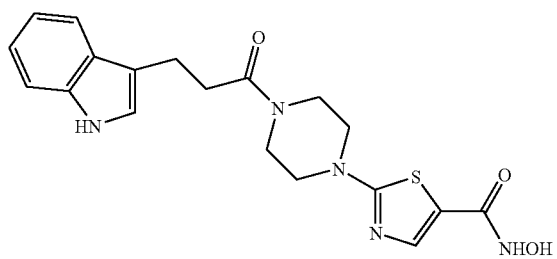

2-[4-(3-{1H-indol-3-yl}propanoyl)-piperazin-1-yl]-1,3-thiazole-5-carboxylic acid hydroxyamide To a solution of 21 (100 mg, 0.440 mmol) in tetrahydrofuran (10 mL) was added EDCI (92 mg, 0.480 mmol), 1-hydroxy-7-azabenzotriazole (HOAT) (65 mg, 0.478 mmol), DIEA (75 mg, 0.564 mm) and indole-3-propionic acid (83 mg, 0.440 mmol) under $N_2$ atmosphere. The reaction mixture was stirred at room temperature for 12 h. Water (10 mL) followed by dichloromethane (10 mL) were added to the reaction mixture and the organic layer was separated, dried over sodium sulfate, filtered and concentrated under reduced pressure. The residue obtained was purified by column chromatography using silica gel to obtain compound amide 22 (120 mg). $^1$H NMR (CDCl$_3$, 200 MHz) δ: 7.99 (1H, s), 7.85 (1H, s), 7.63-7.05 (5H, m), 3.83 (3H, s), 3.74 (4H, t, J=5.2 Hz), 3.42 (4H, t, J=5.2 Hz), 3.18 (2H, t, J=7.2 Hz), 2.75 (2H, t, J=7.2 Hz).

To a solution of the amide 22 (100 mg, 0.25 mmol) in 1,4-dioxane (2 mL) were added hydroxylamine hydrochloride (174 mg, 2.51 mmol) and a freshly prepared solution sodium methoxide in methanol (86 mg, 3.73 mmol of sodium dissolved in 1.5 mL of methanol) under $N_2$ atmosphere. The reaction mixture was stirred at room temperature for 2 h. The reaction mixture was acidified to pH~6 with 1M HCl and the precipitates were filtered off. The filtrate was diluted with ethylacetate (5 mL) and water (2 mL) and the organic layer was separated. The aqueous layer was washed with ethylacetate (5 mL) and the combined organic layers were dried on sodium sulfate, filtered and concentrated under reduced pressure. The residue was purified by preparative HPLC to give Example 23b; m/e=400(M+H$^+$).

Example 24

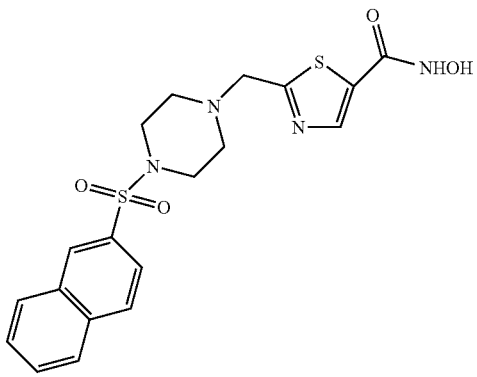

Preparation of N-(2-napthylsulfonyl)piperazine (25)

A solution of N-tert-butyoxycarbonylpiperazine (2a) (1.86 g) in DCM (100 mL) and N,N-di-2-propyl-ethylamine (2 mL) was cooled in ice-water as a solution of 2-naphthalenesulfonylchloride (2.27 g) in DCM (50 mL) was added drop-wise. After addition, the cooling was removed and the reaction stirred overnight. The solvent was evaporated and the residue partitioned between water and ethyl acetate. The Scheme 11

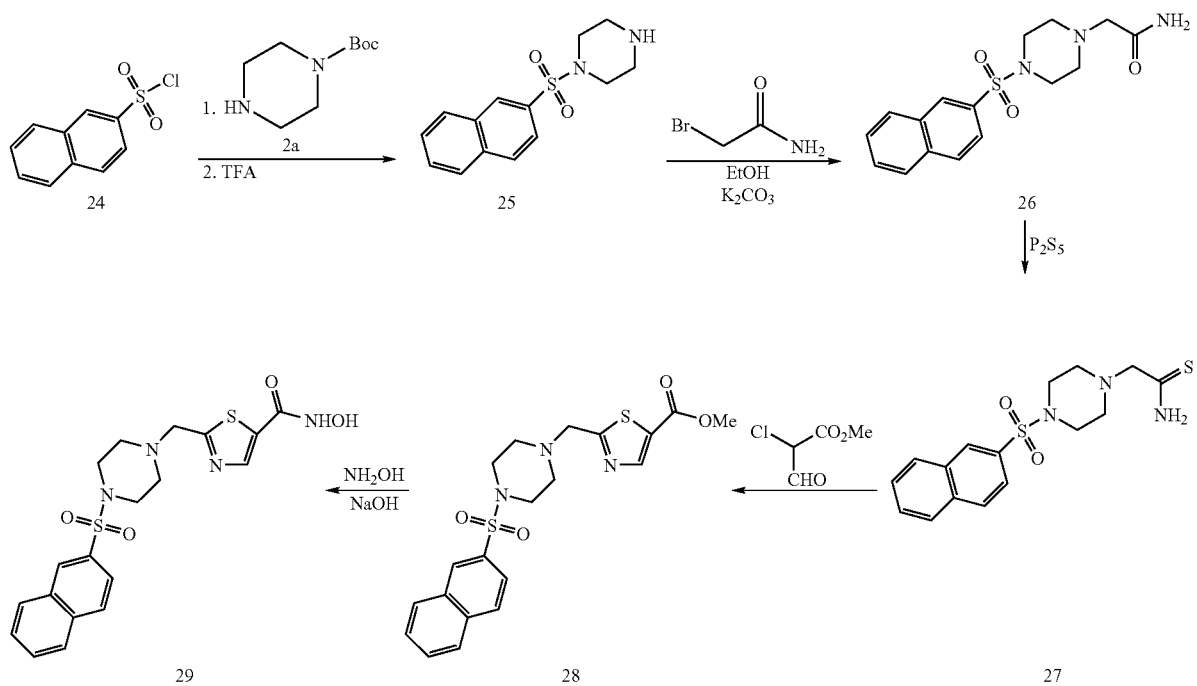

organic phase was sequentially washed with 0.5 N hydrochloric acid, water, saturated aqueous sodium bicarbonate and brine. After drying, the solvent was evaporated to provide a white solid. The white solid was dissolved in DCM (35 mL) and treated with trifluoroacetic acid (15 mL). After one hour, the solvent was evaporated, the residue suspended in water and the solution made basic with 1 N sodium hydroxide. The mixture was extracted with ethyl acetate. The extracts were washed with water, dried, and the solvent evaporated to give a white solid (2.7 g).

$^1$H NMR (CD$_3$OD, 300 MHz) δ: 8.41 (s, 1H), 8-8.13 (3H, m), 7.6-7.8 (3H, m), 3.17-3.21 (4H, m), 3.09-3.13 (4H, m).

Preparation of N-(2-naphthylsulfonyl)-N'-(2-acetamido)piperazine (26)

A mixture of 25 (2.2 g), 2-bromoacetamide (1.15 g) potassium carbonate (1.16 g) and ethanol (40 mL) was heated to reflux overnight. The solvent was evaporated and the residue suspended in water and stirred for 30 minutes. The solid was collected by filtration and thoroughly dried to give a white solid (2.8 g).

$^1$H NMR (CD$_3$OD, 300 MHz) δ: 8.39 (s, 1H), 7.99-8.11 (m, 3H), 7.63-7.79 (m, 3H), 3.14 (m, 4H), 2.98 (s, 2H), 2.60 (t, 4H).

Preparation of N-(2-naphthylsulfonyl)-N'-(2-thioacetamido)piperazine (27)

A suspension of 26 (0.94 g) in tetrahydrofuran (10 mL) was stirred as phosphorus pentasulfide (1.89 g) was added in portions. The reaction was then heated to reflux for one hour. The solvent was decanted and the solid residue triturated with tetrahydrofuran. The solvent was evaporated from the extracts and the residue purified by flash chromatography on 30 g of silica gel eluting with 1:1 ethyl acetate:hexane. The desired component was finally eluted with 60% ethyl acetate-hexane. Evaporation of the pure fractions gave a white solid (0.23 g).

$^1$H NMR (CD$_3$OD, 300 MHz) δ: 8.27 (s, 1H), 7.88-8.0 (m, 3H), 7.52-7.68 (m, 3H), 3.23 (s, 2H), 3.03 (m, 4H), 2.46 (t, 4H). MS (EI+): 350 (m+1).

Preparation of methyl chloro(formyl)acetate

Methyl chloroacetate (3.2 g) and methyl formate (1.8 g) were dissolved in toluene (5 mL) and the mixture was cooled in ice-water. Sodium methoxide (2 g) was added in portions and the reaction stirred for five hours. The reaction was quenched with water (100 mL) and the mixture was extracted with toluene (100 mL) and ether (100 mL). The aqueous layer was separated, cooled in ice-water, and the pH of the solution adjusted to 4 using 6 N hydrochloric acid. The aqueous layer was then extracted with ethyl acetate. The organic extracts were dried and the solvent thoroughly evaporated to give a tacky solid (2 g) that was used without further purification. TLC on silica gel eluting with 1:1 ethyl acetate:hexane shows two spots R$_f$=0.36 and 0.38.

Preparation of N-(2-naphthylsulfonyl)-N'-[2-(5-carbomethoxy)thiazolyl]piperazine (28)

A mixture of 27 (84 mg) and methyl chloro(formyl) acetate (180 mg) in toluene (3 mL) was heated to reflux for three hours. The reaction was diluted with ethyl acetate and washed sequentially with aqueous, saturated sodium bicarbonate, 10% aqueous potassium carbonate and water. The organic layer was dried and the solvent evaporated to give a brown, oily residue. The residue was purified by flash chromatography on silica gel (15 g) eluting with 1:1 ethyl acetate:hexane. The desired fractions were eluted with 60% ethyl acetate-hexane. Evaporation of the purest fraction gave a brown glass (40 mg).

$^1$H NMR (CDCl$_3$, 300 MHz) δ: 8.33 (s, 1H), 8.23 (s, 1H), 7.92-8.0 (m, 3H), 7.6-7.76 (m, 3H), 3.836 (s, 3H), 3.828 (s, 2H), 3.15 (m, 4H), 2.71 (m, 4H). MS (EI+): 432 (m+1).

Preparation of N-(2-naphthylsulfonyl)-N'-{2-[5-(N-hydroxycarboxamido)]thiazolyl}piperazine (29)

A solution of 28 (32 mg) in ethanol (1.5 mL) was cooled in ice-water. A solution of 50% aqueous hydroxylamine (50 μL) was added followed by 1 N sodium hydroxide (53 μL). After four hours, the cooling was stopped and the reaction stirred overnight. Additional 50% hydroxylamine (25 μL) and 1 N sodium hydroxide (20 μL) were added and stirring continued for eight hours. The reaction was neutralized with 1 N hydrochloric acid (70 μL) and the solvent was evaporated to give a yellowish solid. This product was purified by HPLC using a 19×50 mm C-18 column eluting with a ten minute linear gradient that started with 100% water-0.1% trifluoroacetic acid and ended with 30% water-0.1% trifluoroacetic acid/70% acetonitrile-0.1% trifluoroacetic acid. The pure fractions of the component eluting at 4.8 minutes were freeze dried to give a white solid (0.1 mg).

MS (EI+): 433 (m+1).

Scheme 12

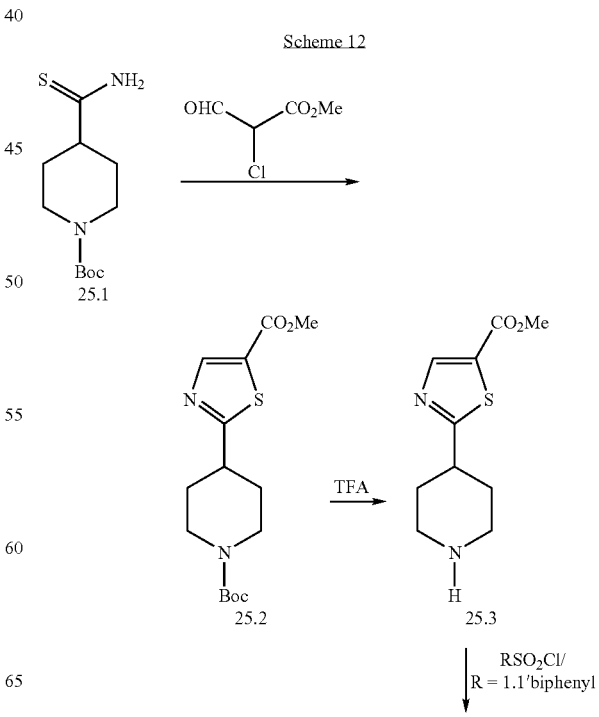

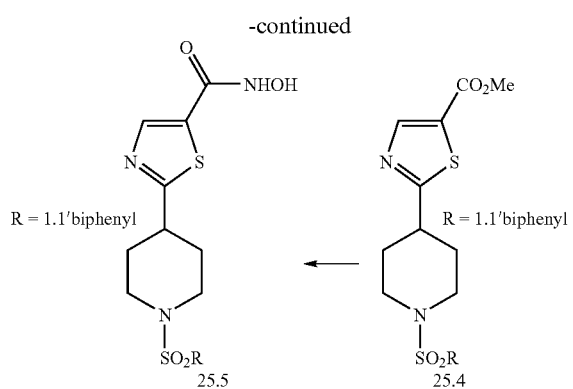

Example 25

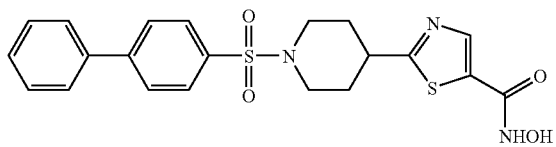

2-[1-(1,1'-biphenyl-4-ylsulfonyl)piperidin-4-yl]-1,3-thiazole-5-carboxylic acid hydroxyamide A mixture of tertiary butyl 4-(aminocarbothioyl)tetrahydropyridne-1(2H)carboxylate 25.1 (1 g) and methyl chloro(formyl)acetate (1.3 g) in toluene (20 mL) was heated in an 80°-90° C. oil bath for 1.75 hours. Another spatula full of the chloro(formyl)acetate was added and the heating continued another hour. The reaction was cooled and partitioned between saturated aqueous sodium bicarbonate and ethyl acetate. The organics were washed with water and brine. Drying and evaporation of the solvent gave an oily residue that was purified by flash chromatography eluting with 30% ethyl acetate-hexane to give the thiazole 25.2 as a yellow oil (0.6 g).

A solution of 25.2 (0.55 g) in methylene chloride (3 mL) was treated with trifluoroacetic acid (1 mL). After three hours, another portion of trifluoroacetic acid (1 mL) was added and stirring continued for three hours. The solvent was evaporated and the residue partitioned between water and ether. The aqueous phase was made basic with 1 N sodium hydroxide and extracted with chloroform. The chloroform solution was dried and the solvent evaporated to give 25.3 as a dark gum (0.187 g). A solution of the gum in methylene chloride (5 mL) and diisopropylethylamine (0.3 mL) was cooled in ice-water and treated with 4-biphenylsulphonyl chloride (0.21 g) in methylene chloride (2 mL). The cooling was removed and the reaction stirred one hour. A crystal of 4-dimethylaminopyridine was added and stirring was continued overnight. The solvent was evaporated and the residue partitioned between water and ethyl acetate. The organics were washed with 1 N hydrochloric acid, aqueous saturated sodium bicarbonate, and brine. The solvent was dried and evaporated to give a tan solid. The solid was purified by flash chromatography eluting with 60-80% ethyl acetate-hexane to give 25.3 as a tan powder (91 mg) with the expected m/e of 443 (M+H$^+$).

A mixture of methyl 2-[1-(1,1'-biphenyl-4-ylsulfonyl)piperidin-4-yl]-1,3-thiazole-5-carboxylate 25.3 (9 mg), 50% hydroxylamine in water (0.05 mL), and dioxane (1 mL) were cooled in ice-water. To the reaction was added 1N sodium hydroxide (0.053 mL) followed by removal of the cooling bath. After stirring overnight, the reaction was neutralized with 1 N hydrochloric acid (0.053 mL) and the solvent evaporated. The residue was purified by preparative hplc to give Example 25 as a flocculant white solid (3.5 mg). $^1$H NMR (DMSO) δ: 2.75 (m, 2H), 2.15 (m, 2H), 2.5 (m, 2H), 3.1 (m, 1H), 3.75 (m, 2H), 7.45-7.55 (m, 3H), 7.72-7.96 (m, 6H), 8.08 (s, 1H), 11.3 (s, 1H); m/e=444 (M+H$^+$).

BIOLOGICAL EXAMPLES

Example A

In Vitro Fluorescent Histone Deacetylase Assay

Histone deacetylase (HDAC) activity assays were performed using the HDAC fluorescent activity assay/drug discovery kit (Biomol Research Laboratories, Plymouth Meeting, Pa.) essentially according to the manufacturer's instructions. The included HeLa cell nuclear extract, which contains a mosaic of HDAC enzymes and other nuclear factors, was used as the source of HDAC activity. The final substrate concentration in the assay mixture was 50 μM. The reaction was allowed to proceed for 10 min at room temperature before stopping the reaction. Test compounds were prepared as 20 mM stock solutions in DMSO (Molecular Biology grade, Sigma-Aldrich Co., St. Louis, Mo.) and stored at −70° C. Serial dilutions of test compounds were prepared in assay buffer immediately prior to testing. DMSO was determined in a separate trial to have no significant effect on the activity of this assay at concentrations up to 5%; the final DMSO concentration in the wells was no more than 2% and therefore DMSO effects were safely neglected. Assays were performed in white polystyrene 96-well half-area assay plates (Corning, Corning, N.Y.) and measured on a Wallace 1420 fluorescent plate reader (Wallac Oy, Turku, Finland) with an excitation wavelength of 355 nm, an emission wavelength of 460 nm, and a 1 sec signal averaging time.

In some assays recombinant HDAC8 (Biomol) was used as the source of the enzyme activity; here the final substrate concentration was 250 μM, the final concentration of HDAC8 was 0.02 u/μL and the reaction was allowed to proceed at 37° C. for 1 h before stopping. For all curves, IC$_{50}$ values were calculated with the GraFit curve-fitting program (Erithacus, Horley, Surrey, UK).

The HDAC inhibition data for representative examples of this invention is presented in Table 1.

TABLE 1

| HDAC inhibition potencies for selected examples of the present invention | | | |
|---|---|---|---|
| Example No. | IC$_{50}$ HDAC Inhibition (μM) | Example No. | IC$_{50}$ HDAC Inhibition (μM) |
| 2 | 5.9 | 5d | 8.4 |
| 4 | 0.045 | 5e | 2.15 |
| 4b | 0.44 | 5f | 18.8 |
| 4c | 0.16 | 5g | 0.6 |
| 4d | 0.4 | 5h | 0.67 |
| 4e | 3.24 | 16 | 671 |
| 4f | 0.55 | 17 | 755 |
| 4g | 14.5 | 18 | 7.7 |

TABLE 1-continued

HDAC inhibition potencies for selected examples of the present invention

| Example No. | IC$_{50}$ HDAC Inhibition (µM) | Example No. | IC$_{50}$ HDAC Inhibition (µM) |
|---|---|---|---|
| 4h | 1.63 | 20 | 118 |
| 4i | 0.65 | 20B | 0.33 |
| 4j | 11.4 | 21 | 2.75 |
| 4k | 318 | 22 | 3.5 |
| 4m | 4.7 | 23 | 31.6 |
| 5 | 0.05 | 23b | 0.87 |
| 5b | 4.7 | 24 | 6.9 |
| 5c | 12.6 | 25 | 13.1 |

Example B

Whole Cell Cytotoxicity Assay: Sulforhodamine B

The following procedure can be found on the Developmental Therapeutics Program NCI/NIH web site at http://dtp.nci.nih.gov/brancehes/btb/ivclsp.html.

1. Human tumor cell lines of HT29, A549 and MCF7 are grown in DMEM containing 10% fetal bovine serum and 2 mM L-glutamine. Cells are plated in a 96 well plate at a density of 5000 cells per well in 100 µL of growth medium and incubated at 37° C., 5% CO$_2$, for 24 hours prior to the addition of experimental compounds.

2. Experimental drugs are solubilized in DMSO for a final concentration of 20 mM immediately prior to use. Drugs are further diluted in growth media for a total of nine drug concentrations and a growth control. At the 24-hour time point, one plate of cells is fixed in situ with TCA as a measurement of the cell population at time zero, or the time of drug addition.

3. The plates are further incubated with drug for an additional 48 hours.

4. The cells are fixed in situ by gently aspirating off the culture media and then adding 50 µL of ice cold 10% TCA per well and incubated at 4° C. for 60 minutes. The plates are washed with tap water five times and allowed to air dry for 5 minute.

5. 50 µl of a 0.4% (w/v) Sulforhodamine B solution in 1% (v/v) acetic acid is added per well and incubated for 30 minutes at room temperature.

6. Following staining, plates are washed five times with 1% acetic acid to remove any unbound dye and then allowed to air dry for 5 minutes.

7. Stain is solubilized with 100 µL of 10 mM Tris pH 10.5 per well and placed on an orbital rotator for 5 minutes.

8. Absorbance is read at 570 nm. Representative GI$_{50}$'s against MCF7 cells for selected examples of this invention are shown in Table 2.

TABLE 2

Activity of selected examples of this invention against MCF7 cells

| Example No. | GI$_{50}$ in MCF7 cells (µM) | Example No. | GI$_{50}$ in MCF7 cells (µM) |
|---|---|---|---|
| 2 | 10 | 5d | 15 |
| 4 | 0.7 | 5e | 2 |
| 4b | 3 | 5f | 20 |
| 4c | 4 | 5g | 8 |
| 4d | 1 | 5h | 3.5 |
| 4e | 6 | 16 | |
| 4f | 2 | 17 | 4 |
| 4g | 3 | 18 | |
| 4h | 5 | 20 | |
| 4i | 18 | 20B | 4 |
| 4j | 1.5 | 21 | |
| 4k | 4 | 22 | 40 |
| 4m | 2.5 | 23 | 20 |
| 5 | 6 | 23b | 30 |
| 5b | 10 | 24 | 10 |
| 5c | | 25 | 100 |

What is claimed is:

1. A compound of the formula:

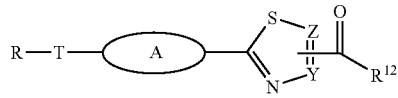

wherein:

R is selected from the group consisting of hydrogen, aryl, substituted aryl, heteroaryl, substituted heteroaryl, alkyl and substituted alkyl;

$R^{12}$ is selected from the group consisting of —NR$^{14}$OH, —OH, —NR$^{14}$R$^{15}$, —OR$^{14}$, —(C$_1$-C6)alkylene-SR$^{14}$, —(C$_1$-C$_6$)alkylene-OR$^{14}$, —(C$_1$-C$_6$)alkylene-NR$^{14}$R$^{15}$, —CF$_3$;

where $R^{14}$ and $R^{15}$ are independently selected from the group consisting of hydrogen, (C$_1$-C$_6$)alkyl, (C$_1$-C$_6$) substituted alkyl, aryl, substituted aryl and where $R^{14}$ and $R^{15}$ together with the nitrogen atom bound thereto form a heterocyclic or substituted heterocyclic ring;

Y is =C(R$^{11}$)—, and Z is =(R$^{14}$)—; or wherein Y or Z are bonded to C(O)R$^{12}$;

$R^{11}$ is hydrogen or alkyl;

the ring defined by A above is a piperidine or piperazine ring, wherein A is bonded to the five-membered ring of ring A at a nitrogen;

T is —SO$_2$—[(C$_1$-C$_3$)alkylene]$_p$-or, —SO$_2$NR$^{16}$—[(C$_1$-C$_3$)alkylene]$_p$ where p is zero or one and R$^{16}$ is hydrogen, alkyl, aryl, or heteroaryl, provided that when T is connected to A at a nitrogen atom and T is —SO$_2$NR$^{16}$—[(C$_1$-C$_3$)alkylene]$_p$ then p is not zero;

and tautomers and pharmaceutically acceptable salts thereof.

2. A compound according to claim 1, wherein said compound is represented by the formula:

and tautomers, and pharmaceutically acceptable salts thereof.

3. The compound according to claim 2, wherein said compound is represented by the formula:

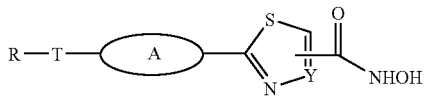

and tautomers, and pharmaceutically acceptable salts thereof.

4. The compound according to claim 3, wherein said compound is represented by the formula:

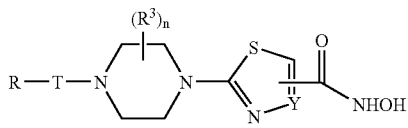

where
each $R^3$ is independently selected from the group consisting of alkyl, substituted alkyl, aryl, substituted aryl, heteroaryl and substituted heteroaryl;
n is zero, one or two; and
tautomers, and pharmaceutically acceptable salts thereof.

5. The compound according to claim 3, wherein said compound is represented by the formula:

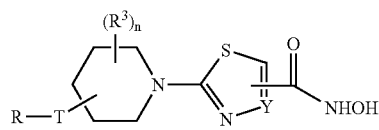

where
each $B^3$ is independently selected from the group consisting of alkyl, substituted alkyl, aryl, substituted aryl, heteroaryl and substituted heteroaryl;
n is zero, one or two; and
tautomers, and pharmaceutically acceptable salts thereof.

6. The compound according to claim 3, wherein R is aryl or substituted aryl.

7. The compound according to claim 3, wherein R is selected from the group consisting of phenyl, naphthyl, 3,4-dimethoxyphenyl, 4-trifluoromethoxyphenyl, 4-methylphenyl, 4-trifluroromethylphenyl, 4-nitrophenyl, 4-acetylphenyl, thiophen-2-yl, biphenyl, 5-(N,N-dimethylamino)-naphthalenyl, 4-fluorophenyl, methyl, benzyl, 2-hydroxyethyl, 2-aminoethyl, and 2-phenylethyl.

8. The compound of claim 3 wherein T is —$SO_2$—, or —$SO_2NHCH_2$—.

9. A compound according to claim 1, which compound is selected from the group consisting of:
1-(2-naphthylsulfonyl)-4-(5-hydroxyaminocarbonylthiazol-2-yl)piperazine;
1-(2-naphthylsulfonyl)-4-(4-hydroxyaminocarbonylthiazol-2-yl)piperazine;
4-(2-naphthylsulfonylamino)-1—[(5-(2-hydroxyaminocarbonyl-thiazol-2-yl)-piperadine;
4-(1,1'-biphenylsulfonylamino)-1—[(5-(2-hydroxyaminocarbonyl-thiazol-2-yl)-piperadine;
4-(3,4-dimethoxyphenylsulfonylamino)-1—[(5-(2-hydroxyaminocarbonyl-thiazol-2-yl)-piperadine;
4-(4-methylphenylsulfonylamino)-1—[(5-(2-hydroxyaminocarbonyl-thiazol-2-yl)-piperadine;
2-(4-{[(1,1'-biphenylsulfonyl)amino]methyl}piperidin-1-yl)-1,3-thiazole-5-carboxylic acid hydroxyamide;
2-{[1-(2-naphthylsulfonyl)piperidin-4-yl]amino}-1,3-thiazole-5-carboxylic acid hydroxyamide;
2-[4-(3,4-dimethoxy-benzene sulfonyl)-piperazin-1-yl]-thiazole-5-carboxylic acid hydroxyamide;
2-[4-(4-trifluoromethoxy-benzene sulfonyl)-piperazin-1-yl]-thiazole-5-carboxylic acid hydroxyamide;
2-[4-(4 toluene-4-sulfonyl)-piperazin-1-yl]-thiazole-5-carboxylic acid hydroxyamide;
2-[4-(4-trifluoromethyl-benzenesulfonyl)-piperazin-1-yl]-thiazole-5-carboxylic acid hydroxyamide;
2-[4-(4-nitro-benzenesulfonyl)-piperazin-1-yl]-thiazole-5-carboxylic acid hydroxyamide;
2-[4-(4-acetyl-benzenesulfonyl)-piperazin-1-yl]-thiazole-5-carboxylic acid hydroxyamide;
2-[4-(thiophene-2-benzenesulfonyl)-piperazin-1-yl]-thiazole-5-carboxylic acid hydroxyamide;
2-[4-(biphenyl-4-sulfonyl)-piperazin-1-yl]-thiazole-5-carboxylic acid hydroxyamide;
2-[4-(5-dimethylamino-naphthalene-1-sulfonyl)-piperazin-1-yl]-thiazole-5-carboxylic acid hydroxyamide;
2-[4-(4-fluoro-benzenesulfonyl)-piperazin-1-yl]-thiazole-5-carboxylic acid hydroxyamide;
N-(2-naphthylsulfonyl)-N'-{2-[5-(N-hydroxycarboxamido)]thiazolyl}-piperazine; and
2-[1-(1,1'-biphenyl-4-ylsulfonyl)piperidin-4-yl]1,3-thiazole-5-carboxylic hydroxyamide;
or pharmaceutically acceptable salts, and tautomers thereof.

10. A pharmaceutical composition comprising an effective amount of a compound according to claim 1, a pharmaceutically inert carrier, and, optionally, at least one other anti-cancer agent selected from the group consisting of platinum coordination compounds, taxane compounds, topoisomerase I inhibitors, topoisomerase II inhibitors, anti-tumour vinca alkaloids, anti-tumour nucleoside derivatives, alkylating agents, anti-tumour anthracycline derivatives, HER2 antibodies, estrogen receptor antagonists, selective estrogen receptor modulators, aromatase inhibitors, retinoids, retinoic acid metabolism blocking agents (RAMBA), DNA methyl transferase inhibitors, kinase inhibitors, farnesyltransferase inhibitors, other HDAC inhibitors, carboplatin, oxalyplatin, paclitaxel, docetaxel, irinotecan, topotecan, etoposide, teniposide, vinbiastine, vincristine, vinorelbine, 5-fluorouracil, gemcitabine, capecitabine, cyclophosphamide, chlorambucil, carmustine, lomustine, daunorubicin, doxorubicin, darubicin, mitoxantrone, trastuzuma, tamoxifen, toremifene, droloxifene, faslodex, raloxifene, exemestane, anastxozole, letrazole, vorozole, vitamin D, accutane, azacytidine, flavoperidol, imatinib mesylate, and gefitinib.

11. The compound of claim 3, wherein $R^{11}$ is hydrogen.

12. The compound of claim 3, wherein R is heteroaryl or substituted heteroaryl.

13. The compound of claim 3, wherein T is —$SO_2$—.

14. The compound of claim 3, wherein T is —$SO_2NH$—$CH_2$—.

15. The compound of claim 3, wherein:
R is aryl or substituted aryl;
$R^{12}$ is —$NR^{14}OH$, OH or $NR^{14}R_{15}$;
Y is CH; and
T is —$SO_2$— or —$SO_2NR^{16}CH_2$—.

16. The compound of claim 15, wherein $R^{12}$ is —$NH^{14}OH$ and T is —$SO_2NR^{16}CH_2$—.

17. The compound of claim 15, wherein $R^{12}$ is —$NR^{14}OH$ and T is —$SO_2$—.

18. The compound of claim 15, wherein R is aryl.

19. The compound of claim 15, wherein R is substituted aryl.

* * * * *